US012744230B2

(12) United States Patent
Kusama et al.

(10) Patent No.: US 12,744,230 B2
(45) **Date of Patent: *Sep. 22, 2026**

(54) ELECTRON CARRIER, ELECTRON CARRIER PRODUCTION METHOD, AND ELECTRON TRANSFER METHOD

(71) Applicant: Panasonic Intellectual Property Management Co., Ltd., Osaka (JP)

(72) Inventors: Shoko Kusama, Kyoto (JP); Seiji Kojima, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1131 days.

This patent is subject to a terminal disclaimer.

(21) Appl. No.: 17/748,678

(22) Filed: May 19, 2022

(65) Prior Publication Data

US 2022/0293990 A1 Sep. 15, 2022

Related U.S. Application Data

(63) Continuation of application No. PCT/JP2020/042553, filed on Nov. 16, 2020.

(30) Foreign Application Priority Data

Nov. 21, 2019 (JP) ................................ 2019-210255

(51) Int. Cl.

*H01M 8/16* (2006.01)
*C07K 14/195* (2006.01)
*C12N 9/10* (2006.01)
*C12N 15/74* (2006.01)

(52) U.S. Cl.

CPC ............. *H01M 8/16* (2013.01); *C07K 14/195* (2013.01); *C12N 9/10* (2013.01); *C12N 15/74* (2013.01)

(58) Field of Classification Search

CPC .................................................... C07K 14/195

See application file for complete search history.

(56) References Cited

U.S. PATENT DOCUMENTS

2017/0159084 A1 6/2017 Kawahara et al.

FOREIGN PATENT DOCUMENTS

| | | |
|---|---|---|
| JP | 6341676 | 6/2018 |
| JP | 2018-142408 | 9/2018 |

OTHER PUBLICATIONS

Hansel, A. & Tadros, M.H., "Characterization of Two Pore-Forming Proteins Isolated from the Outer Membrane of Synechococcus PCC 6301" Current Microbiology vol. 36 (1998), pp. 321-326.*

International Search Report (ISR) issued on Jan. 19, 2021 in International (PCT) Application No. PCT/JP2020/042553.

Gralnick, J.A. et al., "Extracellular respiration", Molecular Microbiology, vol. 65, No. 1, 2007, pp. 1-11.

Guo, J. et al., "Light-driven fine chemical production in yeast biohybrids", Science, vol. 362, No. 6416, Nov. 2018, pp. 813-816.

Mccormick, A.J. et al., "Photosynthetic biofilms in pure culture harness solar energy in a mediatorless bio-photovoltaic cell (BPV) system", Energy & Environmental Science, vol. 4, 2011, pp. 4699-4709.

Ducat, D.C. et al., "Engineering cyanobacteria to generate high-value products", Trends in Biotechnology, vol. 29, No. 2, 2011, pp. 95-103.

Hasan, K. et al., "Photo-electrochemical communication between cyanobacteria (*Leptolyngbia* sp.) and *Osmium redox* polymer modified electrodes", Physical Chemistry Chemical Physics, vol. 16, 2014, pp. 24676-24680.

Zhang, J.Z. et al., "Photoelectrochemistry of Photosystem II in Vitro vs in Vivo", Journal of the American Chemical Society, vol. 140, 2018, pp. 6-9.

Nishio, K. et al., "Electrochemical Detection of Circadian Redox Rhythm in Cyanobacterial Cells via Extracellular Electron Transfer", Plant and Cell Physiology, vol. 56, No. 6, 2015, pp. 1053-1058.

Van de Meene, A.M.L. et al., "The three-dimensional structure of the cyanobacterium *Synechocystis* sp. PCC 6803", Arch Microbiol, vol. 184, 2006, pp. 259-270.

Jürgens, U.J. et al., "Polysaccharide Covalently Linked to the Peptidoglycan of the *Cyanobacterium synechocystis* sp. Strain PCC6714", Journal of Bacteriology, vol. 168, No. 2, Nov. 1986, pp. 568-573.

Mesnage, S. et al., "Bacterial SLH domain proteins are non-covalently anchored to the cell surface via a conserved mechanism involving wall polysaccharide pyruvylation", The EMBO Journal, vol. 19, No. 17, 2000, pp. 4473-4484.

Kowata, H. et al., "Outer Membrane Permeability of *Cyanobacterium synechocystis* sp. Strain PCC 6803: Studies of Passive Diffusion of Small Organic Nutrients Reveal the Absence of Classical Porins and Intrinsically Low Permeability", Journal of Bacteriology, vol. 199, No. 19, Oct. 2017.

Kojima, S. et al., "Peptidoglycan-associated outer membrane protein Mep45 of rumen anaerobe Selenomonas ruminantium forms a non-specific diffusion pore via its C-terminal transmembrane domain", Bioscience, Biotechnology, and Biochemistry, vol. 80, No. 10, 2016, pp. 1954-1959.

Nikaido, H. "Molecular Basis of Bacterial Outer Membrane Permeability Revisited", Microbiology and Molecular Biology Reviews, vol. 67, No. 4, Dec. 2003, pp. 593-656.

(Continued)

*Primary Examiner* — Suzanne M Noakes

(74) *Attorney, Agent, or Firm* — Wenderoth, Lind & Ponack, L.L.P.

(57) ABSTRACT

An electron carrier includes a modified cyanobacterium in which at least: (i) a function of a protein involved in binding between an outer membrane and a cell wall of cyanobacterium is suppressed or lost; or (ii) a channel protein which improves protein permeability of the outer membrane is expressed. The modified cyanobacterium performs at least one of supplying electrons to an outside or taking in electrons from the outside.

8 Claims, 10 Drawing Sheets

Specification includes a Sequence Listing.

(56) References Cited

OTHER PUBLICATIONS

Ponce-Toledo, R.I. et al., "An Early-Branching Freshwater Cyanobacterium at the Origin of Plastids", Current Biology, vol. 27, Feb. 2017, pp. 386-391.

Kojima, S. et al., "Outer Membrane Proteins Derived from Non-cyanobacterial Lineage Cover the Peptidoglycan of Cyanophora paradoxa Cyanelles and Serve as a Cyanelle Diffusion Channel", Journal of Biological Chemistry, vol. 291, No. 38, Sep. 2016, pp. 20198-20209.

Yao, L. et al., "Multiple Gene Repression in Cyanobacteria Using CRISPRi", ACS Synthetic Biology, vol. 5, 2016, pp. 207-212.

Jiménez-Gómez, A. et al., "Probiotic activities of Rhizobium laguerreae on growth and quality of spinach", Scientific Reports, vol. 8, 2018, Article No. 295.

Çakmakçi, R. et al., "The influence of plant growth—promoting rhizobacteria on growth and enzyme activities in wheat and spinach plants", Journal of Plant Nutrition and Soil Science, vol. 170, 2007, pp. 288-295.

Kojima, S. et al., "Outer membrane-deprived cyanobacteria liberate periplasmic and thylakoid luminal components that support the growth of heterotrophs", bioRxiv, [online], Mar. 25, 2020, Internet <URL: https://doi.org/10.1101/2020.03.24.006684>.

Kowata, H. "Studies on molecular basis of cyanobacterial outer membrane function and evolutionary relationship with primitive chloroplasts", Dissertation, Tohoku University, Mar. 2018.

Kojima, S. "Elucidation and application of bacterial-derived membrane stabilizer mechanism and substance permeation mechanism that functions in the chloroplast membrane surfaces", KAKENHI [online], Apr. 23, 2018, Internet <URL: https://kaken.nii.ac.jp/ja/grant/KAKENHI-PROJECT-18H02117/> with English translation.

Office Action with the Search Report issued Nov. 20, 2023 in corresponding Chinese Patent Application No. 202080078392.7, with English-language translation.

GenBank Accession No. BAA17449.1, dated Oct. 7, 2016, slr1841 [*Synechocystis* sp. PCC 6803], Kaneko T et al.

GenBank Accession No. BAA16977.1, dated Oct. 7, 2016, slr0688 [*Synechocystis* sp. PCC 6803], Kaneko T et al.

Office Action issued Sep. 24, 2025 in European Patent Application No. 20 890 054.8.

Paulo Oliveira et al: "The versatile TolC-like Slr1270 in the cyanobacterium *Synechocystis* sp. PCC 6803", Environmental Microbiology, Blackwell Science, GB, vol. 18, No. 2, Jan. 21, 2016 (Jan. 21, 2016), pp. 486-502, XP072195377.

* cited by examiner

ELECTRON CARRIER, ELECTRON CARRIER PRODUCTION METHOD, AND ELECTRON TRANSFER METHOD

CROSS REFERENCE TO RELATED APPLICATIONS

This is a continuation application of PCT International Application No. PCT/JP2020/042553 filed on Nov. 16, 2020, designating the United States of America, which is based on and claims priority of Japanese Patent Application No. 2019-210255 filed on Nov. 21, 2019. The entire disclosures of the above-identified applications, including the specifications, drawings and claims are incorporated herein by reference in their entirety.

FIELD

The present disclosure relates to an electron carrier including modified cyanobacterium, an electron carrier production method, and an electron transfer method.

BACKGROUND

Technology development exploiting a phenomenon in which microbial cells perform electron transfer with an extracellular environment has received attention in recent years. For example, Gram-negative bacteria of the genus *Shewanella* or *Geobacter* are known to release electrons resulting from the intracellular catabolism of organic substances to the outside of cells via a biomolecule, such as cytochrome, having an electron transfer function (Non Patent Literature (NPL) 1). Bioelectrochemical systems (e.g., power generation apparatuses) that can achieve the retrieval of resources from organic effluents are expected by introducing such a phenomenon to, for example, sewage treatment techniques (Patent Literature (PTL) 1). Intracellular electrons resulting from photosynthesis may be utilized as microbial solar cells (NPL 3). It has also been reported that, for example, electrode surface modification (NPL 5 and 6) or mediator compounds (NPL 7) improve the electron transfer efficiency between cyanobacterium and electrodes. Cyanobacterium is known to produce various useful substances (e.g., alcohols, alkanes, and fatty acids) by photosynthesis, in addition to extracellular electron transfer (PTL 2 and NPL 4).

Meanwhile, technology development is also ongoing with the aim of improvement in the efficiency of bio-manufacturing by sending electrons to microbial cells from the outside of the cells and thereby activating the metabolism of the microbial cells (e.g., NPL 2).

CITATION LIST

Patent Literature

PTL 1: Japanese Unexamined Patent Application Publication No. 2018-142408

PTL 2: Japanese Patent No. 6341676

Non Patent Literature

NPL 1: J. A. Gralnick and D. K. Newman, "Extracellular respiration", Molecular Microbiology, Wiley-Blackwell, 2007, Vol. 65, pp. 1-11

NPL 2: Junling Guo et al., "Light-driven fine chemical production in yeast biohybrids", Science, American Association for the Advancement of Science, 2018, Vol. 362, Issue 6416, pp. 813-816

NPL 3: Alistair J. McCormick et al., "Photosynthetic biofilms in pure culture harness solar energy in a mediatorless bio-photovoltaic cell (BPV) system", Energy & Environmental Science, Royal Society of Chemistry, 2011, Vol. 4, pp. 4699-4709

NPL 4: Ducat D C et al., "Engineering cyanobacteria to generate high-value products", Trends in Biotechnology, Elsevier B V, 2011, Vol. 29, pp. 95-103

NPL 5: Hasan K et al., "Photo-electrochemical communication between cyanobacteria (*Leptolyngbia* sp.) and osmium redox polymer modified electrodes", Physical Chemistry Chemical Physics, Royal Society of Chemistry, 2014, Vol. 16, pp. 24676-24680

NPL 6: Jenny Z. Zhang et al., "Photoelectrochemistry of Photosystem II in Vitro vs in Vivo", Journal of American Chemical Society, American Chemical Society, 2018, Vol. 140, pp. 6-9

NPL 7: Nishio K et al., "Electrochemical detection of circadian redox rhythm in cyanobacterial cells via extracellular electron transfer", Plant and Cell Physiology, Japanese Society of Plant Physiologists, 2015, Vol. 56, pp. 1053-1058

SUMMARY

Technical Problem

However, in the aforementioned conventional techniques, efficiency of electron transfer to and from the outside of the cell of cyanobacterium is low, and thus there is a demand for improving efficiency of electron transfer to and from the outside of cells.

In view of this, the present disclosure provides an electron carrier, an electron carrier production method, and an electron transfer method in which efficiency of electron transfer with the outside is improved by including a modified cyanobacterium having improved efficiency of electron transfer to and from the outside of cells.

Solution to Problem

An electron carrier according to an aspect of the present disclosure includes a modified cyanobacterium in which at least: (i) a function of a protein involved in binding between an outer membrane and a cell wall of cyanobacterium is suppressed or lost; or (ii) a channel protein which improves protein permeability of the outer membrane is expressed, wherein the modified cyanobacterium performs at least one of supplying electrons to an outside or taking in electrons from the outside.

Advantageous Effects

According to the electron carrier and electron carrier production method according to the present disclosure, it is possible to provide an electron carrier having improved efficiency of electron transfer with the outside. Furthermore, according to the electron transfer method according to the present disclosure, efficiency of at least one of supplying electrons from an electron carrier to the outside or receiving electrons from the outside to the electron carrier is improved.

BRIEF DESCRIPTION OF DRAWINGS

These and other advantages and features will become apparent from the following description thereof taken in conjunction with the accompanying Drawings, by way of non-limiting examples of embodiments disclosed herein.

DESCRIPTION OF EMBODIMENTS

Figure 1:
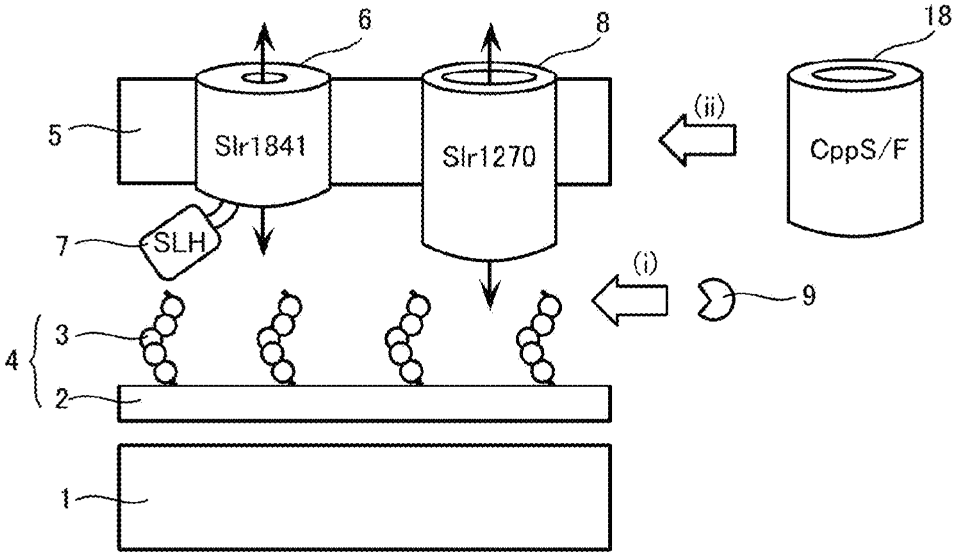
FIG. 1 is a diagram schematically illustrating a cell surface of a cyanobacterium.

Underlying Knowledge Forming Basis of Present Disclosure

Technology exploiting a phenomenon in which microbial cells perform electron transfer with an extracellular environment has received attention in recent years. For example, Gram-negative bacteria of the genus *Shewanella* or *Geobacter* are known to release electrons resulting from the intracellular catabolism of organic substances to the outside of cells via a biomolecule, such as cytochrome, having an electron transfer function (NPL 1). The electrons thus released from microbes can be utilized as microbial fuel cells with organic substances as fuel, if received by external electrodes. Application such as utilization as power generation apparatuses is expected by introducing such microbes, for example, to sewage treatment that involves organic substances (PTL 1).

Meanwhile, technology development is also ongoing with the aim of improvement in the efficiency of bio-manufacturing by sending electrons to microbial cells from the outside of the cells and thereby activating the metabolism of the cells. For example, NPL 2 has reported that the efficiency of shikimic acid production from a starting material glucose can be improved by attaching indium phosphide nanoparticles to yeast cells, and replenishing reducing power for use in intracellular metabolism by the cellular uptake of electrons generated through the photoelectric conversion reaction of the nanoparticles.

The utilization of microbes as described above does not depend on chemical fuel and can achieve energy production and bio-manufacturing with low environmental load. Among others, photosynthetic microbes such as cyanobacterium and algae can utilize carbon dioxide ($CO_2$) in air as a carbon source with light as an energy source and are therefore particularly expected as carbon-neutral next-generation bio-manufacturing systems.

Cyanobacterium (also called blue-green bacterium or blue-green alga), a group of *eubacterium*, produces oxygen by splitting water through photosynthesis, and fixes $CO_2$ in air. Cyanobacterium can also fix nitrogen ($N_2$) in air, depending on its species. Rapid growth and high light use efficiency are known as characteristics of cyanobacterium. In addition, its genetic manipulation is easier than that of other eukaryotic alga species. Therefore, the utilization of cyanobacterium among the photosynthetic microbes is under active research and development.

For example, provided that electrons generated in cyanobacterium cells at the time of splitting of water by photosynthesis are received by external electrodes through the use of the property of performing extracellular electron transfer by cyanobacterium, a simple configuration having water, cyanobacterium, and a pair of electrodes can be utilized as a microbial solar cell (NPL 3).

Alcohols, alkanes, and fatty acids, etc. have been reported as examples of bio-manufacturing using cyanobacterium (PTL 2 and NPL 4). Cyanobacterium, albeit having high photosynthetic ability, cannot obtain sufficient light energy under weak light, for example, during night-time or evening or in rainy or overcast weather. Hence, it is expected that if electrons can be sent into cyanobacterium cells from the outside of the cells, this leads to improvement in bio-manufacturing efficiency because intracellular reducing power which becomes insufficient during night-time or under weak light can be replenished from the outside.

Electrode surface modification (NPL 5 and 6) and mediator compounds (NPL 7) have been reported as approaches for improving the electron transfer efficiency between cyanobacterium and external electrodes.

Although technology development on the application of extracellular electron transfer of cyanobacterium is expected, as described above, the electron transfer efficiency is still at a low level. Thus, there is a demand for the development of technology more enhancing extracellular electron transfer efficiency.

The present inventors have conducted diligent studies to solve these problems and consequently found that a modified cyanobacterium improves the electron transfer efficiency between cells and external electrodes by partially detaching the outer membrane of cyanobacterium from a cell wall or by improving the material permeability of the outer membrane. More specifically, it has been found that, by the detachment of the outer membrane of cyanobacterium or improvement in material permeability, a modified cyanobacterium can perform at least one of secreting an intracellular electron carrier to the outside of the cell or taking an electron carrier from the outside of the cell into the cell. This improves the extracellular electron transfer efficiency of the modified cyanobacterium. Therefore, an electron carrier comprising the modified cyanobacterium can efficiently perform electron transfer with the outside.

In view of this, the present disclosure provides an electron carrier and an electron carrier production method which have improved efficiency of electron transfer with the outside. Furthermore, the present disclosure provides an electron transfer method that improves efficiency of at least one of supplying electrons from an electron carrier to the outside or receiving electrons from the outside to the electron carrier.

Outline of Present Disclosure

An outline of an aspect of the present disclosure is as described below.

An electron carrier according to an aspect of the present disclosure includes a modified cyanobacterium in which at least: (i) a function of a protein involved in binding between an outer membrane and a cell wall of cyanobacterium is suppressed or lost; or (ii) a channel protein which improves protein permeability of the outer membrane is expressed, wherein the modified cyanobacterium performs at least one of supplying electrons to an outside or taking in electrons from the outside.

Owing to the (i), the binding (e.g., binding level and binding force) between the cell wall and the outer membrane is partially reduced in the modified cyanobacterium. This facilitates partially detaching the outer membrane from the cell wall. Hence, intracellularly generated electrons or electron-containing substance or molecule easily leaks out to the outside of the outer membrane, i.e., the outside of the cell. Owing to the (ii), the protein permeability of the outer membrane is improved in the modified cyanobacterium. This improves the material permeability of the outer membrane. The modified cyanobacterium can thereby perform at least one of secreting intracellularly generated electrons or electron-containing substance or molecule to the outside of the cell or taking electrons or an electron-containing substance or molecule from the outside of the cell into the cell. Hence, the modified cyanobacterium has improved extracellular electron transfer efficiency. Thus, the electron carrier according to an aspect of the present disclosure has improved efficiency of electron transfer with the outside.

The outside is a substance or a molecule that exists as an individual different from the electron carrier, and is, for example, a redox substance involved in electron migration between materials, or a molecule having a redox reactive group.

For example, in the electron carrier according to an aspect of the present disclosure, the modified cyanobacterium may: under light, generate an electron; and release the electron generated to an outside of the outer membrane.

The modified cyanobacterium thereby releases electrons or an electron-containing substance or molecule to the outside of the cell under light. Hence, the electron carrier according to an aspect of the present disclosure can generate electrons in the inside upon light irradiation and supply electrons or an electron-containing substance or molecule to the outside.

For example, in the electron carrier according to an aspect of the present disclosure, the modified cyanobacterium may: take an electron present outside the outer membrane into an inside of the cell wall; and use the electron inside the cell wall.

The modified cyanobacterium thereby takes extracellularly occurring electrons or electron-containing substance or molecule into the cell (into the cytoplasm) and generates energy (ATP: adenosine triphosphate), for example, during a process of flowing in a photosynthetic electron transfer system. The modified cyanobacterium then produces organic substances on the basis of carbon dioxide through the use of this energy. Hence, the electron carrier according to an aspect of the present disclosure can produce organic substances such as protein by taking electrons from the outside into the inside and generating energy.

For example, in the electron carrier according to an aspect of the present disclosure, in the (i), the protein involved in the binding between the outer membrane and the cell wall may be at least one of a surface layer homology (SLH) domain-containing outer membrane protein or a cell wall-pyruvic acid modifying enzyme.

As a result, in the modified cyanobacterium, for example, (a) a function of at least one of a SLH domain-containing outer membrane protein which binds to the cell wall and an enzyme that catalyzes reaction to modify a linked sugar chain on the surface of the cell wall with pyruvic acid (i.e., a cell wall-pyruvic acid modifying enzyme) is suppressed or lost, or (b) the expression of at least one of the SLH domain-containing outer membrane protein or the cell wall-pyruvic acid modifying enzyme is suppressed. Hence, the binding (i.e., binding level and binding force) between the SLH domain of the SLH domain-containing outer membrane protein in the outer membrane and a covalently linked sugar chain on the surface of the cell wall is reduced. As a result, the outer membrane is easily detached from the cell wall at a site having the weakened binding between the outer membrane and the cell wall. The modified cyanobacterium can thereby perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the electron carrier according to an aspect of the present disclosure has improved efficiency of electron transfer with the outside.

For example, in the electron carrier according to an aspect of the present disclosure, the SLH domain-containing outer membrane protein may be: Slr1841 having an amino acid sequence represented by SEQ ID NO: 1; NIES970_09470 having an amino acid sequence represented by SEQ ID NO: 2; Anacy_3458 having an amino acid sequence represented by SEQ ID NO: 2; or a protein having an amino acid sequence that is at least 50 percent identical to the amino acid sequence of any one of the Slr1841, the NIES970_09470, and the Anacy_3458.

As a result, in the modified cyanobacterium, for example, (a) the function of the SLH domain-containing outer membrane protein represented by any one of SEQ ID NOs: 1 to 3 or a protein having an amino acid sequence that is at least 50 percent identical to the amino acid sequence of any one of these SLH domain-containing outer membrane proteins is suppressed or lost, or (b) the expression of the SLH domain-containing outer membrane protein represented by any one of SEQ ID NOs: 1 to 3 or a protein having an amino acid sequence that is at least 50 percent identical to the amino acid sequence of any one of these SLH domain-containing outer membrane proteins is suppressed. Hence, in the modified cyanobacterium, (a) the function of the SLH domain-containing outer membrane protein or a protein functionally equivalent to the SLH domain-containing outer membrane protein in the outer membrane is suppressed or lost, or (b) the expression level of the SLH domain-containing outer membrane protein or a protein functionally equivalent to the SLH domain-containing outer membrane protein in the outer membrane is decreased. As a result, in the modified cyanobacterium, the binding level and binding force of a binding domain (e.g., the SLH domain) of the outer membrane that binds to the cell wall are reduced. This facilitates partially detaching the outer membrane from the cell wall. Thus, the electron carrier according to an aspect of the present disclosure has improved efficiency of electron transfer with the outside.

For example, in the electron carrier according to an aspect of the present disclosure, the cell wall-pyruvic acid modifying enzyme may be: Slr0688 having an amino acid sequence represented by SEQ ID NO: 4; Synpcc7942_1529 having an amino acid sequence represented by SEQ ID NO: 5; Anacy_1623 having an amino acid sequence represented by SEQ ID NO: 6; or a protein having an amino acid sequence that is at least 50 percent identical to the amino acid sequence of any one of the Slr0688, the Synpcc7942_1529, and the Anacy_1623.

As a result, in the modified cyanobacterium, for example, (a) the function of the cell wall-pyruvic acid modifying enzyme represented by any one of SEQ ID NOs: 4 to 6 or a protein having an amino acid sequence that is at least 50 percent identical to the amino acid sequence of any one of these cell wall-pyruvic acid modifying enzymes is suppressed or lost, or (b) the expression of the cell wall-pyruvic acid modifying enzyme represented by any one of SEQ ID NOs: 4 to 6 or a protein having an amino acid sequence that is at least 50 percent identical to the amino acid sequence of any one of these cell wall-pyruvic acid modifying enzymes is suppressed. Hence, in the modified cyanobacterium, (a) the function of the cell wall-pyruvic acid modifying enzyme or a protein functionally equivalent to the enzyme is suppressed or lost, or (b) the expression level of the cell wall-pyruvic acid modifying enzyme or a protein functionally equivalent to the enzyme is decreased. A covalently linked sugar chain on the surface of the cell wall is thereby less susceptible to modification with pyruvic acid, so that binding level and binding force of the sugar chain of the cell wall that binds to the SLH domain of the SLH domain-containing outer membrane protein in the outer membrane are reduced. As a result, in the modified cyanobacterium, a covalently linked sugar chain on the surface of the cell wall is less susceptible to modification with pyruvic acid, so that binding force between the cell wall and the outer membrane is weakened. This facilitates partially detaching the outer membrane from the cell wall. Thus, the electron carrier according to an aspect of the present disclosure has improved efficiency of electron transfer with the outside.

For example, in the electron carrier according to an aspect of the present disclosure, in the (i), a gene which causes expression of the protein involved in the binding between the outer membrane and the cell wall may be deleted or inactivated.

As a result, in the modified cyanobacterium of the (i), the expression of the protein involved in the binding between the cell wall and the outer membrane is suppressed, or the function of the protein is suppressed or lost. Therefore, the binding (i.e., binding level and binding force) between the cell wall and the outer membrane is partially reduced. As a result, the outer membrane is easily detached from the cell wall at a site having the weakened binding between the outer membrane and the cell wall. The modified cyanobacterium of the (i) can thereby perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the electron carrier according to an aspect of the present disclosure has improved efficiency of electron transfer with the outside.

For example, in the electron carrier according to an aspect of the present disclosure, the gene which causes expression of the protein involved in the binding between the outer membrane and the cell wall may be at least one of a gene encoding an SLH domain-containing outer membrane protein or a gene encoding a cell wall-pyruvic acid modifying enzyme.

As a result, in the modified cyanobacterium, at least one of the gene encoding the SLH domain-containing outer membrane protein and the gene encoding the cell wall-pyruvic acid modifying enzyme is deleted or inactivated. Hence, in the modified cyanobacterium, for example, (a) the expression of at least one of the SLH domain-containing outer membrane protein or the cell wall-pyruvic acid modifying enzyme is suppressed, or (b) the function of at least one of the SLH domain-containing outer membrane protein or the cell wall-pyruvic acid modifying enzyme is suppressed or lost. Hence, the binding (i.e., binding level and binding force) between the SLH domain of the SLH domain-containing outer membrane protein in the outer membrane and a covalently linked sugar chain on the surface of the cell wall is reduced. As a result, in the modified cyanobacterium, the outer membrane is easily detached from the cell wall at a site having the weakened binding between an outer membrane and a cell wall, so that intracellular electrons or electron-containing substance or molecule easily leaks out to the outside of the cell. Thus, the electron carrier according to an aspect of the present disclosure has improved efficiency of electron transfer with the outside because in the modified cyanobacterium, intracellular electrons or electron-containing substance or molecule easily leaks out to the outside of the cell.

In the electron carrier according to an aspect of the present disclosure, the gene encoding the SLH domain-containing outer membrane protein may be: slr1841 having a nucleotide sequence represented by SEQ ID NO: 7; nies970_09470 having a nucleotide sequence represented by SEQ ID NO: 8; anacy_3458 having a nucleotide sequence represented by SEQ ID NO: 9; or a gene having a nucleotide sequence that is at least 50 percent identical to the nucleotide sequence of any one of the slr1841, the nies970_09470, and the anacy_3458.

As a result, in the modified cyanobacterium, the gene encoding the SLH domain-containing outer membrane protein, represented by any one of SEQ ID NOs: 7 to 9 or a gene having a nucleotide sequence that is at least 50 percent identical to the nucleotide sequence of any one of these genes is deleted or inactivated. Hence, in the modified cyanobacterium, (a) the expression of any one of the SLH domain-containing outer membrane proteins described above or a protein functionally equivalent to any one of these proteins is suppressed, or (b) the function of any one of the SLH domain-containing outer membrane proteins described above or a protein functionally equivalent to any one of these proteins is suppressed or lost. Hence, in the modified cyanobacterium, the binding level and binding force of a cell wall binding domain (e.g., the SLH domain) of the outer membrane that binds to the cell wall are reduced. This facilitates partially detaching the outer membrane from the cell wall, so that intracellular electrons or electron-containing substance or molecule easily leaks out to the outside of the cell. The modified cyanobacterium thereby has improved extracellular electron transfer efficiency. Thus, the electron carrier according to an aspect of the present disclosure has improved efficiency of electron transfer with the outside.

For example, in the electron carrier according to an aspect of the present disclosure, the gene encoding the cell wall-pyruvic acid modifying enzyme may be: slr0688 having a nucleotide sequence represented by SEQ ID NO: 10; synpcc7942_1529 having a nucleotide sequence represented by SEQ ID NO: 11; anacy_1623 having a nucleotide sequence represented by SEQ ID NO: 12; or a gene having a nucleotide sequence that is at least 50 percent identical to the nucleotide sequence of any one of the slr0688, the synpcc7942_1529, and the anacy_1623.

As a result, in the modified cyanobacterium, the gene encoding the cell wall-pyruvic acid modifying enzyme, represented by any one of SEQ ID NOs: 10 to 12 or a gene having a nucleotide sequence that is at least 50 percent identical to the nucleotide sequence of any one of these enzyme-encoding genes is deleted or inactivated. Hence, in the modified cyanobacterium, (a) the expression of any one of the cell wall-pyruvic acid modifying enzymes described above or a protein functionally equivalent to any one of these enzymes is suppressed, or (b) the function of any one of the cell wall-pyruvic acid modifying enzymes described above or a protein functionally equivalent to any one of these enzymes is suppressed or lost. A covalently linked sugar chain on the surface of the cell wall is thereby less susceptible to modification with pyruvic acid, so that binding level and binding force of the sugar chain of the cell wall that binds to the SLH domain of the SLH domain-containing outer membrane protein in the outer membrane are reduced. As a result, in the modified cyanobacterium, a decreased amount of a covalently linked sugar chain on the surface of the cell wall is modified with pyruvic acid, so that binding force between the cell wall and the outer membrane is weakened. This facilitates partially detaching the outer membrane from the cell wall. As a result, in the modified cyanobacterium, intracellular electrons or electron-containing substance or molecule easily leaks out to the outside of the cell. This improves extracellular electron transfer efficiency. Thus, the electron carrier according to an aspect of the present disclosure has improved efficiency of electron transfer with the outside.

For example, in the electron carrier according to an aspect of the present disclosure, in the (ii), the channel protein which improves the protein permeability of the outer membrane may be: CppS having an amino acid sequence represented by SEQ ID NO: 13; CppF having an amino acid sequence represented by SEQ ID NO: 14; or a protein having an amino acid sequence that is at least 50 percent identical to the amino acid sequence of either one the CppS and the CppF.

As a result, in the modified cyanobacterium of the (ii), CppS (SEQ ID NO: 13) or CppF (SEQ ID NO: 14) serving as the channel protein which improves protein permeability of the outer membrane, or a protein functionally equivalent to any one of these channel proteins is expressed. Hence, in the modified cyanobacterium of the (ii), the protein permeability of the outer membrane is improved, so that the material permeability of the outer membrane is improved. As a result, the modified cyanobacterium of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the electron carrier according to an aspect of the present disclosure has improved efficiency of electron transfer with the outside.

For example, in the electron carrier according to an aspect of the present disclosure, in the (ii), a gene encoding the channel protein which improves the protein permeability of the outer membrane may have been introduced.

As a result, in the modified cyanobacterium of the (ii), the channel protein which improves protein permeability of the outer membrane is expressed. Hence, in the modified cyanobacterium of the (ii), the protein permeability of the outer membrane is improved, so that the material permeability of the outer membrane is improved. As a result, the modified cyanobacterium of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the electron carrier according to an aspect of the present disclosure has improved efficiency of electron transfer with the outside.

For example, in the electron carrier according to an aspect of the present disclosure, the gene encoding the channel protein which improves the protein permeability of the outer membrane may be a chloroplast-derived gene. For example, the gene encoding the channel protein which improves the protein permeability of the outer membrane may be: cppS having a nucleotide sequence represented by SEQ ID NO: 15; cppF having a nucleotide sequence represented by SEQ ID NO: 16; or a gene having a nucleotide sequence that is at least 50 percent identical to the nucleotide sequence of either one of the cppS and the cppF.

As a result, in the modified cyanobacterium of the (ii), the gene encoding the channel protein, represented by any one of SEQ ID NO: 15 and SEQ ID NO: 16 or a gene having a nucleotide sequence that is 50 percent identical to the nucleotide sequence of any one of these genes is introduced. Hence, in the modified cyanobacterium of the (ii), the protein having the function of improving the protein permeability of the outer membrane or a protein functionally equivalent to the protein is expressed. As a result, in the modified cyanobacterium of the (ii), the protein permeability of the outer membrane is improved, so that the material permeability of the outer membrane is improved. As a result, the modified cyanobacterium of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the electron carrier according to an aspect of the present disclosure has improved efficiency of electron transfer with the outside.

Furthermore, an electron carrier production method according to an aspect of the present disclosure includes producing a modified cyanobacterium in which at least: (i) a function of a protein involved in binding between an outer membrane and a cell wall of cyanobacterium is suppressed or lost; or (ii) a channel protein which improves protein permeability of the outer membrane is expressed.

As a result, in the produced modified cyanobacterium, at least one of the following is realized: (i) the binding between the cell wall and the outer membrane is partially weakened, so that the outer membrane is easy to partially detach from the cell wall, or (ii) the protein permeability of the outer membrane is improved, so that the material permeability of the outer membrane is improved. The modified cyanobacterium can therefore perform at least one of secreting intracellular electrons or electron-containing substance or molecule to the outside of the cell or taking electrons or an electron-containing substance or molecule from the outside of the cell into the cell. As a result, the produced modified cyanobacterium has improved extracellular electron transfer efficiency. Thus, the electron carrier production method according to an aspect of the present disclosure can provide an electron carrier having improved efficiency of electron transfer with the outside.

Furthermore, an electron transfer method according to an aspect of the present disclosure uses any of the electron carriers described above.

The electron carrier thereby comprises the modified cyanobacterium having improved extracellular electron transfer efficiency and therefore, can efficiently supply electrons to the outside (e.g., external electrodes) and can efficiently receive electrons from the outside. Hence, use of the electron carrier enables current to be generated through the modified cyanobacterium contained in the electron carrier, which releases an intracellular electron transfer substance to the outside of the cell and thereby efficiently supplies electrons, for example, to external electrodes. For example, the modified cyanobacterium contained in the electron carrier can perform photosynthesis or respiration by receiving electrons instead of light energy from the outside. The modified cyanobacterium contained in the electron carrier can thereby intracellularly produce useful materials such as proteins and secrete them to the outside of the cell.

Hereinafter, embodiments will be described in detail with reference to the drawings.

It should be noted that each of the subsequently described embodiments shows a generic or specific example. Numerical values, materials, steps, the processing order of the steps indicated in the following embodiments are merely examples, and thus are not intended to limit the present disclosure. Furthermore, among the elements in the following embodiments, elements that are not described in the independent claims indicating the broadest concepts are described as optional elements.

Furthermore, the figures are not necessarily precise illustrations. In the figures, elements that are substantially the same are given the same reference signs, and overlapping description thereof may be omitted or simplified.

Moreover, in the following embodiments, numerical ranges include, not only the precise meanings, but also substantially equal ranges, such as, for example, a measured amount (for example, the number, the concentration, etc.) of a protein or a range thereof, etc.

In the present specification, both of a bacterial cell and a cell refer to one individual of cyanobacterium.

EMBODIMENT

1. Definitions

In the present specification, the identity of a nucleotide sequence or an amino acid sequence is calculated with Basic Local Alignment Search Tool (BLAST) algorithm. Specifically, the identity is calculated by pairwise analysis with the BLAST program available in the website of the National Center for Biotechnology Information (NCBI) (blast.ncbi.nlm.nih.gov). Information on cyanobacterium and plant genes and proteins encoded by these genes are published in, for example, the NCBI database mentioned above and Cyanobase (genome.microbedb.jp). The amino acid sequence of the protein of interest and the nucleotide sequence of a gene encoding the protein can be obtained from these databases.

Cyanobacterium, also called blue-green alga or blue-green bacterium, is a group of prokaryote that performs photosynthesis while generating oxygen through the splitting of water, by collecting light energy through chlorophyll and causing charge separation of the reaction center chlorophyll using the obtained energy. Cyanobacterium is highly diverse and includes, for example, unicellular species such as *Synechocystis* sp. PCC 6803 and filamentous species having multicellular filaments such as *Anabaena* sp. PCC 7120, in terms of cell shape. There are also thermophilic species such as *Thermosynechococcus elongatus*, marine species such as *Synechococcus elongatus*, and freshwater species such as *Synechocystis*, in terms of growth environment. Other examples thereof include many species having unique features, including species, such as *Microcystis aeruginosa*, which have a gas vesicle and produce toxin, and *Gloeobacter violaceus* which lacks thylakoid and has a light-harvesting antenna protein called phycobilisome in the plasma membrane.

Cyanobacterium intracellularly generates electrons when water is split by photosynthesis and when organic compounds such as sugars synthesized by photosynthesis are catabolized as its own nutrient sources. The electrons generated by the splitting of water flow in a photosynthetic electron transfer chain present on a thylakoid membrane, which is an intracytoplasmic membrane structure, while generating proton motive force, which is utilized as a bioenergy source, in the process. Finally, the electrons are used in reaction to reduce $NADP^+$ to generate NADPH.

On the other hand, the electrons generated from organic compounds by the catabolism of the organic compounds flow in respiratory chains present on the cytoplasmic membrane and on the thylakoid membrane while generating the proton motive force mentioned above in the process. Finally, the electrons are used in reaction to reduce oxygen ($O_2$) into water ($H_2O$). It has been found that the cytoplasmic membrane and the thylakoid membrane in cyanobacterium are linked (NPL 8: van de Meene et al., 2006, Arch. Microbiol., 184 (5): 259-270).

FIG. 1 is a diagram schematically illustrating a cell surface of a cyanobacterium. As illustrated in FIG. 1, the cell surface of cyanobacterium is constituted by a plasma membrane (also referred to as inner membrane 1), peptidoglycan 2, and outer membrane 5 which is a lipid membrane that forms the outermost layer of the cell, in order from the inside. Sugar chain 3 constituted by glucosamine and mannosamine, etc. is covalently linked to peptidoglycan 2, and pyruvic acid is bound with this covalently linked sugar chain 3 (NPL 9: Jurgens and Weckesser, 1986, J. Bacteriol., 168: 568-573). In the present specification, peptidoglycan 2 and covalently linked sugar chain 3 are collectively referred to as cell wall 4. The space between the plasma membrane (i.e., inner membrane 1) and outer membrane 5 is called periplasm where various enzymes involved in protein degradation or conformation formation, lipid or nucleic acid degradation, or uptake of extracellular nutrients, etc. are present.

An enzyme that catalyzes the pyruvic acid modification reaction of covalently linked sugar chain 3 (hereinafter, referred to as cell wall-pyruvic acid modifying enzyme 9) in peptidoglycan 2 was identified in a Gram-positive bacterium *Bacillus anthracis* and designated as CsaB (NPL 10: Mesnage et al., 2000, EMBO J., 19: 4473-4484). Many species of cyanobacterium whose genomic nucleotide sequence is published retains a gene encoding a homologous protein having an amino acid sequence that has 30% or higher identity to the amino acid sequence of CsaB. Examples thereof include slr0688 retained by *Synechocystis* sp. PCC 6803 and syn7502_03092 retained by *Synechococcus* sp. 7502.

SLH domain-containing outer membrane protein 6 (slr1841 in the figure) which retains SLH (surface layer homologous) domain 7 is bound to the cell wall of cyanobacterium (NPL 11: Kowata et al., 2017, J. Bacteriol., 199: e00371-17). It is known that a peptidoglycan-linked sugar chain is modified with pyruvic acid for the binding between the outer membrane protein and the cell wall (NPL 12: Kojima et al., 2016, Biosci. Biotech. Biochem., 10: 1954-1959).

Channel proteins refer to membrane proteins that form a pathway (i.e., a channel) for selectively allowing predetermined materials to permeate the lipid membrane (e.g., outer membrane 5) from the inside to the outside or from the outside to the inside. The outer membranes of general heterotrophic Gram-negative bacteria such as *E. coli* and *salmonella* are rich in a channel protein called Porin for selectively allowing relatively low-molecular-weight nutrients such as sugars and amino acids to permeate the outer membranes from the outside to the inside and taking them into the cells (NPL 13: Nikaido, 2003, Microbiol. Mol. Biol. Rev., 67 (4): 593-656). On the other hand, outer membrane 5 of cyanobacterium is free of Porin and is instead rich in an ion channel protein (e.g., SLH domain-containing outer membrane protein 6) which permits selective permeation of only inorganic ions. The ion channel protein accounts for approximately 80% of the total protein of the outer membrane 5 (NPL 11). Hence, in cyanobacterium, high-molecular-weight materials such as protein have the difficulty in permeating outer membrane 5 and diffusing to the outside of the cell (i.e., the outside of outer membrane 5), unless the properties of outer membrane 5 are largely altered by use of a technique such as gene introduction.

Plant chloroplast originated from cyanobacterium which coexisted within primitive eukaryotic cells approximately 1.5 to 2 billion years ago and then evolved into chloroplast (NPL 14: Ponce-Toledo et al., 2017, Curr. Biol., 27 (3): 386-391). Chloroplast retained by glaucophytes, which are unicellular algae reported as the most primitive plants, has peptidoglycan and exhibits a surface structure very similar to that of cyanobacterium. On the other hand, the chloroplast of seed plants more evolutionally advanced from unicellular algae is free of peptidoglycan. Many outer membrane proteins of cyanobacterium were lost from the chloroplast outer membranes at the initial stage of emergence of chloroplast during the course of evolution. Hence, the chloroplast outer membrane proteins of the glaucophytes mentioned above differ largely in configuration in the outer membrane proteins of cyanobacterium. For example, outer membrane 5 of cyanobacterium is rich in an ion channel protein, such as Slr1841 (SLH domain-containing outer membrane protein 6), which permits permeation of inorganic substances. The ion channel protein accounts for approximately 80% of the total protein of outer membrane 5. On the other hand, the chloroplast outer membranes of the glaucophytes are rich in channel proteins designated as CppS and CppF (hereinafter, also referred to as organic channel protein 18) which permit permeation of organic substances. This organic channel protein 18 accounts for 80% or more of the total protein of the chloroplast outer membrane of each glaucophyte (NPL 15: Kojima et al., 2016, J. Biol. Chem., 291: 20198-20209). CppS and CppF are channel proteins having a channel function for the selective permeation of relatively high-molecular-weight organic substances (e.g., biomolecules such as protein) and are considered to function as material transport pathways that connect the inside of the chloroplast in the plant cell to the cytoplasm of the plant cell. CppS and CppF are widely distributed in the glaucophytes. On the other hand, only bacteria belonging to the division *Planctomycetes* among bacterial have analogous proteins of CppS and CppF. Cyanobacterium retains none of CppS and CppF and their analogous proteins (see NPL 15).

2. Electron Carrier

Figure 2:
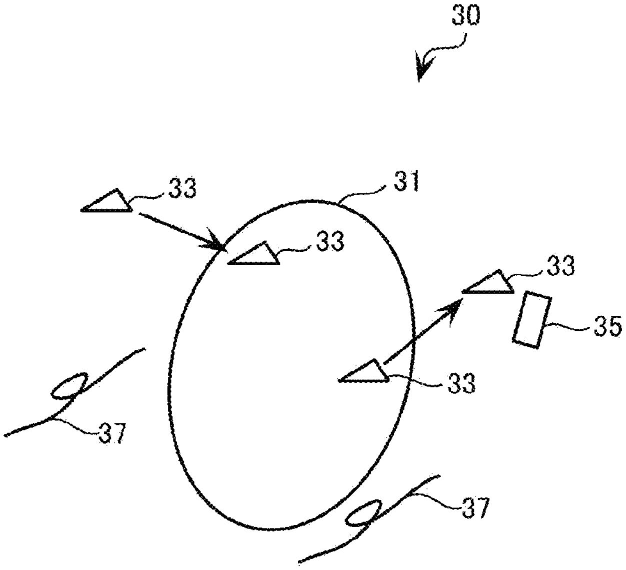
FIG. 2 is a schematic diagram illustrating an example of an electron carrier according to an embodiment.

Subsequently, the electron carrier according to the present embodiment will be described. FIG. 2 is a schematic diagram illustrating an example of electron carrier 30 according to the present embodiment.

Electron carrier 30 has a function of supplying electrons to an outside and taking in electrons from the outside. The outside is a substance or a molecule that exists as an individual different from electron carrier 30, and is, for example, a redox substance involved in electron migration between materials, or a molecule having a redox reactive group.

In this context, the phrase "supplying electrons" refers to not only supplying electrons but supplying every substance or molecule having electrons. The phrase "taking in electrons" refers to not only taking in electrons but taking in every substance or molecule having electrons.

Electron carrier 30 according to the present embodiment comprises modified cyanobacterium 31 in which at least: (i) a function of a protein involved in binding between outer membrane 5 and cell wall 4 of cyanobacterium (parent cyanobacterium mentioned later) is suppressed or lost; or (ii) a channel protein which improves protein permeability of outer membrane 5 (i.e., organic channel protein 18) is expressed. This modified cyanobacterium 31 performs at least one of supplying electrons to an outside of electron carrier 30 or taking in electrons from the outside.

For example, electron carrier 30 may be modified cyanobacterium 31 of the (i), may be modified cyanobacterium 31 of the (ii), or may be modified cyanobacterium 31 of the (i) and the (ii).

Owing to the (i), the binding (e.g., binding level and binding force) between cell wall 4 and outer membrane 5 is partially reduced in modified cyanobacterium 31. This facilitates partially detaching outer membrane 5 from cell wall 4. Hence, intracellularly generated electrons or electron-containing substance or molecule of modified cyanobacterium 31 easily leaks out to the outside of outer membrane 5, i.e., the outside of the cell. Owing to the (ii), the protein permeability of outer membrane 5 is improved in modified cyanobacterium 31. This improves the material permeability of outer membrane 5. Modified cyanobacterium 31 can thereby perform at least one of secreting intracellularly generated electrons or electron-containing substance or molecule to the outside of the cell or taking electrons or an electron-containing substance or molecule from the outside of the cell into the cell. As a result, modified cyanobacterium 31 has improved extracellular electron transfer efficiency. Thus, electron carrier 30 according to the present embodiment has improved efficiency of electron transfer with the outside.

Electron carrier 30 may comprise at least one of electron transfer substance 33, electron mediator 35, or conductive substance 37, in addition to at least one modified cyanobacterium 31 of the (i) or the (ii).

For example, as illustrated in FIG. 2, electron carrier 30 may comprise modified cyanobacterium 31, electron transfer substance 33, electron mediator 35, and conductive substance 37. Electron carrier 30 can thereby have further improved extracellular electron transfer efficiency of modified cyanobacterium 31.

In this context, electron transfer substance 33 is a substance responsible for electron transfer reaction and is a so-called redox substance including an oxidized substance which accepts electrons and a reduced substance which donates electrons. Electron transfer substance 33 is not particularly limited as long as it is a redox substance involved in an intracellular electron transfer system. Examples thereof may include peptide, protein, flavins, quinones, heme iron, non-heme iron such as iron-sulfur cluster, and copper ions.

Electron mediator 35 is a substance that assists or promotes the electron transfer function of electron transfer substance 33 and is a so-called redox active species. Electron mediator 35 may be any of, for example, quinones, ferrocene, ferricyanide, cytochromes, viologens, phenazines, phenoxazines, phenothiazines, ferredoxins, and their derivatives, and the substance may be appropriately selected according to the type of electron transfer substance 33.

Conductive substance 37 is a substance having the property of facilitating electron migration within the substance and may be selected from one or more materials selected from the group consisting of carbon-based materials, conductive polymers, semiconductors, and metals. In this context, the carbon-based material refers to a material having carbon as a constituent. The carbon-based material may be, for example, a carbon powder such as graphite, active carbon, or carbon black, a carbon fiber such as graphite felt, carbon wool, or woven carbon fabric, a carbon nanotube, a carbon plate, a carbon paper, or a carbon disk.

The conductive polymer is a generic name for high-molecular compounds having conductivity. The conductive polymer may be, for example, a single monomer having aniline, aminophenol, diaminophenol, pyrrole, thiophene, paraphenylene, fluorene, furan, acetylene, or a derivative thereof as a constituent unit, or a polymer of two or more such monomers. More specifically, examples of the conductive polymer may include polyaniline, polyaminophenol, polydiaminophenol, polypyrrole, polythiophene, polyfuran, and polyacetylene.

Alternatively, conductive substance 37 may be a metal or metal oxide and may be tungsten, tungsten oxide, copper, silver, platinum, gold, niobium, iron, cobalt, titanium, molybdenum, molybdenum oxide, tin, tin oxide, nickel, nickel oxide, or alloy containing them, or oxide thereof from the viewpoint of enhancing the amount of current produced.

These configurations may be appropriately selected according to the design of electron carrier 30.

3. Modified Cyanobacterium

Subsequently, modified cyanobacterium 31 will be described. In the present embodiment, modified cyanobacterium 31 is contained in electron carrier 30.

Modified cyanobacterium 31 generates an electron under light, and releases the electron generated to an outside of outer membrane 5. Modified cyanobacterium 31 thereby releases electrons or an electron-containing substance or molecule to the outside of the cell (i.e., the outside of outer membrane 5) under light. Hence, electron carrier 30 can generate electrons in the inside under light and supply electrons or an electron-containing substance or molecule to the outside.

Modified cyanobacterium 31 takes, for example, an electron present outside outer membrane 5 into an inside of cell wall 4 (i.e., the inside of the cytoplasm), and uses the electron inside cell wall 4. Modified cyanobacterium 31 thereby takes extracellularly occurring electrons or electron-containing substance or molecule into the cell (into the cytoplasm) and generates energy (ATP: adenosine triphosphate), for example, during a process of flowing in a photosynthetic electron transfer system. Modified cyanobacterium 31 then produces organic substances on the basis of carbon dioxide through the use of this energy. Hence, electron carrier 30 can produce organic substances such as protein by taking electrons from the outside into the inside and generating energy.

In modified cyanobacterium 31, at least (i) a function of a protein involved in binding between outer membrane 5 and cell wall 4 (hereinafter, also referred to as a binding-related protein) of cyanobacterium is suppressed or lost, or (ii) a channel protein which improves protein permeability of outer membrane 5 (i.e., organic channel protein 18) is expressed.

First, modified cyanobacterium 31 of the (i) will be described.

In the (i), the protein involved in binding between outer membrane 5 and cell wall 4 may be at least one of SLH domain-containing outer membrane protein 6 or cell wall-pyruvic acid modifying enzyme 9. In the present embodiment, in modified cyanobacterium 31, for example, the function of at least one of SLH domain-containing outer membrane protein 6 or cell wall-pyruvic acid modifying enzyme 9 is suppressed or lost. For example, in modified cyanobacterium 31, (a) the function of at least one of SLH domain-containing outer membrane protein 6 or cell wall-pyruvic acid modifying enzyme 9 may be suppressed or lost, or (b) at least one of the expression of SLH domain-containing outer membrane protein 6 which binds to cell wall 4 or an enzyme that catalyzes the pyruvic acid modification reaction of a linked sugar chain on the surface of cell wall 4 (i.e., cell wall-pyruvic acid modifying enzyme 9) may be suppressed.

As a result, in modified cyanobacterium 31, for example, (a) the function of at least one of SLH domain-containing outer membrane protein 6 which binds to the cell wall or an enzyme that catalyzes reaction to modify a linked sugar chain on the surface of the cell wall with pyruvic acid (i.e., cell wall-pyruvic acid modifying enzyme 9) is suppressed or lost, or (b) the expression of at least one of SLH domain-containing outer membrane protein 6 or cell wall-pyruvic acid modifying enzyme 9 is suppressed. Hence, the binding (i.e., binding level and binding force) between the SLH domain of the SLH domain-containing outer membrane protein in outer membrane 5 and covalently linked sugar chain 3 on the surface of cell wall 4 is reduced. As a result, outer membrane 5 is easily detached from cell wall 4 at a site having the weakened binding between outer membrane 5 and cell wall 4. Modified cyanobacterium 31 can thereby perform at least one of secreting intracellular electron transfer substance 33 to the outside of the cell or taking electron transfer substance 33 from the outside of the cell into the cell. This improves extracellular electron transfer efficiency. Thus, electron carrier 30 according to the present embodiment has improved efficiency of electron transfer with the outside.

The type of the cyanobacterium before (i) a function of a protein involved in binding between outer membrane 5 and cell wall 4 is suppressed or lost, or the cyanobacterium before (ii) a channel protein which improves protein permeability of outer membrane 5 (i.e., organic channel protein 18) is expressed (hereinafter, referred to as a parent cyanobacterium), which serves as the parent microbe of modified cyanobacterium 31 according to the present embodiment, is not particularly limited and may be any type of cyanobacterium. The parent cyanobacterium may be, for example, the genus *Synechocystis, Synechococcus, Anabaena*, or *Thermosynechococcus*, and may be *Synechocystis* sp. PCC 6803, *Synechococcus* sp. PCC 7942, or *Thermosynechococcus elongatus* BP-1 among them.

The amino acid sequences of (i) the protein involved in binding between outer membrane 5 and cell wall 4 and (ii) the channel protein which improves protein permeability of outer membrane 5 (organic channel protein 18) in the parent cyanobacterium, the nucleotide sequences of genes encoding these binding-related proteins, and the positions of the genes on chromosomal DNA or a plasmid can be confirmed in the NCBI database and Cyanobase mentioned above.

The protein involved in binding between an outer membrane and a cell wall, the function of which is suppressed or lost in modified cyanobacterium 31 according to the present embodiment may be from any parent cyanobacterium and is not limited by the location where a gene encoding it resides (e.g., on chromosomal DNA or on a plasmid) as long as the parent cyanobacterium carries it.

SLH domain-containing outer membrane protein 6 may be, for example, Slr1841, Slr1908, or Slr0042 when the parent cyanobacterium is the genus *Synechocystis*, may be NIES970_09470, etc. when the parent cyanobacterium is the genus *Synechococcus*, may be Anacy_5815 or Anacy_3458, etc. when the parent cyanobacterium is the genus *Anabaena*, may be A0A0F6U6F8_MICAE, etc. when the parent cyanobacterium is the genus *Microcystis*, may be A0A3B8XX12_9CYAN, etc. when the parent cyanobacterium is the genus *Cyanothece*, may be A0A1Q8ZE23_9CYAN, etc. when the parent cyanobacterium is the genus *Leptolyngbya*, includes A0A1Z4R6U0_9CYAN when the parent cyanobacterium is the genus *Calothrix*, may be A0A1COVG86_9NOSO, etc. when the parent cyanobacterium is the genus *Nostoc*, may be B1WRN6_CROS5, etc. when the parent cyanobacterium is the genus *Crocosphaera*, and may be K9TAE4_9CYAN, etc. when the parent cyanobacterium is the genus *Pleurocapsa*.

More specifically, SLH domain-containing outer membrane protein 6 may be, for example, Slr1841 (SEQ ID NO: 1) of *Synechocystis* sp. PCC 6803, NIES970_09470 (SEQ ID NO: 2) of *Synechococcus* sp. NIES-970, or Anacy_3458 (SEQ ID NO: 3) of *Anabaena cylindrica* PCC 7122. Alternatively, a protein having an amino acid sequence that is at least 50 percent identical to the amino acid sequence of any one of these SLH domain-containing outer membrane proteins 6 may be used.

As a result, in modified cyanobacterium 31, for example, (a) the function of SLH domain-containing outer membrane protein 6 represented by any one of SEQ ID NOs: 1 to 3 or a protein having an amino acid sequence that is at least 50 percent identical to the amino acid sequence of any one of these SLH domain-containing outer membrane proteins 6 may be suppressed or lost, or (b) the expression of SLH domain-containing outer membrane protein 6 represented by any one of SEQ ID NOs: 1 to 3 or a protein having an amino acid sequence that is at least 50 percent identical to the amino acid sequence of any one of these SLH domain-containing outer membrane proteins 6 may be suppressed. Hence, in modified cyanobacterium 31, (a) the function of SLH domain-containing outer membrane protein 6 or a protein functionally equivalent to SLH domain-containing outer membrane protein 6 in outer membrane 5 is suppressed or lost, or (b) the expression level of SLH domain-containing outer membrane protein 6 or a protein functionally equivalent to SLH domain-containing outer membrane protein 6 in outer membrane 5 is decreased. As a result, in modified cyanobacterium 31, the binding level and binding force of a binding domain (e.g., SLH domain 7) of outer membrane 5 that binds to cell wall 4 are reduced. This facilitates partially detaching outer membrane 5 from cell wall 4. Thus, electron carrier 30 according to the present embodiment has improved efficiency of electron transfer with the outside.

In general, a protein having an amino acid sequence that is at least 30 percent identical to the amino acid sequence of a protein has high conformational homology to the protein and therefore, is reportedly likely to be functionally equivalent to the protein. Hence, SLH domain-containing outer membrane protein 6, the function of which is suppressed or lost may be, for example, a protein or a polypeptide which has an amino acid sequence that has 40% or higher, preferably 50% or higher, more preferably 60% or higher, further preferably 70% or higher, still further preferably 80% or higher, even further preferably 90% or higher identity to the amino acid sequence of SLH domain-containing outer membrane protein 6 represented by any one of SEQ ID NOs: 1 to 3, and which has a function of binding to covalently linked sugar chain 3 of cell wall 4.

Cell wall-pyruvic acid modifying enzyme 9 may be, for example, Slr0688 when the parent cyanobacterium is the genus *Synechocystis*, may be Syn7502_03092 or Synpcc7942_1529, etc. when the parent cyanobacterium is the genus *Synechococcus*, may be ANA_C20348 or Anacy_1623, etc. when the parent cyanobacterium is the genus *Anabaena*, may be CsaB (NCBI accession ID: TRU80220), etc. when the parent cyanobacterium is the genus *Microcystis*, may be CsaB (NCBI accession ID: WP_107667006.1), etc. when the parent cyanobacterium is the genus *Cyanothece*, may be CsaB (NCBI accession ID: WP_026079530.1), etc. when the parent cyanobacterium is the genus *Spirulina*, may be CsaB (NCBI accession ID: WP_096658142.1), etc. when the parent cyanobacterium is the genus *Calothrix*, may be CsaB (NCBI accession ID: WP_099068528.1), etc. when the parent cyanobacterium is the genus *Nostoc*, may be CsaB (NCBI accession ID: WP_012361697.1), etc. when the parent cyanobacterium is the genus *Crocosphaera*, and may be CsaB (NCBI accession ID: WP_036798735), etc. when the parent cyanobacterium is the genus *Pleurocapsa*.

More specifically, cell wall-pyruvic acid modifying enzyme 9 may be, for example, Slr0688 (SEQ ID NO: 4) of *Synechocystis* sp. PCC 6803, Synpcc7942_1529 (SEQ ID NO: 5) of *Synechococcus* sp. PCC 7942, or Anacy_1623 (SEQ ID NO: 6) of *Anabaena cylindrica* PCC 7122. Alternatively, a protein having an amino acid sequence that is at least 50 percent identical to the amino acid sequence of any one of these cell wall-pyruvic acid modifying enzymes 9 may be used.

As a result, in modified cyanobacterium 31, for example, (a) the function of cell wall-pyruvic acid modifying enzyme 9 represented by any one of SEQ ID NOs: 4 to 6 or a protein having an amino acid sequence that is at least 50 percent identical to the amino acid sequence of any one of these cell wall-pyruvic acid modifying enzymes 9 is suppressed or lost, or (b) the expression of cell wall-pyruvic acid modifying enzyme 9 represented by any one of SEQ ID NOs: 4 to 6 or a protein having an amino acid sequence that is at least 50 percent identical to the amino acid sequence of any one of these cell wall-pyruvic acid modifying enzymes 9 is suppressed. Hence, in modified cyanobacterium 31, (a) the function of cell wall-pyruvic acid modifying enzyme 9 or a protein functionally equivalent to the enzyme is suppressed or lost, or (b) the expression level of cell wall-pyruvic acid modifying enzyme 9 or a protein functionally equivalent to the enzyme is decreased. Covalently linked sugar chain 3 on the surface of cell wall 4 is thereby less susceptible to modification with pyruvic acid, so that binding level and binding force of sugar chain 3 of cell wall 4 that binds to SLH domain 7 of SLH domain-containing outer membrane protein 6 in outer membrane 5 are reduced. As a result, in modified cyanobacterium 31, covalently linked sugar chain 3 on the surface of cell wall 4 is less susceptible to modification with pyruvic acid, so that binding force between cell wall 4 and outer membrane 5 is weakened. This facilitates partially detaching outer membrane 5 from cell wall 4. Thus, electron carrier 30 according to the present embodiment has improved efficiency of electron transfer with the outside.

As mentioned above, a protein having an amino acid sequence that is at least 30 percent identical to the amino acid sequence of a protein is reportedly likely to be functionally equivalent to the protein. Hence, cell wall-pyruvic acid modifying enzyme 9, the function of which is suppressed or lost may be, for example, a protein or a polypeptide which has an amino acid sequence that has 40% or higher, preferably 50% or higher, more preferably 60% or higher, further preferably 70% or higher, still further preferably 80% or higher, even further preferably 90% or higher identity to the amino acid sequence of cell wall-pyruvic acid modifying enzyme 9 represented by any one of SEQ ID NOs: 4 to 6, and which has a function of catalyzing reaction to modify covalently linked sugar chain 3 on peptidoglycan 2 of cell wall 4 with pyruvic acid.

In the present specification, the phrase "a function of SLH domain-containing outer membrane protein 6 is suppressed or lost" means that the ability of the protein to bind to cell wall 4 is suppressed or lost, the transport of the protein to outer membrane 5 is suppressed or lost, or the ability of the protein to be embedded so as to function in outer membrane 5 is suppressed or lost.

The phrase "a function of cell wall-pyruvic acid modifying enzyme 9 is suppressed or lost" means that the function of modifying covalently linked sugar chain 3 of cell wall 4 with pyruvic acid by the protein is suppressed or lost.

An approach for suppressing or losing the functions of these proteins is not particularly limited as long as the approach is usually used for suppressing or losing protein functions. The approach may involve, for example, deleting or inactivating a gene encoding SLH domain-containing outer membrane protein 6 and a gene encoding cell wall-pyruvic acid modifying enzyme 9, inhibiting the transcription of these genes, inhibiting the translation of transcripts of these genes, or administrating inhibitors which specifically inhibit these proteins.

In the present embodiment, in modified cyanobacterium 31 of the (i), a gene which causes expression of the protein involved in binding between outer membrane 5 and cell wall 4 may be deleted or inactivated.

As a result, in modified cyanobacterium 31 of the (i), the expression of the protein involved in the binding between cell wall 4 and outer membrane 5 is suppressed, or the function of the protein is suppressed or lost. Therefore, the binding (i.e., binding level and binding force) between cell wall 4 and outer membrane 5 is partially reduced. As a result, outer membrane 5 is easily detached from cell wall 4 at a site having the weakened binding between outer membrane 5 and cell wall 4. Modified cyanobacterium 31 of the (i) can thereby perform at least one of secreting intracellular electrons or electron-containing substance or molecule to the outside of the cell or taking electrons or an electron-containing substance or molecule from the outside of the cell into the cell. This improves extracellular electron transfer efficiency. Thus, electron carrier 30 according to the present embodiment has improved efficiency of electron transfer with the outside.

The gene which causes expression of the protein involved in binding between outer membrane 5 and cell wall 4 may be at least one of a gene encoding SLH domain-containing outer membrane protein 6 or a gene encoding cell wall-pyruvic acid modifying enzyme 9. In modified cyanobacterium 31, at least one of the gene encoding SLH domain-containing outer membrane protein 6 or the gene encoding cell wall-pyruvic acid modifying enzyme 9 is deleted or inactivated. Hence, in modified cyanobacterium 31, for example, (a) the expression of at least one of SLH domain-containing outer membrane protein 6 or cell wall-pyruvic acid modifying enzyme 9 is suppressed, or (b) the function of at least one of SLH domain-containing outer membrane protein 6 or cell wall-pyruvic acid modifying enzyme 9 is suppressed or lost. Hence, the binding (i.e., binding level and binding force) between SLH domain 7 of SLH domain-containing outer membrane protein 6 in outer membrane 5 and covalently linked sugar chain 3 on the surface of cell wall 4 is reduced. As a result, in modified cyanobacterium 31, outer membrane 5 is easily detached from cell wall 4 at a site having the weakened binding between outer membrane 5 and cell wall 4, so that intracellular electrons or electron-containing substance or molecule easily leaks out to the outside of the cell. Thus, electron carrier 30 according to the present embodiment has improved efficiency of electron transfer with the outside because in modified cyanobacterium 31, intracellular electrons or electron-containing substance or molecule easily leaks out to the outside of the cell.

In the present embodiment, for example, the transcription of at least one of the gene encoding SLH domain-containing outer membrane protein 6 or the gene encoding cell wall-pyruvic acid modifying enzyme 9 may be suppressed in order to suppress or lose the function of at least one of SLH domain-containing outer membrane protein 6 or cell wall-pyruvic acid modifying enzyme 9 in cyanobacterium.

The gene encoding SLH domain-containing outer membrane protein 6 may be, for example, slr1841, slr1908, or slr0042 when the parent cyanobacterium is the genus *Synechocystis*, may be nies970_09470, etc. in the case of the genus *Synechococcus*, may be anacy_5815 or anacy_3458, etc. when the parent cyanobacterium is the genus *Anabaena*, may be A0A0F6U6F8_MICAE, etc. when the parent cyanobacterium is the genus *Microcystis*, may be A0A3B8XX12_9CYAN, etc. when the parent cyanobacterium is the genus *Cyanothece*, may be A0A1Q8ZE23_9CYAN, etc. when the parent cyanobacterium is the genus *Leptolyngbya*, may be A0A1Z4R6U0_9CYAN, etc. when the parent cyanobacterium is the genus *Calothrix*, may be A0A1C0VG86_9NOSO, etc. when the parent cyanobacterium is the genus *Nostoc*, may be B1WRN6_CROS5, etc. when the parent cyanobacterium is the genus *Crocosphaera*, and may be K9TAE4_9CYAN, etc. when the parent cyanobacterium is the genus *Pleurocapsa*. The nucleotide sequences of these genes can be obtained from the NCBI database or Cyanobase mentioned above.

More specifically, the gene encoding SLH domain-containing outer membrane protein 6 may be slr1841 (SEQ ID NO: 7) of *Synechocystis* sp. PCC 6803, nies970_09470 (SEQ ID NO: 8) of *Synechococcus* sp. NIES-970, anacy_3458 (SEQ ID NO: 9) of *Anabaena cylindrica* PCC 7122, or a gene having a nucleotide sequence that is at least 50 percent identical to the nucleotide sequence of any one of these genes.

As a result, in modified cyanobacterium 31, the gene encoding SLH domain-containing outer membrane protein 6, represented by any one of SEQ ID NOs: 7 to 9 or a gene having a nucleotide sequence that is at least 50 percent identical to the nucleotide sequence of any one of these genes is deleted or inactivated. Hence, in modified cyanobacterium 31, (a) the expression of any one of SLH domain-containing outer membrane proteins 6 described above or a protein functionally equivalent to any one of these proteins is suppressed, or (b) the function of any one of SLH domain-containing outer membrane proteins 6 described above or a protein functionally equivalent to any one of these proteins is suppressed or lost. Hence, in modified cyanobacterium 31, the binding level and binding force of a cell wall 4 binding domain (e.g., SLH domain 7) of outer membrane 5 that binds to cell wall 4 are reduced. This facilitates partially detaching outer membrane 5 from cell wall 4, so that intracellular electron transfer substance 33 easily leaks out to the outside of the cell. Modified cyanobacterium 31 thereby has improved extracellular electron transfer efficiency. Thus, electron carrier 30 according to the present embodiment has improved efficiency of electron transfer with the outside.

As mentioned above, a protein having an amino acid sequence that is at least 30 percent identical to the amino acid sequence of a protein is reportedly likely to be functionally equivalent to the protein. Hence, a gene having a nucleotide sequence that is at least 30 percent identical to the nucleotide sequence of a gene encoding a protein is considered likely to cause expression of a protein functionally equivalent to the protein. Hence, the gene encoding SLH domain-containing outer membrane protein 6, the function of which is suppressed or lost may be, for example, a gene which has a nucleotide sequence that has 40% or higher, preferably 50% or higher, more preferably 60% or higher, further preferably 70% or higher, still further preferably 80% or higher, even further preferably 90% or higher identity to the nucleotide sequence of the gene encoding SLH domain-containing outer membrane protein 6 represented by any one of SEQ ID NOs: 7 to 9, and which encodes a protein or a polypeptide having a function of binding to covalently linked sugar chain 3 of cell wall 4.

The gene encoding cell wall-pyruvic acid modifying enzyme 9 may be, for example, slr0688 when the parent cyanobacterium is the genus *Synechocystis*, may be syn7502_03092 or synpcc7942_1529, etc. when the parent cyanobacterium is the genus *Synechococcus*, may be ana_C20348 or anacy_1623, etc. when the parent cyanobacterium is the genus *Anabaena*, may be csaB (NCBI accession ID: TRU80220), etc. when the parent cyanobacterium is the genus *Microcystis*, may be csaB (NCBI accession ID: WP_107667006.1), etc. when the parent cyanobacterium is the genus *Cyanothece*, may be csaB (NCBI accession ID:WP_026079530.1), etc. when the parent cyanobacterium is the genus *Spirulina*, may be csaB (NCBI accession ID:WP_096658142.1), etc. when the parent cyanobacterium is the genus *Calothrix*, may be csaB (NCBI accession ID:WP_099068528.1), etc. when the parent cyanobacterium is the genus *Nostoc*, may be csaB (NCBI accession ID: WP_012361697.1), etc. when the parent cyanobacterium is the genus *Crocosphaera*, and may be csaB (NCBI accession ID: WP_036798735), etc. when the parent cyanobacterium is the genus *Pleurocapsa*. The nucleotide sequences of these genes can be obtained from the NCBI database or Cyanobase mentioned above.

More specifically, the gene encoding cell wall-pyruvic acid modifying enzyme 9 may be slr0688 (SEQ ID NO: 10) of *Synechocystis* sp. PCC 6803, synpcc7942_1529 (SEQ ID NO: 11) of *Synechococcus* sp. PCC 7942, or anacy_1623 (SEQ ID NO: 12) of *Anabaena cylindrica* PCC 7122. Alternatively, a gene having a nucleotide sequence that is at least 50 percent identical to the nucleotide sequence of any one of these genes may be used.

As a result, in modified cyanobacterium 31, the gene encoding cell wall-pyruvic acid modifying enzyme 9, represented by any one of SEQ ID NOs: 10 to 12 or a gene having a nucleotide sequence that is at least 50 percent identical to the nucleotide sequence of any one of these enzyme-encoding genes is deleted or inactivated. Hence, in modified cyanobacterium 31, (a) the expression of any one of cell wall-pyruvic acid modifying enzymes 9 described above or a protein functionally equivalent to any one of these enzymes is suppressed, or (b) the function of any one of cell wall-pyruvic acid modifying enzymes 9 described above or a protein functionally equivalent to any one of these enzymes is suppressed or lost. Covalently linked sugar chain 3 on the surface of cell wall 4 is thereby less susceptible to modification with pyruvic acid, so that binding level and binding force of sugar chain 3 of cell wall 4 that binds to SLH domain 7 of SLH domain-containing outer membrane protein 6 in outer membrane 5 are reduced. As a result, in modified cyanobacterium 31, a decreased amount of covalently linked sugar chain 3 on the surface of cell wall 4 is modified with pyruvic acid, so that binding force between cell wall 4 and outer membrane 5 is weakened. This facilitates partially detaching outer membrane 5 from cell wall 4. As a result, in modified cyanobacterium 31, intracellular electrons or electron-containing substance or molecule easily leaks out to the outside of the cell. This improves extracellular electron transfer efficiency. Thus, electron carrier 30 according to the present embodiment has improved efficiency of electron transfer with the outside.

As mentioned above, a gene having a nucleotide sequence that is at least 30 percent identical to the nucleotide sequence of a gene encoding a protein is considered likely to cause expression of a protein functionally equivalent to the protein. Hence, the gene encoding cell wall-pyruvic acid modifying enzyme 9, the function of which is suppressed or lost may be, for example, a gene which has a nucleotide sequence that has 40% or higher, preferably 50% or higher, more preferably 60% or higher, further preferably 70% or higher, still further preferably 80% or higher, even further preferably 90% or higher identity to the nucleotide sequence of the gene encoding cell wall-pyruvic acid modifying enzyme 9 represented by any one of SEQ ID NOs: 10 to 12, and which encodes a protein or a polypeptide having a function of catalyzing reaction to modify covalently linked sugar chain 3 on peptidoglycan 2 of cell wall 4 with pyruvic acid.

Subsequently, modified cyanobacterium 31 of the (ii) will be described.

In modified cyanobacterium 31 of the (ii), organic channel protein 18 which improves protein permeability of outer membrane 5 is expressed.

In this context, the phrase "cause expression of organic channel protein 18 in outer membrane 5 of cyanobacterium" means that a gene encoding organic channel protein 18 is inserted to chromosomal DNA or a plasmid of cyanobacterium, and organic channel protein 18 synthesized through transcription and translation of the gene is transported to outer membrane 5 and exerts a channel function of selectively allowing protein to permeate outer membrane 5 of cyanobacterium. Approaches for the insertion and expression of the gene are not particularly limited and are not limited by the nucleotide sequence of a promoter for transcriptional activation and a ribosomal binding sequence for translation as well as the type of a signal sequence for transport to outer membrane 5 as long as the approaches are usually used.

In the present embodiment, organic channel protein 18 to be expressed in outer membrane 5 of cyanobacterium may be a chloroplast-derived outer membrane channel protein. This organic channel protein 18 may be, for example, CppS (SEQ ID NO: 13) or CppF (SEQ ID NO: 14) of a glaucophyte *Cyanophora paradoxa* (hereinafter, also referred to as *C. paradoxa*). Alternatively, organic channel protein 18 may be a protein having an amino acid sequence that is at least 50 percent identical to the amino acid sequence of CppS or CppF. The protein having an amino acid sequence that is at least 50 percent identical to the amino acid sequence of CppS or CppF is not limited to a chloroplast-derived protein and may be, for example, a microbe (e.g., a bacterium)-derived analogous protein of CppS or CppF.

As a result, in modified cyanobacterium 31 of the (ii), CppS (SEQ ID NO: 13) or CppF (SEQ ID NO: 14) serving as organic channel protein 18 which improves protein permeability of outer membrane 5, or a protein functionally equivalent to any one of these organic channel proteins 18 is expressed. Hence, in modified cyanobacterium 31 of the (ii), the protein permeability of outer membrane 5 is improved, so that the material permeability of outer membrane 5 is improved. As a result, modified cyanobacterium 31 of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, electron carrier 30 according to the present embodiment has improved efficiency of electron transfer with the outside.

In general, a protein having an amino acid sequence that is at least 30 percent identical to the amino acid sequence of a protein has high conformational homology to the protein and therefore, is reportedly likely to be functionally equivalent to the protein. Hence, organic channel protein 18 may be, for example, a protein or a polypeptide which has an amino acid sequence that has 40% or higher, preferably 50% or higher, more preferably 60% or higher, further preferably 70% or higher, still further preferably 80% or higher, even further preferably 90% or higher identity to the amino acid sequence of the protein represented by any one of SEQ ID NO: 13 and SEQ ID NO: 14, and which has a function of improving protein permeability of outer membrane 5.

In the present embodiment, in modified cyanobacterium 31 of the (ii), a gene encoding organic channel protein 18 which improves protein permeability of outer membrane 5 may have been introduced. Hence, in modified cyanobacterium 31 of the (ii), organic channel protein 18 which improves protein permeability of outer membrane 5 is expressed. Hence, in modified cyanobacterium 31 of the (ii), the protein permeability of outer membrane 5 is improved, so that the material permeability of outer membrane 5 is improved. As a result, modified cyanobacterium 31 of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, electron carrier 30 according to the present embodiment has improved efficiency of electron transfer with the outside.

The gene may be, for example, a chloroplast-derived gene. The chloroplast-derived gene encoding organic channel protein 18 may be, for example, cppS (SEQ ID NO: 15) or cppF (SEQ ID NO: 16) of a glaucophytes *Cyanophora paradoxa*. The gene of organic channel protein 18 may have a nucleotide sequence that is at least 50 percent identical to the nucleotide sequence of any one of these genes. As a result, in modified cyanobacterium 31 of the (ii), the gene encoding organic channel protein 18, represented by any one of SEQ ID NO: 15 and SEQ ID NO: 16 or a gene having a nucleotide sequence that is 50 percent identical to the nucleotide sequence of any one of these genes is introduced. Hence, in modified cyanobacterium 31 of the (ii), the protein having the function of improving the protein permeability of outer membrane 5 or a protein functionally equivalent to the protein is expressed. As a result, in modified cyanobacterium 31 of the (ii), the protein permeability of outer membrane 5 is improved, so that the material permeability of outer membrane 5 is improved. As a result, modified cyanobacterium 31 of the (ii) can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, electron carrier 30 according to the present embodiment has improved efficiency of electron transfer with the outside.

The gene encoding organic channel protein 18 is not limited to a chloroplast-derived gene. The gene encoding organic channel protein 18 may be, for example, a gene which has a nucleotide sequence that has 40% or higher, preferably 50% or higher, more preferably 60% or higher, further preferably 70% or higher, still further preferably 80% or higher, even further preferably 90% or higher identity to the nucleotide sequence of any of the genes cppS (SEQ ID NO: 15) and cppF (SEQ ID NO: 16), and which encodes a protein or a polypeptide having a function of improving the protein permeability of outer membrane 5.

4. Electron Carrier Production Method

Subsequently, a production method for electron carrier 30 according to the present embodiment will be described. The production method of electron carrier 30 comprises producing modified cyanobacterium 31 in which at least: (i) a function of a protein involved in binding between outer membrane 5 and cell wall 4 of cyanobacterium is suppressed or lost; or (ii) organic channel protein 18 which improves protein permeability of outer membrane 5 is expressed (hereinafter, referred to as the producing of modified cyanobacterium 31).

Hereinafter, the producing of modified cyanobacterium 31 will be described. The producing of modified cyanobacterium 31 comprises at least one of (i) suppressing or losing a function of protein involved in binding between outer membrane 5 and cell wall 4 of cyanobacterium or (ii) expressing organic channel protein 18 which improves protein permeability of outer membrane 5.

In the (i), the protein involved in binding between outer membrane 5 and cell wall 4 may be, for example, at least one of SLH domain-containing outer membrane protein 6 or cell wall-pyruvic acid modifying enzyme 9.

An approach for suppressing or losing the function of the protein is not particularly limited and may involve, for example, deleting or inactivating a gene encoding SLH domain-containing outer membrane protein 6 and a gene encoding cell wall-pyruvic acid modifying enzyme 9, inhibiting the transcription of these genes, inhibiting the translation of transcripts of these genes, or administrating inhibitors which specifically inhibit these proteins.

An approach for deleting or inactivating the gene may be, for example, the mutagenesis of one or more bases on the nucleotide sequence of the gene, the substitution of the nucleotide sequence by another nucleotide sequence, the insertion of another nucleotide sequence thereto, or the partial or complete deletion of the nucleotide sequence of the gene.

An approach for inhibiting the transcription of the gene may be, for example, the mutagenesis of a promoter region of the gene, the inactivation of the promoter by substitution by another nucleotide sequence or insertion of another nucleotide sequence, or CRISPR interference (NPL 16: Yao et al., ACS Synth. Biol., 2016, 5: 207-212). A specific approach for the mutagenesis or the substitution by or insertion of a nucleotide sequence may be, for example, ultraviolet irradiation, site-directed mutagenesis, or homologous recombination.

An approach for inhibiting the translation of a transcript of the gene may be, for example, RNA (ribonucleic acid) interference.

The function of the protein involved in binding between outer membrane 5 and cell wall 4 of cyanobacterium may be suppressed or lost to produce modified cyanobacterium 31 by use of any one of the above approaches. As a result, in modified cyanobacterium 31 produced by the (i), the binding (i.e., binding level and binding force) between cell wall 4 and outer membrane 5 is partially reduced, so that outer membrane 5 is easy to partially detach from cell wall 4. Hence, in modified cyanobacterium 31, intracellular electrons or electron-containing substance or molecule easily leaks out to the outside of the cell. This improves extracellular electron transfer efficiency.

In the (ii), organic channel protein 18 which improves protein permeability of outer membrane 5 is, for example, a chloroplast-derived channel protein and, specifically, may be CppS having the amino acid sequence represented by SEQ ID NO: 13 or CppF having the amino acid sequence represented by SEQ ID NO: 14. Alternatively, organic channel protein 18 may be a protein having an amino acid sequence that is at least 50 percent identical to the amino acid sequence of any one of these channel proteins.

In the expressing of organic channel protein 18, first, a gene encoding organic channel protein 18 which improves protein permeability of outer membrane 5 is inserted to chromosomal DNA or a plasmid of cyanobacterium. Then, organic channel protein 18 synthesized through transcription and translation of the gene is transported to outer membrane 5 and exerts a channel function in outer membrane 5 of cyanobacterium. Approaches for the insertion and expression of the gene are not particularly limited and are not limited by the nucleotide sequence of a promoter for transcriptional activation and a ribosomal binding sequence for translation as well as the type of a signal sequence for transport to outer membrane 5 as long as the approaches are usually used.

In this way, organic channel protein 18 which improves protein permeability of outer membrane 5 may be expressed to produce modified cyanobacterium 31. As a result, in modified cyanobacterium 31 produced by the (ii), the protein permeability of outer membrane 5 is improved, so that the material permeability of outer membrane 5 is improved. As a result, modified cyanobacterium 31 can perform at least one of secreting intracellular electrons or electron-containing substance or molecule to the outside of the cell or taking electrons or an electron-containing substance or molecule from the outside of the cell into the cell. This improves extracellular electron transfer efficiency.

These procedures may produce modified cyanobacterium 31 in which at least: (i) a function of a protein involved in binding between outer membrane 5 and cell wall 4 of cyanobacterium is suppressed or lost; or (ii) organic channel protein 18 which improves protein permeability of outer membrane 5 is expressed.

As a result, modified cyanobacterium 31 produced by the method can perform at least one of secreting intracellular electrons or electron-containing substance or molecule to the outside of the cell or taking electrons or an electron-containing substance or molecule from the outside of the cell into the cell. This improves extracellular electron transfer efficiency. Thus, the production method for electron carrier 30 according to the present embodiment can provide electron carrier 30 having improved efficiency of electron transfer with the outside.

5. Electron Transfer Method

The electron transfer method according to the present embodiment uses electron carrier 30 comprising any modified cyanobacterium 31 described above.

Electron carrier 30 comprises modified cyanobacterium 31 described above in which at least: (i) a function of a protein involved in binding between outer membrane 5 and cell wall 4 of cyanobacterium is suppressed or lost; and (ii) organic channel protein 18 which improves protein permeability of outer membrane 5 is expressed, and this modified cyanobacterium 31 performs at least one of (I) supplying electrons to an outside or (II) taking in electrons from the outside.

As mentioned above, the present embodiment, the electrons are electrons or an electron-containing substance or molecule. The phrase "supplying electrons" refers to not only supplying electrons but supplying every substance or molecule having electrons. The phrase "taking in electrons" refers to not only taking in electrons but taking in every substance or molecule having electrons.

Electron carrier 30 may be modified cyanobacterium 31 of at least one of the (i) or the (ii) and, as illustrated in FIG. 2, may comprise at least one of electron transfer substance 33, electron mediator 35, or conductive substance 37, in addition to this modified cyanobacterium 31.

First, the case of (I) supplying electrons to an outside will be described. The phrase "supplying electrons to an outside" by modified cyanobacterium 31 means that, for example, modified cyanobacterium 31 generates an electron or an electron-containing substance or molecule under light. The electron-containing substance or molecule may be, for example, electron transfer substance 33.

Modified cyanobacterium 31 may release the generated electron or electron-containing substance or molecule to the outside of the outer membrane. Modified cyanobacterium 31 may release, for example, a portion of electron transfer substance 33 involved in a photosynthetic electron transfer chain to the outside of the cell (i.e., the outside of outer membrane 5). Electron transfer substance 33 released to the outside of the cell may be taken up into another modified cyanobacterium 31, for example, and thereby involved in the generation of a bioenergy source, or may cause electron migration via a plurality of other modified cyanobacteria 31. Then, electron transfer substance 33 released may supply electrons to electrodes through redox reaction with the outside (e.g., external electrodes). The electron migration can be confirmed by measuring a current value. For example, modified cyanobacterium 31 is cultured, and electrodes are placed in a cell suspension (i.e., a culture solution), followed by the application of potential from the outside. As a result, current is generated because electron transfer occurs with high efficiency between the cell and the electrodes.

Subsequently, the case of (II) taking in electrons from the outside will be described. The phrase "taking in electrons from the outside" by modified cyanobacterium 31 means that, for example, modified cyanobacterium 31 takes an electron or an electron-containing substance or molecule present outside the outer membrane into an inside of cell wall 4. Further, modified cyanobacterium 31 may use an electron or an electron-containing substance or molecule inside cell wall 4 (inside the cytoplasm). As described in Background Art, in general, cyanobacterium has high photosynthetic ability and intracellularly produces various organic materials. Modified cyanobacterium 31 also intracellularly (inside the cell wall and inside the thylakoid) produces various organic materials, as in cyanobacterium. In this respect, modified cyanobacterium 31 may take an electron or an electron-containing substance or molecule (which may be a portion of electron transfer substance 33) present outside outer membrane 5 into an inside of cell wall 4, receive the electron from electron transfer substance 33 inside cell wall 4 (i.e., in the cytoplasm), and use it in bio-manufacturing. Further, modified cyanobacterium 31 may use the electron taken in from the outside in respiration (catabolism of organic substances). Thus, modified cyanobacterium 31 can use electric energy instead of light energy and is therefore less likely to lack intracellular reducing power even in an environment insufficiently irradiated with sunlight. Hence, modified cyanobacterium 31 can exploit both light energy and electric energy and therefore has improved efficiency of intracellular bio-manufacturing.

For example, modified cyanobacterium 31 contained in electron carrier 30 can stably perform generation of necessary intracellular energy and reducing power, material catabolism, and bio-manufacturing by using electric energy instead of light energy.

Thus, electron carrier 30 according to the present embodiment comprising modified cyanobacterium 31 having improved extracellular electron transfer efficiency can efficiently supply electrons to the outside (e.g., external electrodes) and efficiently receive electrons from the outside. Hence, for example, use of electron carrier 30 enables current to be generated through modified cyanobacterium 31 contained in electron carrier 30, which releases an intracellular electron transfer substance to the outside of the cell and thereby efficiently supplies electrons, for example, to external electrodes.

WORKING EXAMPLES

Hereinafter, the electron carrier, the electron carrier production method, and the electron transfer method of the present disclosure will be specifically described with reference to working examples. However, the present disclosure is not limited by the following working examples by any means.

In the following working examples, modified cyanobacteria having a cell wall from which the outer membrane of cyanobacterium was partially detached were prepared by (i) suppressing or losing a function of a protein involved in binding between an outer membrane and a cell wall of cyanobacterium (Example 1 and Example 2), and a modified cyanobacterium having improved material permeability of outer membrane was prepared by (ii) expressing a channel protein which improved protein permeability of the outer membrane (Example 3). These 3 types of modified cyanobacteria were evaluated for whether or not to perform at least one of supplying electrons to an outside by secreting intracellular electron transfer substance 33, or taking electrons from the outside of the cell into the cell, i.e., whether or not to improve efficiency of extracellular electron transfer between the cell and external electrodes. The evaluation was conducted by the quantification and identification of proteins secreted by these modified cyanobacteria to the outside of the cells as well as the measurement of intracellular current values generated through photosynthesis.

The cyanobacterium species used in the present working examples is *Synechocystis* sp. PCC 6803 (hereinafter, simply referred to as "cyanobacterium").

Working Example 1

In Example 1, a modified cyanobacterium was produced in which the expression of slr1841 gene (SEQ ID NO: 7) encoding a SLH domain-containing outer membrane protein was suppressed.

(1) Construction of Modified Cyanobacterium Strain in which Expression of Slr1841 Gene was Suppressed The gene suppression method used was CRISPR (Clustered Regularly Interspaced Short Palindromic Repeat) interference. In this method, the expression of the slr1841 gene (SEQ ID NO: 7) can be suppressed by introducing a gene encoding dCas9 protein (hereinafter, referred to as dCas9 gene) and slr1841_sgRNA (single-guide ribonucleic acid) gene to the chromosomal DNA of cyanobacterium.

The mechanism of the suppression of gene expression by this method is as follows.

First, nuclease activity-deficient Cas9 protein (dCas9) and sgRNA (slr1841_sgRNA) complementarily binding to the nucleotide sequence of the slr1841 gene (SEQ ID NO: 7) forms a complex.

Next, this complex recognizes the slr1841 gene on the chromosomal DNA of cyanobacterium and specifically binds to the slr1841 gene. This binding, which serves as steric hindrance, inhibits the transcription of the slr1841 gene. As a result, the expression of the slr1841 gene in the cyanobacterium is suppressed.

Hereinafter, a method for introducing each of the two genes described above to the chromosomal DNA of cyanobacterium will be specifically described.

(1-1) Introduction of dCas9 Gene

The dCas9 gene, operator gene for the expression control of the dCas9 gene, and spectinomycin resistance marker gene serving as an indicator for gene introduction were amplified by PCR (polymerase chain reaction) with the chromosomal DNA of a *Synechocystis* LY07 strain (hereinafter, also referred to as an LY07 strain) (see NPL 16) as a template using the primers psbA1-Fw (SEQ ID NO: 17) and psbA1-Rv (SEQ ID NO: 18) described in Table 1. In the LY07 strain, these three genes are inserted in a linked state in psbA1 gene on the chromosomal DNA and can therefore be amplified as one DNA fragment by PCR. Here, the obtained DNA fragment is referred to as a "psbA1::dCas9 cassette". The psbA1::dCas9 cassette was inserted to a pUC19 plasmid by use of In-Fusion PCR Cloning® to obtain a pUC19-dCas9 plasmid.

TABLE 1

| Primer name | Nucleotide sequence | SEQ ID NO |
|---|---|---|
| psbA1-Fw | 5'-CAGTGAATTGGAGGTC GGTATATAGCGTTGCAGTC GCTGG-3' | 17 |
| psbA1-Rv | 5'-GATTACGCCAAGCTTGC ATGACCGCGGTCACTTCATA ACC-3' | 18 |
| slr2030-Fw | 5'-CAGTGAATTCGAGCTCG GTAATAACCGTTGTCCCTTT TGTTTCATCG-3' | 19 |
| sgRNA_ slr1841-Rv | 5'-TGTTAGTGAGCGCTGCT GTTAGCTCCCAGTATCTCTA TCACTGAT-3' | 20 |
| sgRNA_ slr1841-Fw | 5'-ACAGCAGGGCTCACTAA CAGTTTTAGAGCTAGAAATA GCAAGTTAAAATAA-3' | 21 |
| slr2031-Rv | 5'-GATTACGCCAAGCTTGC ATGGGGAACAAGCTGAATCT GGGCATC-3' | 22 |
| sgRNA_ slr0688-Rv | 5'-TTTTAGTCTGTTTGCTG CATAGCTCCCAGTATCTCTA TCACTGAT-3' | 23 |
| sgRNA_ slr0688-Fw | 5'-TGCAGCAAACAGACTAA AAGTTTTAGAGCTAGAAATA GCAAGTTAAAATAA-3' | 24 |
| slr0042-Fw | 5'-TAGATATAATGTGTGGT TAAAATGAGGAATTCATCGC A-3' | 25 |
| slr0042-Rv | 5'-CGCTCTTCCGATCTGAT TTAAAATGTGAACGTCGTCC GTAG-3' | 26 |
| PL22-Rv | 5'-TGTTAGTGAGCCCTGCT GTTAGCTCCCAGTATCTCTA TCACTGAT-3' | 27 |
| KmR-Fw | 5'-ACAGCAGGGCTCACTAA CAGTTTTAGAGCTAGAAATA GCAAGTTAAAATAA-3' | 28 |
| CppS-Fw | 5'-TCCCTGGTTCCGCTGGG GCTATGGCCCCGGAGTGCAC CGT-3' | 29 |
| CppS-Rv | 5'-ATTTGATGCCTGGCTCT AGTTTACAGAAGCTCGATCT CGA-3' | 30 |
| TetR-Rv | 5'-TAGCAGGTACTGCAAAC GCTATGCCGCTCCCGGTGTT CGC-3' | 31 |

TABLE 1 -continued

| Primer name | Nucleotide sequence | SEQ ID NO |
|---|---|---|
| TetR-Fw | 5'-TTAGAACTGGTAAACGAT ACTTACTGATCGATAACGAGC G-3' | 32 |

1 μg of the obtained pUC19-dCas9 plasmid and a cyanobacterium culture solution (bacterial cell concentration OD730=approximately 0.5) were mixed, and the pUC19-dCas9 plasmid was introduced into the cyanobacterium cells by spontaneous transformation. The transformed cells were selected by growth on a BG-11 agar medium containing 20 μg/mL spectinomycin. In the selected cells, homologous recombination occurred between the psbA1 gene on the chromosomal DNA and the upstream and downstream fragment regions of psbA1 on the pUC19-dCas9 plasmid. In this way, a *Synechocystis* dCas9 strain having the insert of the dCas9 cassette in the psbA1 gene region was obtained. The compositon of the BG-11 medium used is as described in Table 2.

TABLE 2

| Component | Content (mg/L) |
|---|---|
| EDTA-Na | 1 |
| Ammonium Iron Citrate | 6 |
| $NaNO_3$ | 1500 |
| $MgSO_4$ | 75 |
| $K_2HPO_4$ | 39 |
| $CaCl_2$ | 28.6 |
| $H_3BO_4$ | 2.8 |
| $MnCl_2$ | 1.8 |
| $ZnSO_4$ | 0.2 |
| $CuSO_4$ | 0.08 |
| $Na_2MoO_4$ | 0.02 |
| $Co(NO_3)_2$ | 0.005 |
| TES-KOH (pH 7.5) | 4580 |

(1-2) Introduction of Slr1841_sgRNA Gene

In the CRISPR interference, sgRNA specifically binds to a target gene by introducing a sequence of approximately 20 bases complementary to the target sequence to a region called protospacer on the sgRNA gene. The protospacer sequence used in the present working examples is described in Table 3.

TABLE 3

| Protospacer target gene | Nucleotide sequence | SEQ ID NO |
|---|---|---|
| slr1841 | 5'-ACAGCAGGGCTCACTAACA-3' | 33 |
| slr0688 | 5'-TGCAGCAAACAGACTAAAA-3' | 34 |

In the *Synechocystis* LY07 strain, the sgRNA gene (except for the protospacer region) and kanamycin resistance marker gene are inserted in a linked state in slr2030-slr2031 genes on the chromosomal DNA. Thus, sgRNA that specifically recognizes slr1841 (slr1841_sgRNA) can be easily obtained by adding a protospacer sequence (SEQ ID NO: 33) complementary to the slr1841 gene (SEQ ID NO: 7) to primers for use in amplifying the sgRNA gene by PCR.

First, two DNA fragments were amplified by PCR with the chromosomal DNA of the LY07 strain as a template using a set of the primers slr2030-Fw (SEQ ID NO: 19) and sgRNA_slr1841-Rv (SEQ ID NO: 20) and a set of the primers sgRNA_slr1841-Fw (SEQ ID NO: 21) and slr2031-Rv (SEQ ID NO: 22) descried in Table 1.

Subsequently, a DNA fragment (slr2030-2031::slr1841_sgRNA) having (i) the slr2030 gene fragment, (ii) slr1841_sgRNA, (iii) kanamycin resistance marker gene, and (iv) the slr2031 gene fragment linked in order was obtained by PCR amplification with a mixed solution of the DNA fragments described above as a template using the primers slr2030-Fw (SEQ ID NO: 19) and slr2031-Rv (SEQ ID NO: 22) described in Table 1. The slr2030-2031::slr1841_sgRNA was inserted to a pUC19 plasmid by use of In-Fusion PCR Cloning® to obtain a pUC19-slr1841_sgRNA plasmid.

The pUC19-slr1841_sgRNA plasmid was introduced to the *Synechocystis* dCas9 strain in the same manner as in the (1-1), and the transformed cells were selected on a BG-11 agar medium containing 30 μg/mL kanamycin. In this way, a transformant *Synechocystis* dCas9 slr1841_sgRNA strain having the insert of slr1841_sgRNA in the slr2030-slr2031 gene on the chromosomal DNA (hereinafter, also referred to as a slr1841-suppressed strain) was obtained.

(1-3) Suppression of Slr1841 Gene

The promoter sequences of the dCas9 gene and the slr1841_sgRNA gene were designed such that expression was induced in the presence of anhydrotetracycline (aTc). In the present working examples, the expression of the slr1841 gene was suppressed by adding aTc (final concentration: 1 μg/mL) into the medium.

Working Example 2

In Example 2, a modified cyanobacterium in which the expression of slr0688 gene encoding a cell wall-pyruvic acid modifying enzyme was suppressed was obtained by the following procedures.

(2) Construction of Modified Cyanobacterium Strain in which Expression of Slr0688 Gene was Suppressed sgRNA gene containing a protospacer sequence (SEQ ID NO: 34) complementary to the slr0688 gene (SEQ ID NO: 10) was introduced to the *Synechocystis* dCas9 strain by the same procedures as in the (1-2) to obtain a *Synechocystis* dCas9 slr0688_sgRNA strain. The same conditions as in the (1-2) were used except that a set of the primers slr2030-Fw (SEQ ID NO: 19) and sgRNA_slr0688-Rv (SEQ ID NO: 23) and a set of the primers sgRNA_slr0688-Fw (SEQ ID NO: 24) and slr2031-Rv (SEQ ID NO: 22) described in Table 1 were used; and a DNA fragment (slr2030-2031::slr0688_sgRNA) having (i) the slr2030 gene fragment, (ii) slr0688_sgRNA, (iii) kanamycin resistance marker gene, and (iv) the slr2031 gene fragment linked in order was inserted to a pUC19 plasmid by use of In-Fusion PCR Cloning® to obtain a pUC19-slr0688_sgRNA plasmid.

Further, the expression of the slr0688 gene was suppressed by the same procedures as in the (1-3).

Comparative Example 1

In Comparative Example 1, the *Synechocystis* dCas9 strain was obtained by the same procedures as in (1-1) of Example 1.

Subsequently, the state of cell surface was observed as to each of the bacterial strains obtained in Example 1, Example 2 and Comparative Example 1. Hereinafter, the details will be described.

(3) Observation of State of Cell Surface of Bacterial Strain

The respective ultrathin sections of the modified cyanobacterium *Synechocystis* dCas9 slr1841_sgRNA strain (i.e., a slr1841-suppressed strain) obtained in Example 1, the modified cyanobacterium *Synechocystis* dCas9 slr0688_sgRNA strain (hereinafter, also referred to as a slr0688-suppressed strain) obtained in Example 2, and the modified cyanobacterium *Synechocystis* dCas9 strain (hereinafter, referred to as a control strain) obtained in Comparative Example 1 were prepared, and the state of cell surface (in other words, an outer membrane structure) was observed under an electron microscope.

(3-1) Culture of Bacterial Strain

The slr1841-suppressed strain of Example 1 was inoculated at initial bacterial cell concentration OD730=0.05 to a BG-11 medium containing 1 μg/mL aTc and shake-cultured for 5 days under conditions of a light quantity of 100 μmol/m2/s and 30° C. The slr0688-suppressed strain of Example 2 and the control strain of Comparative Example 1 were also cultured under the same conditions as in Example 1.

(3-2) Preparation of Ultrathin Section of Bacterial Strain

The culture solution obtained in the (3-1) was centrifuged at 2,500 g at room temperature for 10 minutes to retrieve the cells of the slr1841-suppressed strain of Example 1. Subsequently, the cells were rapidly frozen with liquid propane of −175° C. and then fixed at −80° C. for 2 days using an ethanol solution containing 2% glutaraldehyde and 1% tannic acid. The cells thus fixed were dehydrated with ethanol, and the dehydrated cells were impregnated with propylene oxide and then immersed in a resin (Quetol-651) solution. Then, the resin was cured by still standing at 60° C. for 48 hours to embed the cells in the resin. The cells in the resin were sliced into a thickness of 70 nm using an ultramicrotome (Ultracut) to prepare an ultrathin section. This ultrathin section was stained using 2% uranium acetate and 1% lead citrate solutions to provide a transmission electron microscopy sample of the slr1841-suppressed strain of Example 1. The slr0688-suppressed strain of Example 2 and the control strain of Comparative Example 1 were also each subjected to the same operation as above to provide transmission electron microscopy samples.

(3-3) Observation Under Electron Microscope

The ultrathin sections obtained in the (3-2) were observed under an accelerating voltage of 100 kV using a transmission electron microscope (JEOL JEM-1400Plus). The observation results are shown in FIGS. 3 to 8.

Figure 3:
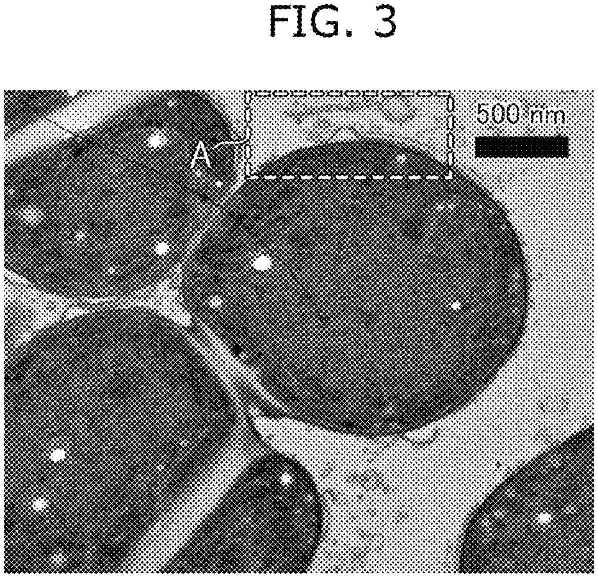
FIG. 3 is a transmission electron microscope observation image of an ultrathin section of a modified cyanobacterium of Example 1.
Figure 4:
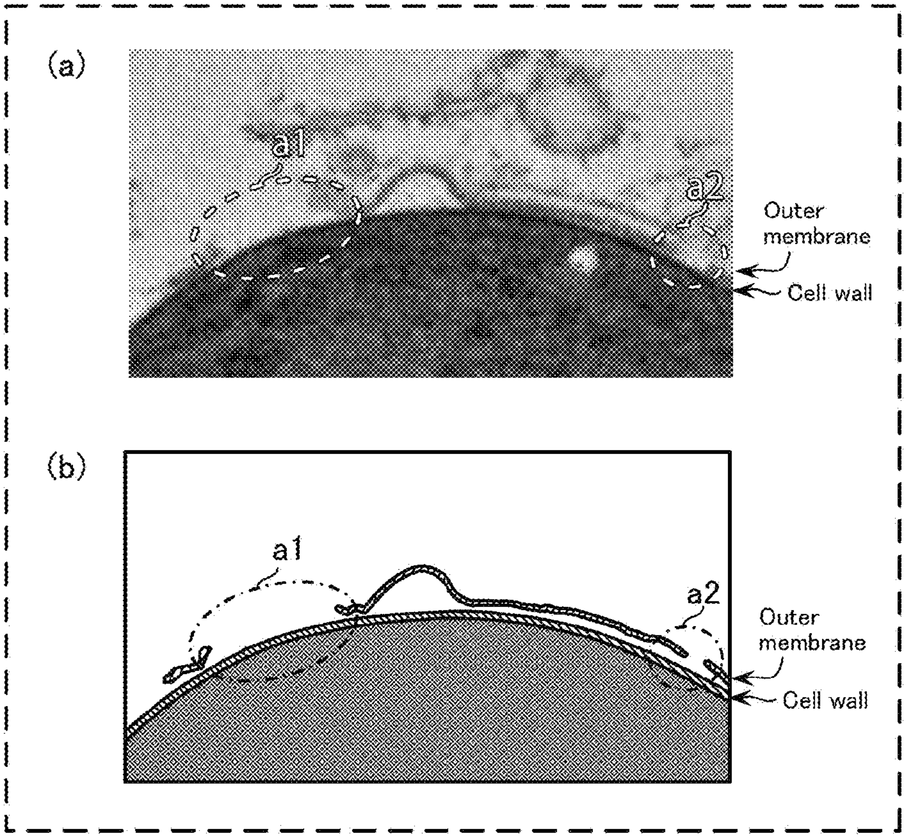
FIG. 4 is an enlarged image of broken line region A of FIG. 3.

First, the slr1841-suppressed strain of Example 1 will be described. FIG. 3 is a TEM (transmission electron microscope) image of the slr1841-suppressed strain of Example 1. FIG. 4 is an enlarged image of broken line region A of FIG. 3. (a) in FIG. 4 is an enlarged TEM image of broken line region A of FIG. 3, and (b) in FIG. 4 is a diagram graphically depicting the enlarged TEM image of (a) in FIG. 4.

As illustrated in FIG. 3, in the slr1841-suppressed strain of Example 1, the outer membrane was partially stripped (i.e., the outer membrane partially came off) from the cell wall while the outer membrane became partially loose.

In order to confirm the more detailed state of cell surface, broken line region A was subjected to magnifying observation. As a result, as illustrated in (a) and (b) of FIG. 4, sites where the outer membrane partially came off (dot-dash line regions a1 and a2 in the figures) were able to be confirmed. Also, a site where the outer membrane became largely loose was able to be confirmed near dot-dash line region at. This site is a site having weakened binding between the outer membrane and the cell wall. It is considered that the outer membrane swelled outward and became loose because the culture solution infiltrated into the periplasm from the outer membrane.

Figure 5:
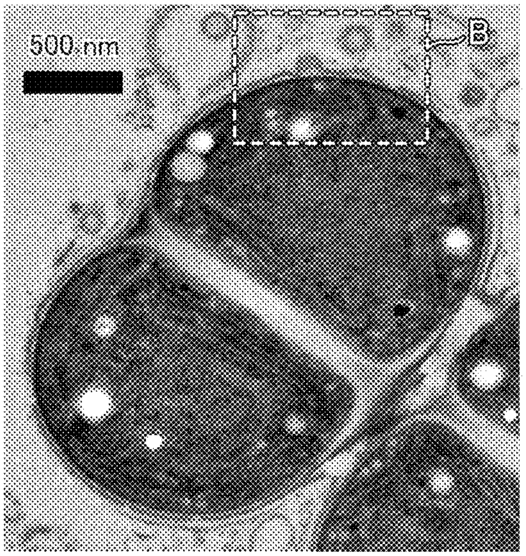
FIG. 5 is a transmission electron microscope image of an ultrathin section of a modified cyanobacterium of Example 2.
Figure 6:
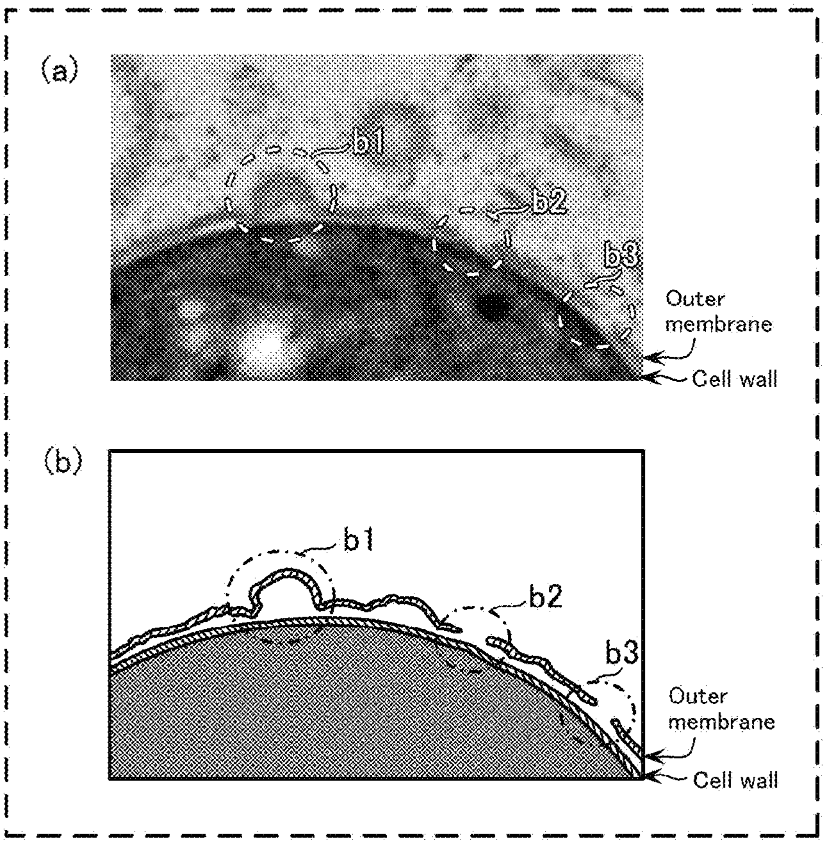
FIG. 6 is an enlarged image of broken line region B of FIG. 5.

Subsequently, the slr0688-suppressed strain of Example 2 will be described. FIG. 5 is a TEM image of the slr0688-suppressed strain of Example 2. FIG. 6 is an enlarged image of broken line region B of FIG. 5. (a) in FIG. 6 is an enlarged TEM image of broken line region B of FIG. 5, and (b) in FIG. 6 is a diagram graphically depicting the enlarged TEM image of (a) in FIG. 6.

As illustrated in FIG. 5, in the slr0688-suppressed strain of Example 2, the outer membrane was partially stripped from the cell wall while the outer membrane partially became loose. In the slr0688-suppressed strain, it was able to be confirmed that the outer membrane was partially detached from the cell wall.

In order to confirm the more detailed state of cell surface, broken line region B was subjected to magnifying observation. As a result, as illustrated in (a) and (b) in FIG. 6, a site where the outer membrane became largely loose (dot-dash line region b1 in the figures) and sites where the outer membrane partially came off (dot-dash line regions b2 and b3 in the figures) were able to be confirmed. Also, a site where the outer membrane was detached from the cell wall was able to be confirmed near each of dot-dash line regions b1, b2, and b3.

Figure 7:
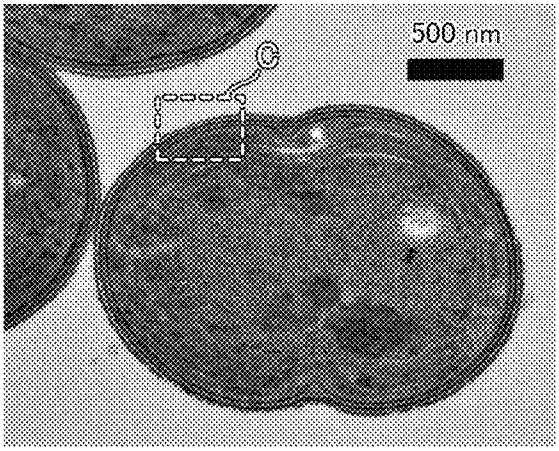
FIG. 7 is a transmission electron microscope image of an ultrathin section of a modified cyanobacterium of Comparative Example 1.
Figure 8:
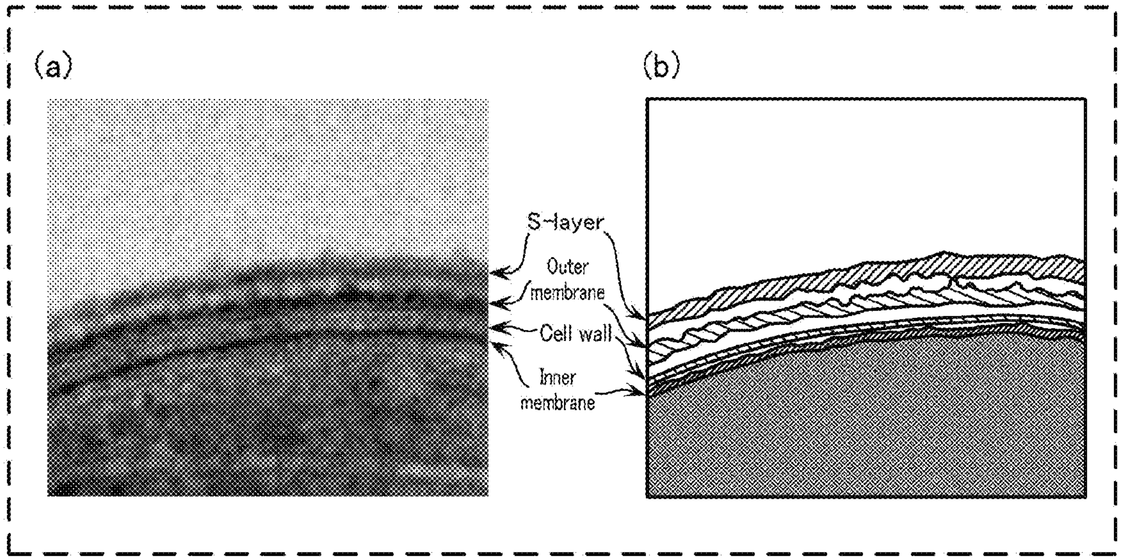
FIG. 8 is an enlarged view of broken line region C of FIG. 7.

Subsequently, the control strain of Comparative Example 1 will be described. FIG. 7 is a TEM image of the control strain of Comparative Example 1. FIG. 8 is an enlarged image of broken line region C of FIG. 7. (a) in FIG. 8 is an enlarged TEM image of broken line region C of FIG. 7, and (b) in FIG. 8 is a diagram graphically depicting the enlarged TEM image of (a) in FIG. 8.

As illustrated in FIG. 7, the control strain of Comparative Example 1 had ordered cell surface where the inner membrane, the cell wall, the outer membrane, and the S-layer were kept in a state layered in order. Specifically, the control strain exhibited none of the site where the outer membrane was detached from the cell wall, the site where the outer membrane was stripped (i.e., came off) from the cell wall, and the site where the outer membrane became loose, which were found in Examples 1 and 2.

Working Example 3

In Example 3, a *Synechocystis* cppS tetR strain in which a chloroplast outer membrane channel protein CppS (SEQ ID NO: 13) retained by a glaucophyte *Cyanophora paradoxa* was introduced to the outer membrane of cyanobacterium (hereinafter, also referred to as cppS-introduced strain) was obtained by the following procedures.

(4) Introduction of Chloroplast Outer Membrane Channel Protein CppS to Cyanobacterium Outer Membrane (4-1) Construction of cppS gene expression cassette A gene cassette in which the cppS gene, a promoter region (PL22) for the expression control of the cppS gene, an outer membrane localization signal sequence (slr0042-signal) for cyanobacterium, and kanamycin resistance marker gene (KmR) serving as an indicator for gene introduction were linked was prepared by the following procedures.

First, the slr0042 gene was obtained by PCR amplification with the chromosomal DNA of cyanobacterium as a template using the primers slr0042-Fw (SEQ ID NO: 25) and slr0042-Rv (SEQ ID NO: 26) described in Table 1. Subsequently, PL22 and KmR were obtained by PCR amplification with the chromosomal DNA of a *Synechocystis* LY07 strain (NPL 16) as a template using a set of the primers slr2030-Fw (SEQ ID NO: 19) and PL22-Rv (SEQ ID NO: 27) and a set of the primers KmR-Fw (SEQ ID NO: 28) and slr2031-Rv (SEQ ID NO: 22) described in Table 1. Since the LY07 strain has these inserted in slr2030-slr2031 genes on the chromosomes, a form having the slr2030 gene fragment linked on the 5'-terminal side of PL22 and a form having the slr2031 gene fragment linked on the 3'-terminal side of KmR were amplified by PCR amplification using the four primers described above. Subsequently, a gene cassette (slr2030-2031::slr0042-KmR cassette) having the slr2030 gene fragment, PL22, the slr0042 gene, KmR, and the slr2031 gene fragment linked in order from the 5'-terminal side was obtained by PCR amplification with a mixed solution of the slr0042 gene, PL22, and KmR obtained by the procedures as a template using four primers (SEQ ID NOs: 19, 22, 27, and 28) described in Table 1. The slr2030-2031::slr0042-KmR cassette was inserted to a pUC19 plasmid by use of In-Fusion PCR Cloning® to obtain a pUC19-slr0042 plasmid.

In tandem with the procedures described above, total cDNA was prepared from a glaucophyte *C. paradoxa* NIES-547 using SMART cDNA Library Synthesis Kit (Clontech Laboratories, Inc.). The cppS gene (SEQ ID NO: 13) was obtained by PCR amplification with this cDNA as a template using the primers cppS-Fw (SEQ ID NO: 29) and cppS-Rv (SEQ ID NO: 30) described in Table 1. The cppS gene (SEQ ID NO: 13) was inserted to a pUC19-slr0042 plasmid by use of In-Fusion PCR Cloning® to obtain a pUC19-CppS plasmid. By this procedure, the cppS gene was inserted in a form linked on the 3'-terminal side of the outer membrane localization signal sequence of the slr0042 gene, and the region of the slr0042 gene except for the outer membrane localization signal sequence was removed by exchange with the coding region of cppS.

(4-2) Construction of promoter activity control cassette (tetR) of PL22

The promoter activity of the PL22 is induced only in the presence of anhydrotetracycline (aTc) by control mediated by TetR repressor. Thus, the tetR gene for PL22 activity control needs to be introduced to the modified cyanobacterium.

First, the tetR gene and spectinomycin resistance marker gene (SpcR) serving as an indicator for gene introduction were obtained by PCR amplification with the chromosomal DNA of the LY07 strain as a template using a set of the primers psbA1-Fw (SEQ ID NO: 17) and tetR-Rv (SEQ ID NO: 31) and a set of the primers tetR-Fw (SEQ ID NO: 32) and psbA1-Rv (SEQ ID NO: 18) described in Table 1. Since the LYO7 strain has these inserted in psbA1 gene on the chromosomes, a form having the upstream fragment of the psbA1 gene linked on the 5'-terminal side of the tetR gene and a form having the downstream fragment of the psbA1 gene linked on the 3'-terminal side of SpcR were amplified by PCR amplification using the four primers described above. Subsequently, a gene cassette (psbA1::tetR cassette) having the psbA1 gene upstream fragment, tetR, SpcR, and the psbA1 gene downstream fragment linked in order from the 5'-terminal side was obtained by PCR amplification with a mixed solution of the tetR gene and SpcR as a template using the primers psbA1-Fw (SEQ ID NO: 17) and psbA1-Rv (SEQ ID NO: 18) described in Table 1. The psbA1::tetR cassette was inserted to a pUC19 plasmid by use of In-Fusion PCR Cloning® to obtain a pUC19-tetR plasmid.

(4-3) Insertion of cppS gene expression cassette and tetR cassette

1 μg of the pUC19-cppS plasmid obtained by the procedures described above and a cyanobacterium culture solution (bacterial cell concentration OD730=approximately 0.5) were mixed, and the plasmid was introduced into the cells by spontaneous transformation. The transformed cells were selected by growth on a BG-11 agar medium containing 30 μg/mL of kanamycin. In the selected cells, homologous recombination occurred between the slr2030-2031 genes on the chromosomes and the slr2030 and slr2031 gene fragment regions of psbA1 on the pUC19-cppS plasmid. In this way, a *Synechocystis* cppS strain having the insert of the cppS gene expression cassette in the slr2030-2031 gene region was obtained. The composition of the BG-11 medium used is as described in Table 2.

Subsequently, 1 μg of the pUC19-tetR plasmid and a *Synechocystis* cppS culture solution (bacterial cell concentration OD730=approximately 0.5) were mixed, and the plasmid was introduced into the cells by spontaneous transformation. The transformed cells were selected by growth on a BG-11 agar medium containing 30 μg/mL of kanamycin and 20 μg/mL spectinomycin to obtain a *Synechocystis* cppS tetR strain. As described above, this strain had the insert of the tetR cassette in the psbA1 gene on the chromosomal DNA.

(4-4) Induction of cppS gene expression

The cppS gene expression of the *Synechocystis* cppS tetR strain is induced in the presence of anhydrotetracycline (aTc). In the present working examples, the expression of the cppS gene was induced by culture in a BG-11 medium supplemented with aTc (final concentration: 1 μg/mL).

(5) Secretory productivity test of protein

Whether or not protein present in the periplasm (space between the outer membrane and the inner membrane) was secreted to the outside of the cells was confirmed by the following method.

More specifically, the slr1841-suppressed strain of Example 1, the slr0688-suppressed strain of Example 2, the cppS-introduced strain of Example 3, and the control strain of Comparative Example 1 were each cultured, and the amount of protein secreted to the outside of the cells (hereinafter, also referred to as the amount of secretory protein) was measured. Each of the bacterial strains described above was evaluated for the secretory productivity of protein from the amount of protein in the culture solution. The secretory productivity of protein refers to the ability to produce protein by secreting intracellularly produced protein to the outside of the cells. Hereinafter, a specific method will be described.

(5-1) Culture of bacterial strain

The slr1841-suppressed strain of Example 1 was cultured in the same manner as in the (3-1). The culture was performed three independent times. The bacterial strains of Example 2, Example 3, and Comparative Example 1 were also cultured under the same conditions as in the bacterial strain of Example 1.

(5-2) Quantification of protein secreted to outside of cell

Each culture solution obtained in the (5-1) was centrifuged at 2,500 g at room temperature for 10 minutes to obtain a culture supernatant. The obtained culture supernatant was filtered through a membrane filter having a pore size of 0.22 μm to completely remove the cells of the slr1841-suppressed strain of Example 1. The amount of total protein contained in the culture supernatant thus filtered was quantified by the BCA (bicinchoninic acid) method. This series of operations was performed as to each of the three culture solutions obtained by culture performed three independent times to determine a mean and standard deviation of the amounts of protein secreted to the outside of the cells of the slr1841-suppressed strain of Example 1. The amounts of protein in the three culture solutions obtained in the (5-1) were also quantified under the same conditions as above as to each of the bacterial strains of Example 2, Example 3, and Comparative Example 1, and a mean and standard deviation of the amounts of protein in the three culture solutions was determined.

Figure 9:
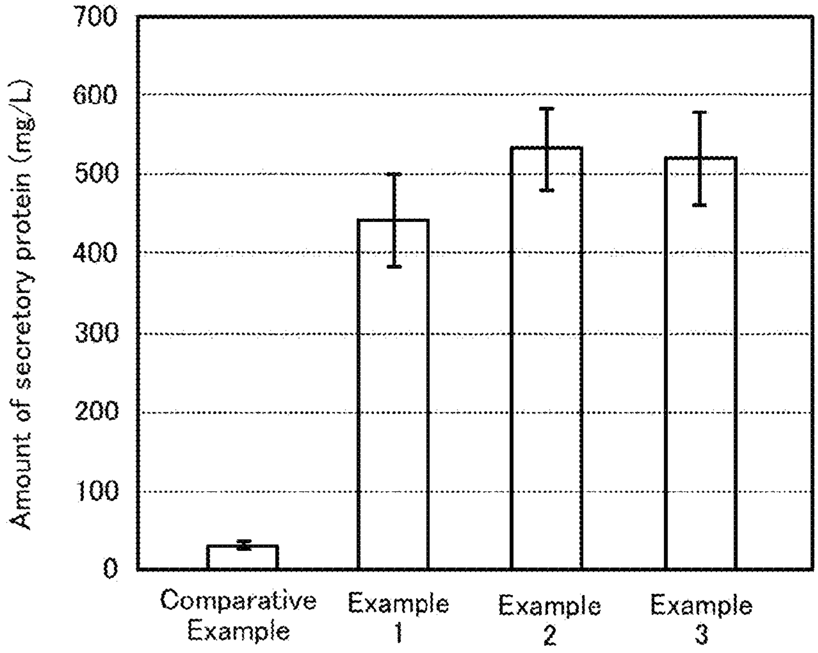
FIG. 9 is a graph illustrating the amount of protein (n=3, error bar=SD) in the culture supernatant of a modified cyanobacterium in Example 1, Example 2, Example 3, and Comparative Example 1.

The results are shown in FIG. 9. FIG. 9 is a graph illustrating the amount of protein (n=3, error bar=SD) in the culture supernatant of a modified cyanobacterium in Examples 1 to 3 and Comparative Example 1.

As illustrated in FIG. 9, the amount (mg/L) of protein secreted into the culture supernatant was improved by approximately 25 times in all the slr1841-suppressed strain of Example 1, the slr0688-suppressed strain of Example 2, and the cppS-introduced strain of Example 3 compared with the control strain of Comparative Example 1.

Although the description of data is omitted, the absorbance (730 nm) of the culture solution was measured and the amount of secretory protein per g of bacterial cell dry weight (mg protein/g cell dry weight) was calculated. As a result, the amount of secretory protein per g of bacterial cell dry weight (mg protein/g cell dry weight) was improved by approximately 36 times in all the slr1841-suppressed strain of Example 1, the slr0688-suppressed strain of Example 2, and the cppS-introduced strain of Example 3 compared with the control strain of Comparative Example 1.

When the amount of secretory protein (mg/L) in FIG. 9 was compared between the "modified cyanobacteria in which the outer membrane of cyanobacterium was partially detached from the cell wall" of Example 1 and Example 2, the amount of protein secreted into the culture supernatant was larger for the slr0688-suppressed strain of Example 2 in which the expression of the gene encoding the cell wall-pyruvic acid modifying enzyme (slr0688) was suppressed than for the slr1841-suppressed strain of Example 1 in which the expression of the gene encoding the SLH domain-containing outer membrane protein (slr1841) was suppressed. This is probably related to a larger number of covalently linked sugar chains on cell wall surface than the number of the SLH domain-containing outer membrane protein (Slr1841) in the outer membrane. Specifically, the amount of protein secreted was increased from that for the slr1841-suppressed strain of Example 1 probably because the slr0688-suppressed strain of Example 2 had smaller binding level and binding force between the outer membrane and the cell wall than those of the slr1841-suppressed strain of Example 1.

When the amount of secretory protein (mg/L) in FIG. 9 was compared between the slr0688-suppressed strain of Example 2 and the cppS-introduced strain of Example 3 in which the gene (cppS) encoding the organic channel protein CppS was expressed in the outer membrane of cyanobacterium, the amount of secretory protein (mg/L) was slightly larger (approximately 20 mg/L) for the slr0688-suppressed strain of Example 2 than for the cppS-introduced strain of Example 3.

From these results, it was able to be confirmed that a function of a protein related to binding between an outer membrane and a cell wall is suppressed, whereby the binding between the outer membrane and the cell wall of cyanobacterium is partially weakened so that the outer membrane is partially detached from the cell wall. It was also able to be confirmed that the weakened binding between the outer membrane and the cell wall facilitates secreting intracellularly produced protein of cyanobacterium to the outside of the cell. Thus, the modified cyanobacterium according to the present disclosure was found to largely improve the secretory productivity of protein.

(5-3) Identification of secreted protein

Subsequently, the protein contained in the culture supernatant obtained in the (5-2) was identified by LC-MS/MS. A method will be described below.

(5-3-1) Sample preparation

Cold acetone was added in an amount of 8 times the fluid volume of the culture supernatant, and the mixture was left standing at 20° C. for 2 hours and then centrifuged at 20,000 g for 15 minutes to obtain a precipitate of the protein. To this precipitate, 100 mM Tris pH 8.5 and 0.5% sodium dodecanoate (SDoD) were added, and the protein was lysed with a closed sonicator. After adjustment of the protein concentration to 1 μg/mL, dithiothreitol (DTT) (final concentration: 10 mM) was added thereto, and the mixture was left standing at 50° C. for 30 minutes. Subsequently, iodoacetamide (IAA) (final concentration: 30 mM) was added thereto, and the mixture was left standing at room temperature (in the dark) for 30 minutes. In order to terminate the reaction of IAA, cysteine (final concentration: 60 mM) was added thereto, and the mixture was left standing at room temperature for 10 minutes. 400 ng of trypsin was added thereto, and the mixture was left standing overnight at 37° C. to convert the protein to peptide fragments. After addition of 5% TFA (trifluoroacetic acid), the mixture was centrifuged at 15,000 g at room temperature for 10 minutes to obtain a supernatant. By this operation, SDoD was removed. The sample was desalted using a C18 spin column and then dried with a centrifugal evaporator. Then, 3% acetonitrile and 0.1% formic acid were added thereto, and the sample was lysed using a closed sonicator. The peptide concentration was adjusted to 200 ng/μL.

(5-3-2) LC-MS/MS analysis

The sample obtained in the (5-3-1) was analyzed using an LC-MS/MS apparatus (UltiMate 3000 RSLCnano LC System) under the following conditions.

Amount of sample injected: 200 ng

Column: CAPCELL CORE MP 75 μm×250 mm

Solvent: solvent A: 0.1% aqueous formic acid solution, solvent B: 0.1% formic acid+80% acetonitrile Gradient program: 8% solvent B 4 minutes after sample injection, 44% solvent B 27 minutes later, 80% solvent B 28 minutes later, and completion of measurement 34 minutes later.

(5-3-3) Data analysis

The obtained data was analyzed under the following conditions to perform protein and peptide identification and the calculation of quantification values.

Software: Scaffold DIA

Database: UniProtKB/Swiss Prot database (*Synechocystis* sp. PCC 6803)

Fragmentation: HCD

Precursor Tolerance: 8 ppm

Fragment Tolerance: 10 ppm

Data Acquisition Type: Overlapping DIA

Peptide Length: 8-70

Peptide Charge: 2-8

Max Missed Cleavages: 1

Fixed Modification: Carbamidomethylation

Peptide FDR: 1% or less

Among the identified proteins, 10 types of proteins are described in Table 4 in the descending order of relative quantification values from the largest one.

TABLE 4

| | Protein name | Uniprot Accession ID | Gene name |
|---|---|---|---|
| 1 | Carboxyl-terminal protease | P73458 | prc |
| 2 | Sll0314 protein | Q55648 | sll0314 |
| 3 | Sll0470 protein | Q55847 | sll0470 |
| 4 | Ssr1853 protein | P72639 | ssr1853 |
| 5 | Sll0319 protein | P74789 | sll0319 |
| 6 | Slr0581 protein | Q55408 | slr0581 |
| 7 | Carbon dioxide-concentrating mechanism | P72761 | ccmK2 |
| 8 | protein CcmK homolog 2 | Q55386 | slr0924 |
| 9 | Slr0924 protein | Q59991 | slr0042 |
| 10 | Slr0042 protein | P73817 | sll1951 |

All the 10 types of proteins were contained in each of the culture supernatants of Example 1 to Example 3. All of these proteins retained a periplasm (which refers to the space between the outer membrane and the inner membrane) localization signal. From these results, it was able to be confirmed that in the slr1841-suppressed strain of Example 1 and the slr0688-suppressed strain of Example 2, the outer membrane is partially detached from the cell wall, whereby protein in the periplasm easily leaks out to the outside of the outer membrane (i.e., to the outside of the bacterial cell), because the binding between the outer membrane and the cell wall is weakened. It was also able to be confirmed that in the cppS-introduced strain of Example 3, the protein permeability of the outer membrane is improved by the expression of the cppS gene so that protein in the periplasm easily permeates the channel protein CppS and leaks out to the outside of the outer membrane (i.e., to the outside of the bacterial cell). Thus, the modified strains of Examples 1 to 3 were found to have improved material permeability of the outer membrane.

(6) Evaluation of extracellular electron transfer efficiency of modified cyanobacterium The slr0688-suppressed strain of Example 2, the cppS-introduced strain of Example 3, and the control strain of Comparative Example 1 were evaluated for their extracellular electron transfer efficiency. More specifically, the culture solutions of these modified strains were each irradiated with light, and intracellular current generated by the splitting of water through photosynthesis was detected in external electrodes to evaluate the extracellular electron transfer efficiency. The apparatus used and procedures of measuring current will be described below.

(6-1) Electrochemical measurement device

Figure 10:
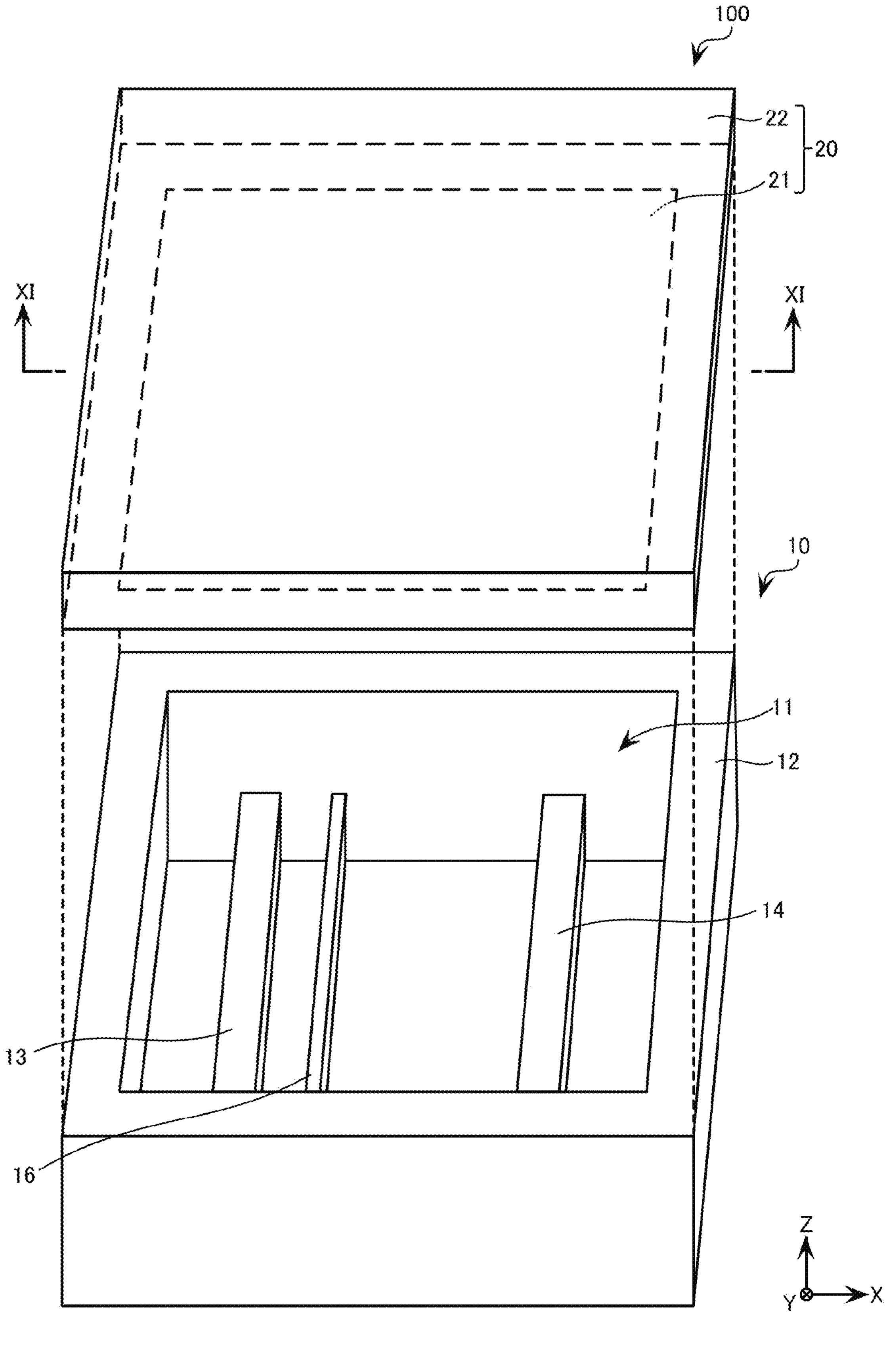
FIG. 10 is an exploded perspective view diagrammatically illustrating the configuration of an electrochemical measurement device.
Figure 11:
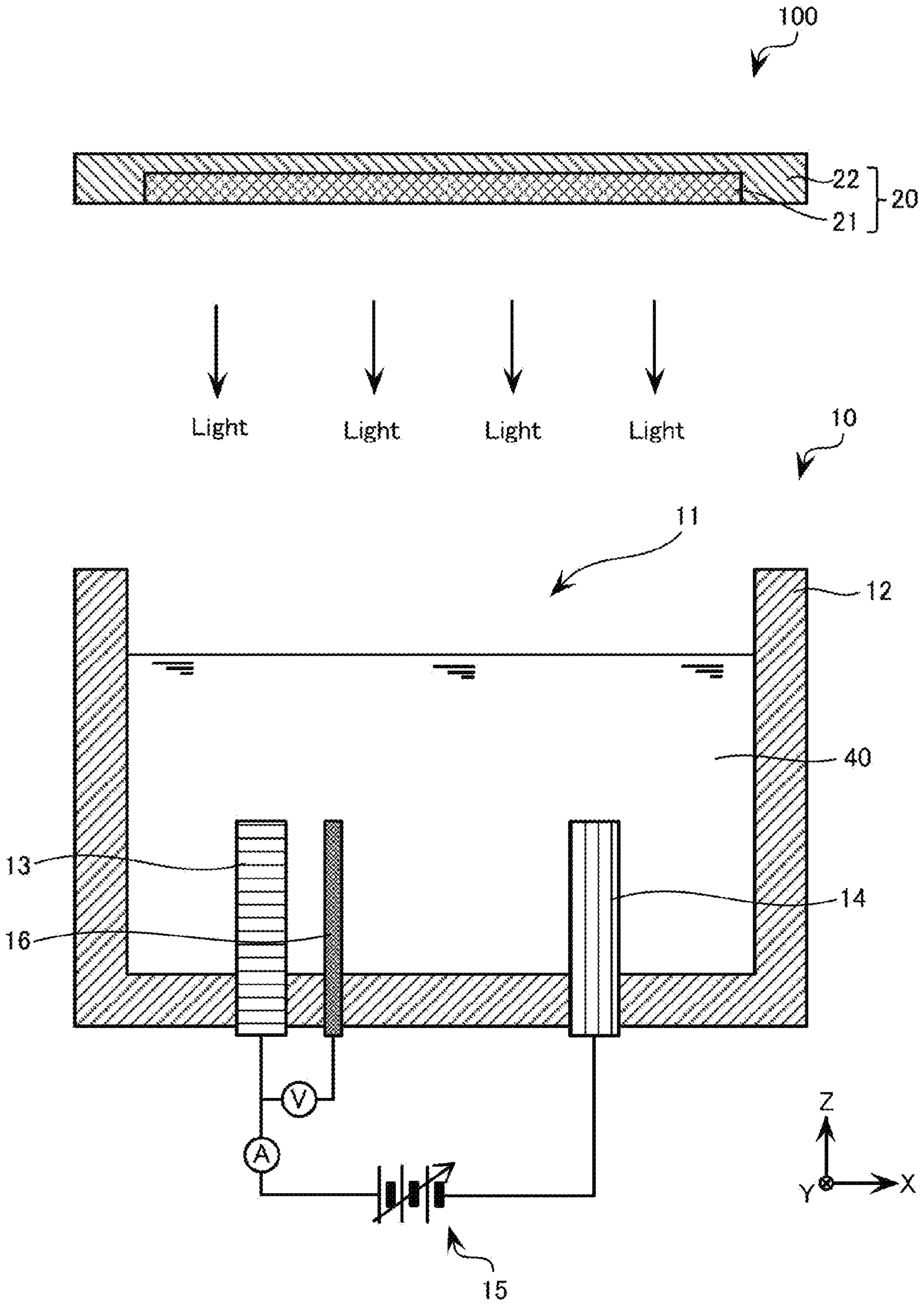
FIG. 11 is a diagrammatic cross-sectional view taken along the XI-XI line of FIG. 10.

First, the configuration of electrochemical measurement device 100 will be described with reference to the drawings. FIG. 10 is an exploded perspective view diagrammatically illustrating one example of the configuration of electrochemical measurement device 100. FIG. 11 is a diagrammatic cross-sectional view taken along the XI-XI line of FIG. 10.

As illustrated in FIGS. 10 and 11, electrochemical measurement device 100 has measurer 10 and light emitter 20. Measurer 10 has: reaction chamber 12 having container portion 11 for containing culture solution 40 of cyanobacterium; first electrode 13 installed in contact with culture solution 40 in container portion 11, inside reaction chamber 12; second electrode 14 installed in contact with culture solution 40 in container portion 11, inside reaction chamber 12; potentiostat 15 for controlling the potential of first electrode 13; and reference electrode 16 installed in contact with culture solution 40 in container portion 11, inside reaction chamber 12.

Reaction chamber 12 has electric isolation and does not permit permeation of culture solution 40. Reaction chamber 12 may be constituted by a material that resists corrosion or break by culture solution 40, for example, plastic or ceramic.

Measurer 10, for example, applies voltage or injects current to between first electrode 13 and second electrode 14 and measures current or potential corresponding to the voltage or the current. Here, measurer 10 applies voltage to between first electrode 13 and second electrode 14 and measures current.

First electrode 13 is a so-called working electrode and is an electrode that sensitively makes an electrochemical response to a trace substance in culture solution 40 on the electrode surface. Second electrode 14 is a so-called opposite electrode and is an electrode for establishing potential difference from the working electrode (first electrode 13) or injecting current.

First electrode 13 and second electrode 14 are each constituted by a conductive substance. The conductive substance may be, for example, a carbon material, a conductive polymer material, a semiconductor, or a metal. The carbon material may be, for example, a carbon nanotube, ketjen black, glassy carbon, graphene, fullerene, carbon fiber, a carbon fabric, or carbon aerogel. The conductive polymer material may be, for example, polyaniline, polyacetylene, polypyrrole, poly(3,4-ethylenedioxythiophene), poly(p-phenylenevinylene), polythiophene, or poly(p-phenylene sulfide). The semiconductor may be, for example, silicone, germanium, indium tin oxide (ITO), titanium oxide, copper oxide, or silver oxide. The metal may be, for example, gold, platinum, silver, titanium, aluminum, tungsten, copper, iron, or palladium. Here, first electrode 13 is an indium tin oxide (ITO) electrode, and second electrode 14 is a platinum electrode. The conductive substance is not particularly limited as long as the conductive substance is not degraded through its own oxidation reaction.

Reference electrode 16 is an electrode that maintains constant potential without reacting with a substance in culture solution 40, and is used for keeping potential difference constant between first electrode 13 and reference electrode 16 by potentiostat 15. Here, reference electrode 16 is a silver/silver chloride electrode.

Potentiostat 15 applies voltage to between first electrode 13 and second electrode 14 and controls the potential between first electrode 13 and reference electrode 16 to a predetermined value.

Light emitter 20 has light source 21 and housing 22 which retains light source 21. Although the illustration of the detailed configuration is omitted, light source 21 has, for example, one or two or more luminants (e.g., LED (light emitting diode)) and a reflective surface which surrounds the luminant. Light emitter 20 may be disposed a predetermined distance away from measurer 10 in the plus direction of the Z axis.

FIG. 11 illustrates first electrode 13, second electrode 14, and reference electrode 16 each configured to have an extraction electrode beneath reaction chamber 12 (i.e., in the minus direction of the Z axis). A form that does not protrude from reaction chamber 12 may be used as long as electric connection with potentiostat 15 is attained. Alternatively, first electrode 13, second electrode 14, and reference electrode 16 may each be in a form led out of the side of reaction chamber 12.

(6-2) Measurement of current

As for the control strain of Comparative Example 1, the slr0688-suppressed strain of Example 2, and the cppS-introduced strain of Example 3, the amount of current generated from each of these three bacterial strains was measured by the following procedures.

The configuration of electrochemical measurement device 100 used is as follows.

First electrode 13: Indium tin oxide electrode (surface area: 3.14 $cm^2$)

Second electrode 14: Platinum electrode

Reference electrode 16: silver/silver chloride electrode

Light source 21: Light source that emits white light of approximately 120 $\mu mol/m^2/s$ (6-2-1) Provision of culture solution First, the control strain of Comparative Example 1 was inoculated at initial bacterial cell concentration OD730=0.1 to a BG-11 medium containing 1 μg/mL aTc and shake-cultured for 3 days under conditions of a light quantity of 100 $\mu mol/m^2/s$ and 30° C. The slr0688-suppressed strain of Example 2 and the cppS-introduced strain of Example 3 were also each cultured under the same conditions as above.

Figure 12:
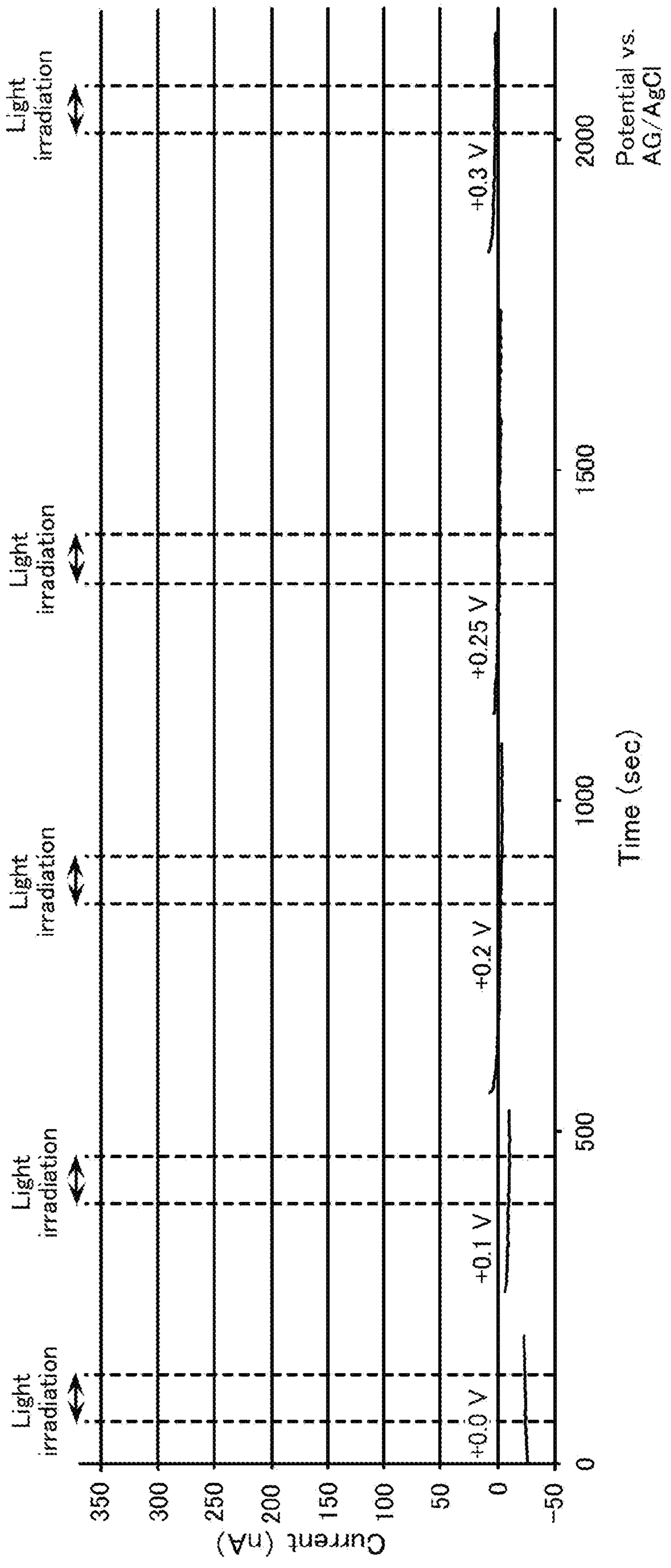
FIG. 12 is a diagram illustrating results of measuring current that flows when the culture solution of the modified cyanobacterium of Comparative Example 1 is irradiated with light.

(6-2-2) Measurement of current 4 mL of culture solution 40 of the control strain of Comparative Example 1 obtained in the (6-2-1) was injected to reaction chamber 12. Then, the potential of first electrode 13 based on reference electrode 16 was controlled to +0.0 V by potentiostat 15. Then, culture solution 40 in container portion 11 was irradiated with white light of approximately 120 $\mu mol/m^2/s$ for a given time from light emitter 20, and current flowing between first electrode 13 and second electrode 14 was measured. Subsequently, the potential of first electrode 13 based on reference electrode 16 was changed to +0.1 V, +0.2 V, +0.25 V, and +0.3 V in order, and current flowing between first electrode 13 and second electrode 14 was also measured at each potential controlled. The results are shown in FIG. 12. FIG. 12 is a diagram illustrating the results of measuring current that flowed when culture solution 40 of the control strain of Comparative Example 1 was irradiated with light.

As illustrated in FIG. 12, the current values (maximum values after baseline correction) measured when the potential of first electrode 13 based on reference electrode 16 was +0.0 V, +0.1 V, +0.2 V, +0.25 V, and +0.3 V were approximately +0.0 nA, approximately +0.0 nA, approximately +0.0 nA, approximately +0.0 nA, and approximately +1.0 nA, respectively, in culture solution 40 of the control strain of Comparative Example 1.

Figure 13:
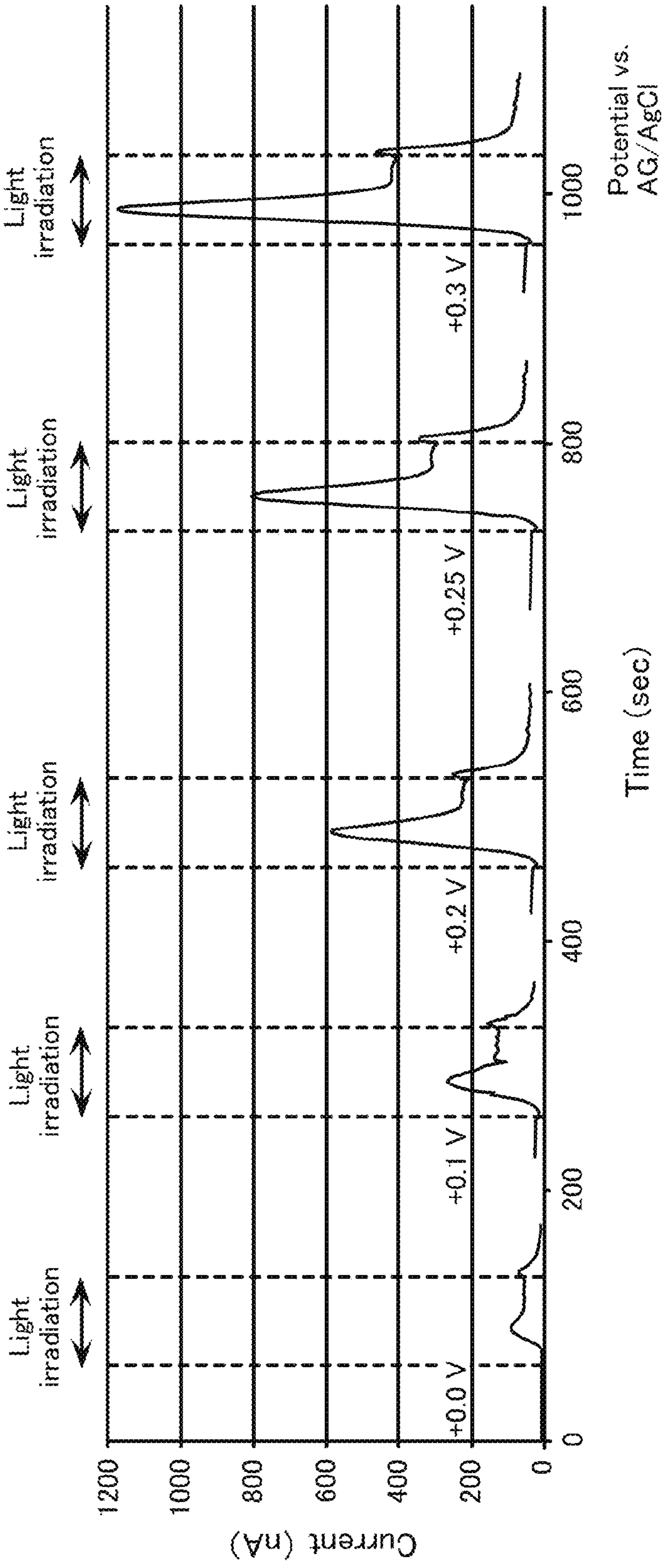
FIG. 13 is a diagram illustrating results of measuring current that flows when the culture solution of the modified cyanobacterium of Example 2 is irradiated with light.
Figure 14:
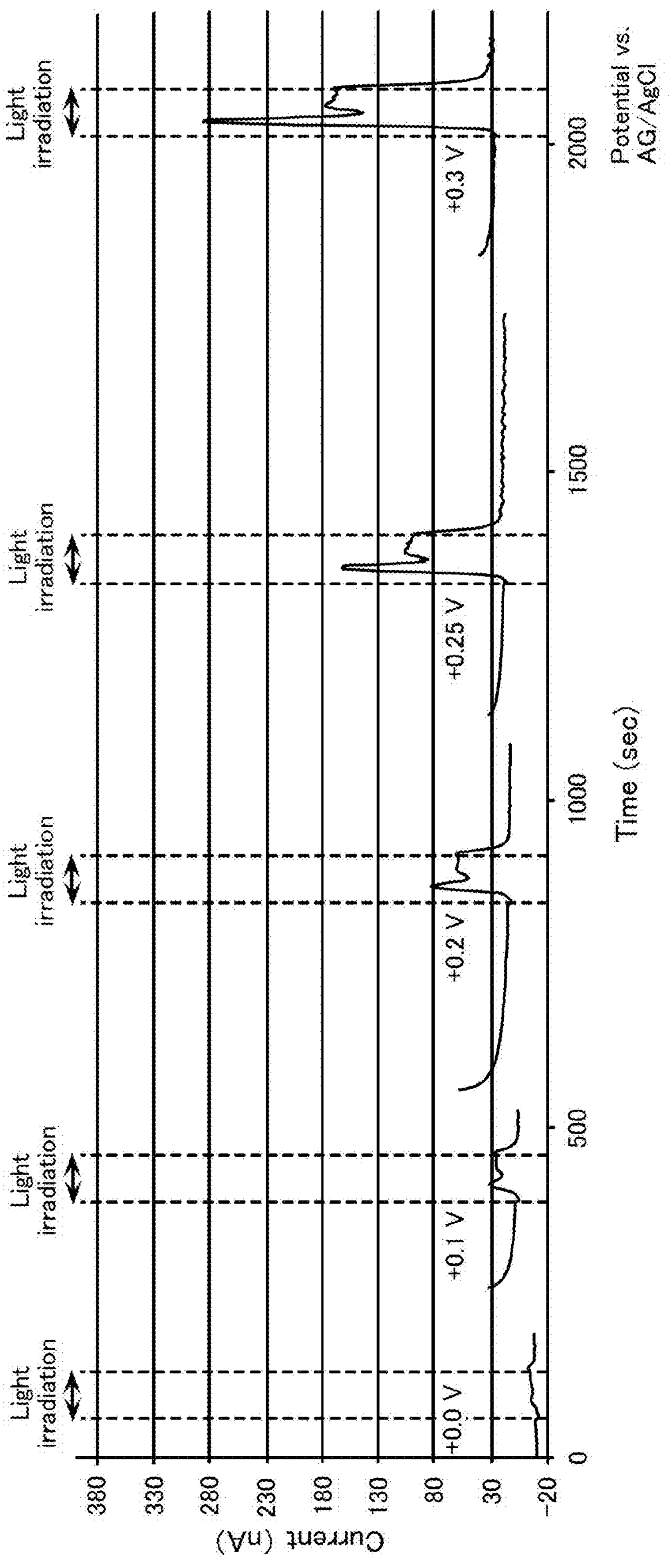
FIG. 14 is a diagram illustrating results of measuring current that flows when the culture solution of the modified cyanobacterium of Example 3 is irradiated with light.

Subsequently, current values were also measured as to the slr0688-suppressed strain of Example 2 and the cppS-introduced strain of Example 3 in the same manner as in Comparative Example 1. The results are shown in FIGS. 13 and 14. FIG. 13 is a diagram illustrating the results of measuring current that flowed when culture solution 40 of the slr0688-suppressed strain of Example 2 was irradiated with light. FIG. 14 is a diagram illustrating the results of measuring current that flowed when culture solution 40 of the cppS-introduced strain of Example 3 was irradiated with light.

As illustrated in FIG. 13, the current values (maximum values after baseline correction) measured when the potential of first electrode 13 based on reference electrode 16 was +0.0 V, +0.1 V, +0.2 V, +0.25 V, and +0.3 V were approximately +90 nA, approximately +250 nA, approximately +560 nA, approximately +750 nA, and approximately +1100 nA, respectively, in culture solution 40 of the slr0688-suppressed strain of Example 2.

As illustrated in FIG. 14, the current values (maximum values after baseline correction) measured when the potential of first electrode 13 based on reference electrode 16 was +0.0 V, +0.1 V, +0.2 V, +0.25 V, and +0.3 V were approximately +10 nA, approximately +20 nA, approximately +70 nA, approximately +150 nA, and approximately +260 nA, respectively, in culture solution 40 of the cppS-introduced strain of Example 3.

As illustrated in FIGS. 13 and 14, the current values were elevated in a potential-dependent manner.

As described above, the current values were able to be measured for culture solutions 40 of all the 3 strains when the potential of first electrode 13 based on reference electrode 16 was controlled to +0.3 V. Therefore, these current values were extracted and compared in Table 5.

TABLE 5

| | Strain used in measurement | Photocurrent upon application of +0.3 V (μA) |
|---|---|---|
| Comparative Example 1 | Synechocystis dCas9 strain | <0.001 |
| Example 2 | Synechocystis dCas9 slr0688_sgRNA strain | 1.1 |
| Example 3 | Synechocystis CppS TetR strain | 0.26 |

As described in Table 5, the current flowing in culture solution 40 by the light irradiation of culture solution 40 (hereinafter, referred to as photocurrent) was improved by 1000 times in culture solution 40 of the slr0688-suppressed strain of Example 2 compared with culture solution 40 of the control strain of Comparative Example 1 when the potential of first electrode 13 based on reference electrode 16 was controlled to +0.3 V. The photocurrent was improved by approximately 300 times in culture solution 40 of the cppS-introduced strain of Example 3 compared with culture solution 40 of the control strain of Comparative Example 1 when the potential of first electrode 13 based on reference electrode 16 was controlled to +0.3 V.

These results demonstrated that the modified cyanobacterium according to the present embodiment exhibits approximately 300- to 1000-fold improvement in extracellular electron transfer efficiency by partially detaching the outer membrane of cyanobacterium from the cell wall or by improving the material permeability of the outer membrane of cyanobacterium.

(7) Discussion

The results described above suggest that in the modified cyanobacterium obtained by modifying cyanobacterium such that protein in the cell easily leaked out by weakening the binding between the outer membrane and the cell wall, as in Example 1 and Example 2, the outer membrane was disrupted and came off, whereby organic substances (e.g., quinone) other than protein also easily leaked out to the outside of the cell. This probably led to the photocurrent approximately 5 times higher than that for the modified cyanobacterium in which the protein permeability of the outer membrane of cyanobacterium was improved, as in Example 3.

Thus, for more improving the efficiency of electron transfer of the modified cyanobacterium with the outside, a partially stripped state of the outer membrane was found more effective than the expression of the organic channel protein.

The electron carrier of the present disclosure is very advantageous in that the outer membrane can be moderately detached and stripped, because the modified cyanobacterium also has improved protein production efficiency and can be repeatedly used even after protein retrieval. From the protein identification results described above, the modified cyanobacterium can also be allowed to secrete the desired protein by modifying a gene encoding a periplasmic protein. In the production of such a useful material, use of the electron carrier of the present disclosure enables the useful material to be produced stably and efficiently by the application of sunlight as well as electric energy.

Although an electron carrier, an electron carrier production method, and an electron transfer method according to the present disclosure are described above based on the foregoing embodiments, the present discloser is not limited by the foregoing embodiments. Forms obtained by making various modifications to the foregoing embodiments that can be conceived by those skilled in the art as well as other forms realized by combining some of the components in the foregoing embodiments, for as long as they do not depart from the essence of the present disclosure, are included in the scope of the present disclosure.

In the embodiments described above, examples are described in which extracellular electron transfer efficiency is improved by suppressing or losing a function of a protein involved in binding between an outer membrane and a cell wall of cyanobacterium and thereby weakening the binding between the outer membrane and the cell wall. However, the present disclosure is not limited thereby. For example, the binding between the outer membrane and the cell wall may be weakened or the outer membrane may be rendered fragile by applying external force to cyanobacterium. Alternatively, the outer membrane may be rendered fragile by adding an enzyme or a drug to the culture solution of cyanobacterium.

INDUSTRIAL APPLICABILITY

The electron carrier, the electron carrier production method, and the electron transfer method of the present disclosure can efficiently supply electrons to the outside of the electron carrier and can therefore perform treatment of sludge or sewage, etc. and power generation at the same time. According to the present disclosure, the electron carrier can efficiently receive electrons from the outside and can therefore use electric energy when the light quantity of sunlight is insufficient. Hence, according to the present disclosure, useful material production, soil amelioration, effluent treatment, or power generation, etc. can be efficiently performed in the food, pharmaceutical, or chemical field.

The invention claimed is:

1. An electron carrier comprising:

a modified cyanobacterium in which at least:

(i) a function of a protein involved in binding between an outer membrane and a cell wall of cyanobacterium is suppressed; or (ii) a channel protein which improves protein permeability of the outer membrane is expressed, wherein the modified cyanobacterium performs at least one of supplying electrons to an outside or taking in electrons from the outside, wherein in (i), the protein involved in the binding between the outer membrane and the cell wall is at least one of a surface layer homology (SLH) domain-containing outer membrane protein or a cell wall-pyruvic acid modifying enzyme, wherein the SLH domain-containing outer membrane protein is:

Slr1841 having the amino acid sequence of SEQ ID NO: 1;

NIES970_09470 having the amino acid sequence of SEQ ID NO: 2;

Anacy_3458 having the amino acid sequence of SEQ ID NO: 3; or a protein having an amino acid sequence that is at least 50 percent identical to the amino acid sequence of any one of the Slr1841, the NIES970_09470, and the Anacy_3458, and wherein the cell wall-pyruvic acid modifying enzyme is:

Slr0688 having the amino acid sequence of SEQ ID NO: 4;

Synpcc7942_1529 having the amino acid sequence of SEQ ID NO: 5;

Anacy_1623 having the amino acid sequence of SEQ ID NO: 6; or a protein having an amino acid sequence that is at least 50 percent identical to the amino acid sequence of any one of the Slr0688, the Synpcc7942_1529, and the Anacy_1623.

2. The electron carrier according to claim 1, wherein the modified cyanobacterium:

under light, generates an electron; and releases the electron generated to an outside of the outer membrane.

3. The electron carrier according to claim 1, wherein the modified cyanobacterium:

takes an electron present outside the outer membrane into an inside of the cell wall; and uses the electron inside the cell wall.

4. The electron carrier according to claim 1, wherein in the (ii), the channel protein which improves the protein permeability of the outer membrane is:

CppS having an amino acid sequence represented by SEQ ID NO: 13;

CppF having an amino acid sequence represented by SEQ ID NO: 14; or a protein having an amino acid sequence that is at least 50 percent identical to the amino acid sequence of either one the CppS and the CppF.

5. The electron carrier according to claim 1, wherein in the (ii), a gene encoding the channel protein which improves the protein permeability of the outer membrane has been introduced.

6. The electron carrier according to claim 5, wherein the gene encoding the channel protein which improves the protein permeability of the outer membrane is a chloroplast-derived gene.

7. The electron carrier according to claim 5, wherein in the (ii), the gene encoding the channel protein which improves the protein permeability of the outer membrane is:

cppS having a nucleotide sequence represented by SEQ ID NO: 15;

cppF having a nucleotide sequence represented by SEQ ID NO: 16; or a gene having a nucleotide sequence that is at least 50 percent identical to the nucleotide sequence of either one of the cppS and the cppF.

8. An electron carrier comprising:

a modified cyanobacterium in which at least:

(i) a function of a protein involved in binding between an outer membrane and a cell wall of cyanobacterium is suppressed; or (ii) a channel protein which improves protein permeability of the outer membrane is expressed, wherein the modified cyanobacterium performs at least one of supplying electrons to an outside or taking in electrons from the outside, wherein in (i), a gene which causes expression of the protein involved in the binding between the outer membrane and the cell wall is deleted or inactivated, wherein the gene which causes expression of the protein involved in the binding between the outer membrane and the cell wall is at least one of a gene encoding an SLH domain-containing outer membrane protein or a gene encoding a cell wall-pyruvic acid modifying enzyme, wherein the gene encoding the SLH domain-containing outer membrane protein is:

slr1841 having the nucleotide sequence of SEQ ID NO: 7;

nies970_09470 having the nucleotide sequence of SEQ ID NO: 8;

anacy_3458 having the nucleotide sequence of SEQ ID NO: 9; or a gene having a nucleotide sequence that is at least 50 percent identical to the nucleotide sequence of any one of the slr1841, the nies970_09470, and the anacy_3458, and wherein the gene encoding the cell wall-pyruvic acid modifying enzyme is:

s1r0688 having the nucleotide sequence of SEQ ID NO: 10;

synpcc7942_1529 having the nucleotide sequence of SEQ ID NO: 11;

anacy_1623 having the nucleotide sequence of SEQ ID NO: 12; or a gene having a nucleotide sequence that is at least 50 percent identical to the nucleotide sequence of any one of the slr0688, the synpcc7942_1529, and the anacy_1623.

* * * * *

SEQUENCE LISTING

```
<160> NUMBER OF SEQ ID NOS: 34

<210> SEQ ID NO 1
<211> LENGTH: 630
<212> TYPE: PRT
<213> ORGANISM: Synechocystis PCC6803
```

-continued

<400> SEQUENCE: 1

```
Met Leu Lys Leu Ser Trp Lys Ser Leu Leu Val Ser Pro Ala Val Ile
1               5                   10                  15

Gly Ala Ala Leu Val Ala Gly Ala Ala Ser Ala Ala Pro Asp Asn Val
            20                  25                  30

Thr Asn Ala Gln Val Leu Asp Gln Leu Asp Gln Tyr Thr Ala Glu Gly
        35                  40                  45

Gln Ser Ser Ala Ile Asp Gln Val Thr Ser Val Ser Glu Leu Arg Asp
    50                  55                  60

Val Gln Pro Thr Ala Trp Ala Tyr Glu Ala Leu Lys Ser Leu Val Glu
65                  70                  75                  80

Arg Tyr Gly Cys Ile Val Gly Tyr Pro Asp Arg Thr Phe Arg Gly Asp
                85                  90                  95

Arg Ala Leu Ser Arg Trp Glu Phe Ala Ala Gly Leu Asn Ala Cys Met
            100                 105                 110

Asn Val Met Glu Arg Leu Ile Gln Glu Asn Val Ala Val Leu Arg Glu
        115                 120                 125

Asp Ile Asp Lys Leu Lys Arg Leu Met Gln Glu Phe Glu Ala Glu Leu
    130                 135                 140

Ala Ala Leu Gly Ala Arg Val Asp Asn Leu Glu Ala Arg Thr Ser Phe
145                 150                 155                 160

Leu Glu Asp His Gln Phe Ser Thr Thr Thr Lys Leu Thr Gly Glu Val
                165                 170                 175

Ile Phe Ala Pro Thr Ala Ile Phe Gly Thr Lys Lys Thr Leu Asn Asn
            180                 185                 190

Gln Thr Asp Asn Asn Gln Ala Val Phe Gln Asn Arg Val Arg Leu Gln
        195                 200                 205

Phe Asn Thr Ser Phe Ser Gly Glu Asp Leu Leu Val Thr Arg Leu Ala
    210                 215                 220

Ala Gly Asn Gly Asn Arg Phe Lys Ser Phe Tyr Pro Thr Gln Asn Val
225                 230                 235                 240

Ile Asp Pro Glu Thr Gly Asn Pro Ile Gly Ile Val Gly Asp Tyr Tyr
                245                 250                 255

Glu Ser Pro Thr Phe Thr Gln Val His Gln Leu Ser Pro Gly Asp Asn
            260                 265                 270

Asn Asn Val Ala Val Asp Trp Leu Ala Tyr Tyr Val Pro Leu Asp Leu
        275                 280                 285

Gly Glu Asn Phe Arg Leu Asn Asn Tyr Ile Ala Ala Trp Gly Gly Ile
    290                 295                 300

Trp Asp Asp Phe Val Pro Thr Leu Asn Pro Tyr Phe Asp Asp Tyr Thr
305                 310                 315                 320

Gly Gly Lys Gly Ser Leu Ser Gln Phe Thr Ala Gln Asn Pro Ile Tyr
                325                 330                 335

Ser Ile Gly Gly Gly Thr Gly Ile Gly Thr Ser Leu Glu Leu Gly Phe
            340                 345                 350

Leu Ser Asn Leu Leu Gly Pro Thr Ser Leu Ser Leu Gly Tyr Leu Ala
        355                 360                 365

Ser Thr Gly Asn Asn Pro Ser Ser Gly Gly Ser Val Thr Asn Pro Ala
    370                 375                 380

Thr Gly Asn Asn Tyr Asp Phe Ser Ser Gly Gly Asn Gly Leu Phe Asn
385                 390                 395                 400

Gly Gly Tyr Ser Ala Leu Ala Gln Ile Thr Thr Asn Ile Phe Asp Arg
                405                 410                 415
```

Val Ser Leu Gly Phe Thr Tyr Val Asn Ala Tyr Thr Thr Pro Asp Ala
420 425 430

Ala Ile Phe Gly Lys Gly Gly Thr Gln Gly Ile Val Gly Thr Thr Ala
435 440 445

Ala Asn Leu Asn Arg Ser Glu Leu Asn Asp Asp Phe Val Asn Gly Leu
450 455 460

Gly Val Gly Ala Pro Pro Val Asp Ala Ala Thr Tyr Asn Asn Asn Val
465 470 475 480

Ser Gly Gly Ser Thr Ser Gly Asn Val Ile Asn Pro Tyr Asp Phe Gly
485 490 495

Gly Lys Gln Thr Asn Ser Tyr Gly Val Gln Met Ala Trp Asn Ile Ala
500 505 510

Asp Trp Leu Ser Phe Ser Ala Tyr Gly Ser Tyr Thr Asn Val Thr Leu
515 520 525

Ile Gly Lys Asp Asn Gly Asp Ile Trp Thr Tyr Gly Gly Gly Phe Ala
530 535 540

Phe Pro Asp Leu Gly Lys Glu Gly Asn Val Leu Gly Ile Phe Ala Gly
545 550 555 560

Val Gln Pro Tyr Val Ser Gly Phe Thr Asn Asn Thr Leu Gly Thr Thr
565 570 575

Phe Val Thr Thr Ala Asn Pro Leu Gln Val Glu Leu Phe Tyr Lys Tyr
580 585 590

Gln Leu Thr Asp Asn Leu Ser Ile Thr Pro Gly Val Ile Trp Ile Ser
595 600 605

Lys Pro Glu Gln Thr Thr Asn Ala Thr Asp Ala Phe Ile Gly Thr Val
610 615 620

Arg Gly Thr Phe Thr Phe
625 630

<210> SEQ ID NO 2
<211> LENGTH: 532
<212> TYPE: PRT
<213> ORGANISM: Synechococcus sp. NIES-970

<400> SEQUENCE: 2

Met Ser Lys Ala Met Arg Asn Leu Leu Ser Gly Ala Thr Val Ala Leu
1 5 10 15

Gly Ala Thr Val Ala Phe Ser Gly Ala Ala Ile Ala Glu Glu Asn Gln
20 25 30

Ala Val Leu Asp Gln Ile Ser Gln Tyr Ser Thr Asp Asn Ser Val Ala
35 40 45

Gln Val Asn Ser Val Phe Gln Leu Ser Asp Val Ser Pro Ser Asp Trp
50 55 60

Ala Phe Asp Ala Leu Arg Asn Leu Val Glu Asn Tyr Asn Cys Ile Val
65 70 75 80

Gly Tyr Pro Asp Gly Thr Phe Arg Gly Thr Arg Pro Leu Ser Arg Tyr
85 90 95

Glu Phe Ala Ala Gly Leu Asn Ala Cys Leu Gln Gln Ile Glu Arg Met
100 105 110

Leu Glu Gly Gly Gly Glu Val Thr Gln Glu Asp Leu Ala Ala Leu Arg
115 120 125

Arg Leu Leu Asn Glu Phe Glu Ala Glu Leu Ala Thr Leu Gly Ala Arg
130 135 140

Val Asp Asp Leu Asp Gly Arg Val Glu Phe Leu Glu Asp Asn Gln Phe

-continued

```
145                 150                 155                 160

Ser Thr Thr Thr Lys Leu Asn Gly Glu Val Ile Phe Asn Leu Gly Gly
                165                 170                 175

Ala Phe Gly Asp Ser Arg Ala Asp Gly Pro Gly Pro Ile Asp Asp Glu
            180                 185                 190

Phe Thr Phe Ser Asn Arg Val Arg Leu Asn Leu Asp Thr Ser Phe Thr
        195                 200                 205

Gly Arg Asp Arg Leu Arg Thr Arg Leu Glu Ala Gly Asn Ile Thr Arg
    210                 215                 220

Leu Asp Arg Ala Thr Gly Val Asp Ala Ala Arg Leu Gly Phe Asp Thr
225                 230                 235                 240

Asn Asn Gly Asn Asp Val Glu Ile Gly Lys Leu Phe Tyr Arg Phe Pro
                245                 250                 255

Val Gly Asp Asn Ile Thr Ala Tyr Val Gly Ala Val Gly Leu Gly Leu
            260                 265                 270

Asp Asp Ile Phe Asp Val Thr Asn Pro Tyr Phe Glu Ser Ser Gly Asn
        275                 280                 285

Gly Ala Leu Ser Arg Phe Gly Arg Phe Asn Pro Ile Tyr Arg Gly Pro
    290                 295                 300

Asp Gly Ala Gly Ala Gly Phe Asn Phe Asp Leu Gly Glu Arg Val Thr
305                 310                 315                 320

Phe Ser Ala Ala Tyr Leu Ala Asp Asp Gly Gly Ala Ser Ser Pro Val
                325                 330                 335

Ser Lys Asn Gly Leu Phe Asn Gly Asn Tyr Thr Ala Gly Ala Gln Leu
            340                 345                 350

Asp Phe Ala Pro Ser Asp Asn Ile Met Leu Ser Ala Val Tyr Thr Arg
        355                 360                 365

Arg Tyr Gln Gln Gly Gly Asp Val Asn Leu Ser Gly Ser Thr Gly Ser
    370                 375                 380

Asp Phe Ala Ala Asp Pro Phe Gly Phe Ala Ala Ser Ser Asn Asn Phe
385                 390                 395                 400

Gly Leu Gln Gly Ser Trp Leu Ile Gly Glu Lys Phe Asn Leu Gly Gly
                405                 410                 415

Trp Val Gly Tyr Thr Asn Ala Asp Leu Lys Asp Pro Val Val Thr Gly
            420                 425                 430

Asn Ala Asp Val Trp Asn Trp Ala Val Asn Ala Ala Leu Leu Asp Val
        435                 440                 445

Gly Gly Glu Gly Asn Thr Leu Gly Phe Ile Phe Gly Gln Pro Pro Lys
    450                 455                 460

Leu Thr Glu Ala Asp Ile Asp Phe Gly Gly Gly Pro Ile Thr Phe Asp
465                 470                 475                 480

Gly Ser Asp Ser Thr Tyr Leu Ala Glu Leu Gln Tyr Arg Tyr Lys Val
                485                 490                 495

Asn Asn Asn Ile Thr Ile Thr Pro Gly Ala Tyr Val Leu Trp Asn Pro
            500                 505                 510

Asn Gln Asn Asp Ala Asn Asp Thr Ile Val Val Gly Thr Val Arg Thr
        515                 520                 525

Thr Phe Ser Phe
    530

<210> SEQ ID NO 3
<211> LENGTH: 567
<212> TYPE: PRT
<213> ORGANISM: Anabaena cylindrica PCC 7122
```

<400> SEQUENCE: 3

Met Ser Asn Leu Leu Trp Lys Ser Leu Val Val Ser Pro Ala Val Leu
1               5                   10                  15

Gly Ala Ala Leu Leu Val Ser Gly Thr Ala Ile Ala Ser Pro Ala Ala
            20                  25                  30

Gly Asn Ser Ala Ser Asn Ala Ala Thr Glu Val Ser Ile Leu Glu Thr
        35                  40                  45

Gln Ala Ala Thr Glu Val Val Gln Gln Pro Val Val Leu Ala Gln Val
    50                  55                  60

Lys Gln Asp Thr Gln Val Leu Asp Gln Val Lys Arg Tyr Ser Asn Glu
65                  70                  75                  80

Gly Gln Asn Leu Gln Ser Gln Val Thr Ser Val Ser Gln Phe Ser Asp
                85                  90                  95

Val Gln Pro Thr Asp Trp Ala Phe Gln Ala Leu Gln Ser Leu Val Glu
            100                 105                 110

Arg Tyr Gly Cys Ile Ala Gly Tyr Pro Asn Gly Thr Tyr Arg Gly Asn
        115                 120                 125

Arg Ala Leu Thr Arg Tyr Glu Phe Ala Ala Gly Leu Asn Ala Cys Leu
    130                 135                 140

Asp Arg Val Asn Glu Leu Ile Ala Thr Ala Thr Ala Asp Met Val Thr
145                 150                 155                 160

Lys Gln Asp Leu Ala Thr Leu Gln Arg Leu Gln Glu Glu Phe Ser Ala
                165                 170                 175

Glu Leu Ala Thr Leu Arg Gly Arg Val Asp Ala Leu Glu Ala Arg Thr
            180                 185                 190

Ala Glu Leu Glu Ala Asn Gln Phe Ser Thr Thr Thr Lys Leu Gln Gly
        195                 200                 205

Glu Ala Ile Phe Ala Leu Thr Asp Ala Phe Asn Gly Asp Ile Ala Gly
    210                 215                 220

Lys Thr Val Phe Gln Asp Arg Val Arg Leu Asn Leu Gln Ser Ser Phe
225                 230                 235                 240

Thr Gly Arg Asp Met Leu Asn Thr Arg Leu Ala Ala Gly Asn Ala Gln
                245                 250                 255

Asn Phe Gly Asn Thr Gly Glu Ser Arg Gln Thr Phe Asp Val Gly Ser
            260                 265                 270

Thr Gly Thr Asn Asn Val Val Leu Asp Lys Leu Thr Tyr Glu Ala Pro
        275                 280                 285

Val Gly Pro Ala Gln Val Tyr Ile Ala Ala Thr Gly Gly Lys His Ser
    290                 295                 300

His Tyr Ala Ala Val Asn Asn Pro Tyr Phe Phe Asp Lys Thr Asp Gly
305                 310                 315                 320

Gly Asn Gly Ala Leu Ser Thr Phe Ser Ser Glu Asn Pro Ile Tyr Arg
                325                 330                 335

Ile Gly Gly Gly Ser Gly Ile Ala Leu Asn Val Pro Phe Gly Gln Gly
            340                 345                 350

Gly Gly Ile Leu Lys Pro Ser Ser Leu Thr Leu Gly Tyr Leu Ala Ser
        355                 360                 365

Glu Ala Asn Ser Pro Ala Ala Gly Glu Gly Leu Phe Asp Gly Asn Tyr
    370                 375                 380

Ala Ala Leu Gly Gln Leu Asn Phe Asn Val Gly Asn Arg Ile Ala Leu
385                 390                 395                 400

Ala Ala Thr Tyr Val His Gly Tyr His Gly Ala Ser Ser Arg Leu Phe

```
                405                 410                 415

Asp Ser Gly Glu Gly Asp Asp Ile Val Gly Thr Ser Leu Ala Asn Asn
            420                 425                 430

Leu Ser Leu Gly Ser Ala Ser Ser Ser Asn Ser Tyr Gly Val Ser Ala
        435                 440                 445

Ala Phe Arg Pro Ser Asp Lys Leu Ser Val Ser Gly Phe Val Ser Tyr
    450                 455                 460

His Asp Ile Thr Gly Phe Gly Ala Gly Asp Asp Tyr Glu Ala Trp Ser
465                 470                 475                 480

Tyr Gly Val Gly Val Ala Leu Pro Asp Phe Gly Lys Lys Gly Asn Val
                485                 490                 495

Leu Gly Ile Phe Gly Gly Ala Gln Pro Tyr Ser Phe Asn Asn Asn Gly
            500                 505                 510

Gly Ala Asn Ser Gly Asp Ile Pro Tyr Gln Val Glu Gly Phe Tyr Lys
        515                 520                 525

Tyr Arg Val Ser Asp Asn Ile Ser Val Thr Pro Gly Val Ile Trp Leu
    530                 535                 540

Pro Ser Ile Gly Gln Ser Ser Ser Ser Glu Asp Thr Phe Ile Gly Thr
545                 550                 555                 560

Leu Arg Thr Thr Phe Thr Phe
                565


<210> SEQ ID NO 4
<211> LENGTH: 300
<212> TYPE: PRT
<213> ORGANISM: Synechocystis PCC6803

<400> SEQUENCE: 4

Met Arg Val Ile Leu Cys Gly Tyr Tyr Gly Gln Asp Asn Ala Gly Asp
1               5                   10                  15

Glu Ala Leu Leu Val Cys Leu Leu Gln Met Leu Pro Ala Thr Val Glu
            20                  25                  30

Pro Val Val Leu Ser Ala Asn Pro Gln Val Thr Thr Ala Arg Tyr Gly
        35                  40                  45

Val Lys Ala His Tyr Asn Arg Asp Trp Gly Lys Ile Trp Gln Leu Leu
    50                  55                  60

Gly Gln Cys Asp Gly Phe Ile Trp Gly Gly Gly Ser Leu Met Gln Asp
65                  70                  75                  80

Val Thr Ser Val Val Ser Pro Leu Tyr Tyr Gly Gly Leu Met Ala Ile
                85                  90                  95

Ala Gln Met Arg Arg Leu Lys Thr Ile Ala Trp Ala Gln Gly Ile Gly
            100                 105                 110

Pro Leu Arg Arg Pro Pro Leu Arg Trp Phe Thr Gln Gln Val Leu Arg
        115                 120                 125

Gly Cys Ser Gly Ile Ser Val Arg Asp Gln Ala Ser Leu Gln Leu Val
    130                 135                 140

Lys Gln Trp Gly Leu Lys Ala Phe Leu Ala Ala Asp Pro Val Trp Ser
145                 150                 155                 160

Leu Ala Ala Glu Asn Ala Ser Ser Ser Pro Ser Pro Leu Pro Met Val
                165                 170                 175

Ala Val Asn Leu Arg Ala His Pro Leu Leu Thr Leu Glu Arg Leu Ala
            180                 185                 190

Val Ile Thr Glu Ala Leu Arg Asp Phe Gln His Gln Thr Gln Thr His
        195                 200                 205
```

Val Arg Leu Ile Pro Leu Gln Lys Ser Gln Asp Leu Ala Ile Ala Glu
210 215 220

Ala Ile Ala Val Glu Leu Pro Gly Ser His Glu Ile Leu Tyr Arg Pro
225 230 235 240

Asp Pro Arg Glu Cys Lys Gly Leu Phe Arg Gly Ala Glu Phe Thr Ile
245 250 255

Gly Met Arg Leu His Ser Leu Ile Met Ala Ala Ala Glu Gly Ser Ala
260 265 270

Cys Phe Ala Leu Ser Tyr Asp Pro Lys Val Ser Arg Leu Ile Ala Glu
275 280 285

Val Gly Leu Pro Gly Arg Glu Leu Ala Asp Leu Pro
290 295 300

<210> SEQ ID NO 5
<211> LENGTH: 339
<212> TYPE: PRT
<213> ORGANISM: Synechocystis sp. PCC7942

<400> SEQUENCE: 5

Met Arg Ala Leu Leu Cys Gly Tyr Tyr Gly Glu Gly Asn Gly Gly Asp
1 5 10 15

Glu Ala Leu Leu Ala Ala Leu Leu Gln Leu Leu Pro Pro Thr Val Glu
20 25 30

Pro Leu Val Leu Ser Gly Asn Pro Ala Ala Thr Arg Thr Cys Tyr Gly
35 40 45

Val Glu Ala Cys Asp Arg Arg Ser Gly Ala Ala Val Trp Gln Ala Leu
50 55 60

Arg Arg Ser Asp Leu Phe Ile Phe Gly Gly Gly Ser Leu Ile Gln Asp
65 70 75 80

Val Thr Ser Trp Thr Ser Pro Leu Tyr Tyr Cys Gly Leu Met Gly Leu
85 90 95

Ala Gln Gln Leu Gly Leu Lys Thr Ile Ala Trp Ala Gln Gly Ile Gly
100 105 110

Pro Leu Gln Arg Lys Arg Thr Arg Trp Leu Ala Arg Arg Thr Phe Gln
115 120 125

His Cys Asp Arg Ile Thr Val Arg Asp Arg Gly Ser Ala Ala Leu Leu
130 135 140

Lys Glu Trp Gly Ile Ser Val Ala Ile Ala Pro Asp Pro Val Trp Ala
145 150 155 160

Leu Glu Pro Leu Pro Leu Asp Gln Pro Leu Ser Asn Gln Glu Ala Ile
165 170 175

Ala Val Cys Leu Arg Pro His Pro Glu Leu Thr Pro Glu Arg Ser Asp
180 185 190

Arg Leu Lys Ala Ala Leu Thr Thr Leu Gln Ser Gln Thr Gln Ala Pro
195 200 205

Ile Leu Leu Ile Pro Phe His His Gln Gln Asp Arg Pro Leu Ala Ala
210 215 220

Gln Trp Ala Ser Glu Ile Pro Gln Ala Glu Val Leu Asp Trp Gln His
225 230 235 240

Pro Arg Gln Leu Leu Ser Tyr Phe Gln Ser Val Arg Leu Thr Ile Ala
245 250 255

Met Arg Phe His Gly Leu Val Met Ala Ala Ala Ala Gly Asn Arg Cys
260 265 270

Phe Gly Leu Ser Tyr Asp Pro Lys Val Arg Arg Phe Leu Asp Ala Leu
275 280 285

-continued

```
Glu Gln Pro Gly Trp Asp Leu Pro Glu Ile Pro Asp Ser Ala Glu Ala
    290                 295                 300

Ile Ala Ala Ala Trp Leu Glu Ser Trp Gln Ala Glu Pro Ile His Ala
305                 310                 315                 320

Ala Ala Ile Ala Asp Leu Arg Gln Gln Val Asp Val His Arg Gln Ala
                325                 330                 335

Leu Val Phe


<210> SEQ ID NO 6
<211> LENGTH: 350
<212> TYPE: PRT
<213> ORGANISM: Anabaena cylindrica PCC 7122

<400> SEQUENCE: 6

Met Val Lys Ile Arg Ala Leu Leu Ser Gly Tyr Tyr Gly Lys Gly Asn
1               5                   10                  15

Gly Gly Asp Glu Ala Leu Leu Ala Thr Leu Leu Gln Met Leu Pro Pro
            20                  25                  30

Asp Val Thr Pro Val Val Leu Ser Gly Asn Pro Glu Glu Thr Lys Lys
        35                  40                  45

Arg Tyr Gly Val Glu Ser Tyr Asn Arg Met Ala Phe Leu Gln Ile Ile
    50                  55                  60

Lys Ala Leu Arg Ser Cys Asp Ala Phe Ile Trp Gly Gly Gly Ser Leu
65                  70                  75                  80

Met Gln Asp Ala Thr Ser Ser Ile Ser Pro Phe Tyr Tyr Gly Gly Leu
                85                  90                  95

Met Ala Leu Ala Gln Ala Met Gly Leu Lys Thr Val Ala Trp Gly Gln
            100                 105                 110

Gly Ile Gly Pro Leu Leu Arg Ser Gln Thr Arg Trp Leu Ala Lys Arg
        115                 120                 125

Asn Phe Ala Leu Cys Thr Lys Ile Ser Val Arg Asp Arg Ser Ser Ala
    130                 135                 140

Ala Leu Leu Ser Asn Trp Gly Ile Pro His Ile Leu Ala Pro Asp Pro
145                 150                 155                 160

Val Trp Ala Leu Glu Ser Lys Pro Val Thr Glu Leu Ala Asp Leu Pro
                165                 170                 175

Lys Pro Arg Ile Ala Val Ile Leu Arg Asn His Pro Gln Leu Thr Glu
            180                 185                 190

Thr Arg Leu Ala Asn Leu Ile His Ala Leu Val Asp Leu Gln Gln Ala
        195                 200                 205

Thr Gln Ala Phe Ile Leu Leu Leu Pro Phe Gln Lys Ser Glu Asp Leu
    210                 215                 220

Asp Ile Ala Glu Lys Ile Gln Leu Gln Leu Lys Asp Val Ser Lys Ile
225                 230                 235                 240

Ile Cys Ala Glu Asp Pro Gln Leu Leu Lys Gly Ile Phe Arg Gly Val
                245                 250                 255

Glu Met Ala Ile Gly Met Arg Leu His Ser Leu Ile Met Ala Ala Ser
            260                 265                 270

Glu Gly Cys Arg Cys Phe Ala Leu Ser Tyr Asp Pro Lys Val Asn His
        275                 280                 285

Leu Met Glu Asp Leu Glu Ile Pro Gly Trp Asp Leu Lys Asp Leu Pro
    290                 295                 300

Thr Asp Val Asp Leu Met Ser Lys Thr Trp Ile Gln Tyr Tyr His Asn
305                 310                 315                 320
```

Ser Glu Ala Leu Ser Ser Glu Lys Ile Gln Ser Leu Val Asn Gly Ala
325 330 335

Phe Leu His Arg Asp Leu Leu Arg Ala Ser Leu Ser Asn Lys
340 345 350

<210> SEQ ID NO 7
<211> LENGTH: 1352
<212> TYPE: DNA
<213> ORGANISM: Synechocystis PCC6803

<400> SEQUENCE: 7
atgcttaaac tatcttggaa gtccctgtta gtgagccctg ctgtgatcgg tgccgccctt 60
gtggctggtg ctgctagtgc tgctcccgac aacgttacga atgctcaagt tttagaccaa 120
ttagaccaat acactgccga aggtcagtct tctgccattg atcaagtaac cagcgttagc 180
gaactccgcg atgtgcaacc cactgcctgg gcctatgaag cgctcaagag cttggtggaa 240
cgctacggtt gtatcgttgg ttaccctgac cgtaccttcc gtggtgatcg agccctcagc 300
cgttgggaat ttgccgctgg tcttaacgcc tgtatgaacg ttatggaacg tttgattcag 360
gaaaacgtgg ctgttctccg ggaggacatc gacaaactga aacgcctcat gcaggaattc 420
gaggcagaat tggctgcttt gggtgctcgg gttgataacc tcgaagcccg cacctctttc 480
ctcgaagacc atcagttttc taccaccacc aaattgaccg gggaagtaat atttgctccc 540
accgccattt ttggtaccaa aaagactctc aacaaccaaa ccgataacaa ccaagcggta 600
ttccagaacc gggttcgttt acagttcaac accagcttct ccggtgaaga cctgttggtc 660
actcgtctcg ccgctggtaa cggtaatcgc ttcaagagct tctatcctac tcagaatgtt 720
attgatcccg agaccggtaa ccccatcggt attgtaggtg actactatga aagccccacc 780
tttacccagg tgcaccagct ttcccccggc gacaacaaca acgtagccgt tgactggtta 840
gcttactatg ttcccttgga tctgggcgaa aacttccgtc tcaacaacta cattgctgct 900
tggggcggta tctgggatga cttcgttcct accctgaacc cctatttcga cgactacact 960
ggcggcaaag gttccttgag tcagttcacc gcccagaacc ccatctactc cattggtggc 1020
ggtactggta taggtacaag cctagagttg ggcttcctca gcaatctgtt gggccccact 1080
tccttgagct tgggttactt ggctagcacg ggcaacaacc ccagcagtgg tggttctgtt 1140
actaaccctg ccactggcaa caattatgac ttcagcagcg gtggtaacgg tttgtttaac 1200
ggtggctata gcgccttggc tcaaattacc accaacattt tcgaccgggt tagcctaggc 1260
ttcacctacg ttaatgccta caccacccct gatgccgcta tcttcggtaa aggtggcact 1320
caaggtatcg tcggtaccac tgcggctaac ct 1352

<210> SEQ ID NO 8
<211> LENGTH: 1353
<212> TYPE: DNA
<213> ORGANISM: Synechococcus sp. NIES-970

<400> SEQUENCE: 8
atgtctaaag caatgagaaa tcttctcagt ggtgcaaccg ttgctctcgg tgcaactgtt 60
gctttttctg gcgcagcgat cgccgaagaa aaccaagccg tcctcgacca gatcagtcaa 120
tacagcactg ataactccgt tgctcaggtc aacagcgttt tccagctcag cgacgtttcc 180
ccttccgatt gggcttttga cgcgctccgc aacttggttg aaaactacaa ctgtatcgtt 240
ggttatcctg atggtacttt ccgtggcact cgccccctca gccgttatga gttcgccgca 300

```
ggtctgaatg cttgtttgca acagatcgaa cggatgctcg aaggtggcgg tgaagtaacc    360

caagaagatc tcgcagccct ccgtcgtctg ctcaacgaat ttgaagcaga actagctacc    420

ctcggcgctc gtgttgatga ccttgatggc cgtgttgagt tccttgaaga caatcagttc    480

tccaccacca ccaaactgaa tggggaagtt atcttcaacc ttggtggcgc ttttggcgat    540

agcagagctg atggtcctgg cccaatcgat gatgagttca cattcagcaa tcgtgttcgt    600

ctgaacctag acactagctt cactggtcgc gatcgcctcc gcactcgtct tgaagctggc    660

aatatcactc gcttagaccg tgcaactggt gtagatgcag cccgtctcgg ctttgacact    720

aacaacggta atgatgttga aattgggaaa ttgttctacc gcttccctgt aggtgacaac    780

attactgcct atgtcggtgc cgttggccta ggtcttgatg acatatttga tgtaaccaac    840

ccatattttg agagcagcgg taatggtgcc ctctctcgtt tcggtcgttt taaccccatc    900

taccgtggcc ccgatggtgc tggtgctggt tttaacttcg atcttggtga aagagttacc    960

ttctccgcag cttaccttgc ggatgatggt ggtgctagca gccctgtctc gaagaatggc   1020

ctgttcaatg gcaactacac tgcgggtgct cagctcgatt ttgctccctc tgacaacatc   1080

atgctgtctg ccgtttatac ccgtcgctac caacagggtg gcgatgtcaa cctgagcggt   1140

agcactggta gtgattttgc tgcagatcct tttggttttg ctgcttcttc caacaacttc   1200

ggcttacaag gtagctggtt gatcggtgaa aaattcaacc ttggtggctg ggtcggctac   1260

accaatgctg atctcaaaga tcctgttgtc accggtaacg ctgatgtttg gaactgggct   1320

gttaacgccg ctctacttga tgtcggcggc gaa                                1353
```

<210> SEQ ID NO 9
<211> LENGTH: 1360
<212> TYPE: DNA
<213> ORGANISM: Anabaena cylindrica PCC 7122

<400> SEQUENCE: 9

```
atgtctaatc tattgtggaa atccttggtg gttagcccag ccgtgttggg agccgcctta     60

ttagtttcag gaacagcgat cgcatcgccc gccgcaggca actcagcctc aaatgctgct    120

actgaagtat caatactaga aacacaagcg gcaacagagg ttgttcaaca acctgtagta    180

ttggctcaag tcaagcaaga cactcaggtt ttagatcaag ttaaacgcta cagtaacgaa    240

ggtcaaaatc tacaatctca agtaacatca gtctctcagt tttccgatgt ccaaccaact    300

gactgggcat tccaagcttt gcagtccttg gtggaacgtt atggttgtat cgcaggttat    360

cccaatggta catatcgcgg aaaccgtgct ttaacccgtt atgaatttgc cgctggtttg    420

aatgcctgtt tagaccgggt gaatgaattg attgccacag caacagctga catggtgaca    480

aaacaggatt tagccacctt acagcgcttg caagaagaat ttctgctga attggcaact    540

ttacgcggtc gtgtcgatgc tttggaagca cgcactgctg agttagaagc taatcaattc    600

tctactacca ccaaattgca aggtgaagct atttttgctc tgaccgatgc ttttaatggt    660

gacattgccg gtaagaccgt ttttcaagat agagtgcgtt tgaacctgca aagcagcttc    720

acaggtcgag atatgttgaa tacccgtttg gctgcgggta atgcacaaaa ctttggaaac    780

actggggaaa gtagacaaac ctttgacgtt ggtagcactg ggactaacaa tgttgtgtta    840

gacaaactga cctatgaagc tcctgttggt ccagcacagg tctacatagc agctacaggt    900

ggtaaacaca gccattatgc tgctgttaac aacccttact tctttgataa aactgatggt    960

ggtaacggtg ctttaagtac ctttagttct gaaaacccca tctatcgaat tggtggtggt   1020

tctggtattg cccttaatgt accctttggt caaggtggcg gtattctcaa accaagttca   1080
```

```
ttgacattgg gttatttggc ttctgaggct aatagtcctg ctgctggtga aggtttgttc   1140

gacggtaact atgctgcttt aggtcagtta aactttaacg ttggtaatcg cattgcctta   1200

gctgctactt atgtacatgg ttatcatggt gctagtagcc gtttgtttga ctcaggagag   1260

ggtgatgata tcgtaggtac atcactagct aataatctca gtttaggtag cgcctcgtcc   1320

agcaactcct acggtgtttc tgctgccttc agacctagcg                         1360
```

<210> SEQ ID NO 10
<211> LENGTH: 1032
<212> TYPE: DNA
<213> ORGANISM: Synechocystis PCC6803

<400> SEQUENCE: 10

```
atgcgtgtca ttctgtgtgg ttactacggc caagacaatg ctggggatga agccctttta     60

gtctgtttgc tgcaaatgct tcctgcgacg gtggagccag tggtgctctc cgccaatccc    120

caggtcacca cagcgagata cggtgttaaa gcccactaca accgagactg ggcaaaatt    180

tggcagcttt tgggtcaatg tgacggtttt atctgggggg gaggcagttt gatgcaggat    240

gtgaccagcg tggttagtcc cctatactac ggtggtttga tggcgatcgc ccagatgcgg    300

cgtttaaaaa ccattgcctg ggcccagggc attggccccc ttagaaggcc gccgttgcgc    360

tggtttaccc aacaggtgct ccggggttgt agcggcatca gcgtacggga tcaagcttct    420

ttgcaattag ttaaacaatg ggcttaaag gcttttttag cggcggatcc ggtgtggtct    480

ttagccgctg aaaatgcgtc ttcttccccc agccctttgc ccatggtggc ggtgaatttg    540

cgggcccatc ctttgttaac cttggaacgc ttggcggtca ttaccgaagc cctaagggat    600

tttcaacacc agacccaaac ccatgtgcgg ctcattcccc tacaaaaatc ccaggatttg    660

gccattgccg aagcgatcgc cgtggaattg ccggggagtc atgaaattct ttaccgcccc    720

gaccccaggg aatgtaaagg tttgttccgg ggggcggaat tcaccattgg catgcggctc    780

cacagtttaa tcatggccgc ggcggagggc agtgcctgct ttgcccttag ttatgaccct    840

aaagttagtc gtttaatcgc agaggtggga ctaccgggcc gggaattggc ggatttaccc    900

agggatagca acgaactcag ccaggtttgg cagggacatt tccggcaaag acaaccctct    960

accggggtag agttcttgca aaaatctgcc cttcagcatc aaactttgtt gcagaaaatt   1020

tttgttgact ag                                                       1032
```

<210> SEQ ID NO 11
<211> LENGTH: 1020
<212> TYPE: DNA
<213> ORGANISM: Synechocystis sp. PCC7942

<400> SEQUENCE: 11

```
atgcgggcgt tgctctgtgg ctattacgga gagggcaatg ggggagatga ggcgctgttg     60

gcagcgctgt tgcaactctt gccgccgaca gtggaaccgc tggtgctgtc ggggaatcct    120

gcggcaactc gcacttgcta cggcgtagaa gcttgcgatc gccgatcggg ggctgcggtt    180

tggcaggcac tgcgacgcag tgatctattc atctttggcg gcggcagcct gattcaagat    240

gtcacaagct ggacgagccc tctctactac tgcggtctga tggggctggc acaacagtta    300

ggtctcaaaa cgatcgcctg ggcccagggc attgggccac tgcagcgcaa acgaacccgc    360

tggttggcac gccgaacgtt tcagcactgc gatcgcatta cagtgcgcga tcgcggttct    420

gctgccttgc taaaagagtg gggatttct gtggcgattg ccccggatcc cgtttgggct    480
```

-continued ttagagccgc tgcctttaga tcagccgctg tcgaaccaag aggcgatcgc ggtttgtctg 540
cggccccacc ctgagttgac gcctgagcgc agcgatcgct tgaaagctgc cctgacaact 600
ctgcaatcgc aaacccaagc acccatcctg ctgattccct tccaccacca gcaagatcga 660
ccactggccg cgcaatgggc aagcgaaatt ccccaagcag aagttttgga ctggcagcat 720
ccgcgccagc tcctcagcta ctttcagtcg gtgcgattaa cgatcgccat gcgcttccat 780
ggattagtga tggcagcagc ggctggaaat cgttgctttg gcctcagcta tgaccccaaa 840
gtgcgccgtt tcctggatgc ccttgagcaa cccggctggg atttgccgga gattccagac 900
tctgctgagg cgatcgcggc cgcttggtta gagtcttggc aagcagaacc gattcatgcc 960
gctgcgatcg cggacctccg tcagcaagtg gatgtccatc gccaggcttt agttttttga 1020

<210> SEQ ID NO 12
<211> LENGTH: 1053
<212> TYPE: DNA
<213> ORGANISM: Anabaena cylindrica PCC 7122

<400> SEQUENCE: 12
ctacttatta ctcaatgatg ctctcaataa atcccgatgt aaaaaagctc catttactaa 60
agattgtatt ttctcagatg ataatgcttc gctattgtga taatattgaa tccaggtttt 120
actcattaaa tctacatcag ttggtaaatc ctttaaatcc catccaggta tttctaaatc 180
ttccatcaaa tggttaacct tggggtcata actcaaagca aaacaacgac aaccttcact 240
agctgccata attaaactgt gtagacgcat ccctattgcc atttctacac cacgaaatat 300
accttttaaa agttgtggat cttctgcaca gataatttta ctaacatctt ttaattgcag 360
ttgaattttt tctgcaatat ctaaatcttc actttttttga aaaggcaata ataaaataaa 420
tgcttgggta gcttgttgta aatcaactaa ggcatggatt aaatttgcta accgagtttc 480
tgtaagttgg ggatgatttc ttaaaataac ggcaattcta ggttttggta aatctgctaa 540
ttctgttact ggtttagatt ctaaagccca aactggatca ggtgcaagaa tatgaggtat 600
gccccaattt gataataaag ccgcactaga gcgatcgcgt acactgattt tagtacaaag 660
agcaaaattt cgctttgcta accaacgagt ttgcgatcgc aataaaggcc ctattccctg 720
tccccaagct acagttttca aacccatcgc ttgagctaaa gccattaatc ccccataata 780
aaaagggcta atgctgctag tcgcatcctg cattaaactt ccaccacccc agatgaaagc 840
atcacaggaa cgcaaagctt tgataatctg caaaaacgcc atacggttgt aactttccac 900
accataacgc tttttagttt cctcaggatt cccagaaagc accacaggcg ttacatcagg 960
tggtagcatt tgcagaagtg tcgccaacaa agcttcatca ccaccattac ctttaccgta 1020
atacccagac aataacgccc gtatcttcac cat 1053

<210> SEQ ID NO 13
<211> LENGTH: 335
<212> TYPE: PRT
<213> ORGANISM: Cyanophora paradoxa NIES-547

<400> SEQUENCE: 13

Met Ala Pro Glu Cys Thr Val Val Asn Ser Gly Ile Thr Ser Val Gly
1 5 10 15

Asp Val Arg Thr Ser Ala Thr Ala Gly Val Gln Thr Asn Ser Val Tyr
20 25 30

Val Thr Ala Gln Leu Pro Gln Pro Val Val Glu Ala Gln Thr Phe Pro
35 40 45

-continued

```
Val Pro Ile Thr Val Asn Lys Thr Val Ser Lys Thr Tyr Ala Ala Gln
    50                  55                  60

Asp Ile Pro Lys Asn Glu Lys Glu Ser Val Ser Thr Val Gln Ile Pro
65                  70                  75                  80

Val Lys Glu Tyr Thr Lys Ile His Tyr Asp Tyr Glu Leu Pro Glu Asn
                85                  90                  95

Asn Val Glu Thr Val Asp Glu Val Lys Asp Ile Ile Val Ser Asp Phe
            100                 105                 110

Ile Ser Glu Thr Tyr Glu Phe Asp Phe Pro Glu Asp Thr Ile Lys Glu
        115                 120                 125

Glu Lys Val Ser Ile Pro Val Tyr Glu Glu Val Val Thr Thr Lys Thr
    130                 135                 140

Tyr Lys Val Asn Leu Pro Gln Asp Ser Glu Thr Arg Val Glu Asn Thr
145                 150                 155                 160

Phe Thr Val Pro Ala Thr Lys Tyr Thr Thr Thr Thr Tyr Asp Tyr Cys
                165                 170                 175

Gly Gln Ile Pro Glu Cys Lys Thr Asp Tyr Lys Glu Tyr Thr Gln Lys
            180                 185                 190

Leu Asp Val Thr Lys Thr Glu Glu Thr Lys Tyr Lys Tyr Glu Val Pro
        195                 200                 205

Leu Lys Asp Lys Ala Leu Cys Pro Glu Asp Leu Thr Val Glu Gly Lys
    210                 215                 220

Ile Lys Thr Ala Lys Val Val Asn Tyr Asp Leu Pro Ala Asp Ser Val
225                 230                 235                 240

Lys Glu Glu Thr Ser Glu Glu Thr Ile Asn Gln Thr Val Val Tyr Ala
                245                 250                 255

Thr Asp Phe Lys Pro Leu Pro Cys Asn Ser Gly Asn Cys Pro Ala Lys
            260                 265                 270

Gly Ala Val Pro Ser Val Tyr Asp Phe Gly Ser Asn Pro Ile Leu Asn
        275                 280                 285

Pro Gln Leu Asp Ala Glu Thr Gln Ala Val Asp Leu Gln Ala Asp Tyr
    290                 295                 300

Met Asp Met Ile Ile Gly Ala Ser Ser Glu Ala Val Asp Ser Asp Ile
305                 310                 315                 320

Leu Ile Asp Ser Gln Ser Glu Glu Ala Val Glu Ile Glu Leu Leu
                325                 330                 335


<210> SEQ ID NO 14
<211> LENGTH: 375
<212> TYPE: PRT
<213> ORGANISM: Cyanophora paradoxa NIES-547

<400> SEQUENCE: 14

Met Ser Arg Pro Glu Asn Val Ala Ser Leu Pro Ile Gly Glu Gly Ala
1               5                   10                  15

Ala Pro Ala His Pro Ile Pro Ser Ile Pro Ala Ala Glu Cys Lys Pro
            20                  25                  30

Ala Ala Arg Ile Glu Pro Glu Thr Ser Gln Lys Tyr Gly Thr Leu Tyr
        35                  40                  45

Thr Thr Gln Val Pro Tyr Ile Gln Thr Thr Thr Glu Tyr Glu Glu Tyr
    50                  55                  60

Asp Ile Pro Glu Asp Ser Val Ile Val Glu Thr Arg Pro Ile Lys Val
65                  70                  75                  80

Pro Phe Ser Glu Thr Thr Thr Lys Thr Trp Glu Val Glu Leu Pro Pro
                85                  90                  95
```

-continued

```
Ala Gly Gln Glu Val Ser Tyr Gly Thr Leu Ala Leu Pro Val Glu Lys
            100                 105                 110

Val Val His Thr Ser Tyr Asp Tyr Gln Leu Pro Ala Lys Gln Ala Thr
        115                 120                 125

Thr Glu Pro Ser Pro Ala Glu Ile Thr Ala Lys Lys Ile Thr Ser Ile
    130                 135                 140

Asp Tyr Asp Tyr Glu Leu Pro Glu Asn Lys Ala Val Tyr Thr Thr Lys
145                 150                 155                 160

Val Tyr Met Ile Pro Ile Glu Glu Thr Ile Val Gln Thr Lys Thr Tyr
                165                 170                 175

Ser Ala Lys Leu Pro Ser Asp Tyr Glu Ala Glu Glu Lys Thr Asp Val
            180                 185                 190

Glu Ile Ala Gly Arg Lys Leu Thr Thr His Thr Tyr Glu Tyr Lys Val
        195                 200                 205

Pro Ser Cys Asp Thr Lys Val Tyr Ser Asp Leu Val Asp Val Asn Val
    210                 215                 220

Lys Gln Ser Val Thr Lys Ser Tyr Ala Tyr Lys Leu Pro Asp Cys Glu
225                 230                 235                 240

Lys Pro Val Glu Thr Lys Phe Ala Thr Ala Asp Gly Val Glu Thr Ile
                245                 250                 255

Thr Leu Thr Lys Asp Tyr Leu Leu Pro Cys Glu Asn Thr Thr Thr Lys
            260                 265                 270

Leu Asn Pro Thr Glu Ala Ser Val Lys Ala Ala Ala Ser Ser Ala Ala
        275                 280                 285

Thr Cys Asn Asn Cys Gly Ser Ser Pro Ser Val Asn Glu Val Arg Tyr
    290                 295                 300

Gln Tyr Asp Pro Ala Lys Val Thr Val Thr Lys Gln Leu Glu Glu Ser
305                 310                 315                 320

Met Gln Gln Ala Glu Asp Asp Ala Ile Ala Gly Glu Leu Ala Asn Met
                325                 330                 335

Ser Ser Asp Ala Glu Ser Met Pro Leu Ala Glu Ser Ser Asp Val Ala
            340                 345                 350

Asn Val Glu Ile Ser Glu Glu His Cys Glu Leu Ile Ser Glu Leu Asp
        355                 360                 365

Asn Ile Asp Ala Glu Leu Leu
    370                 375
```

<210> SEQ ID NO 15
<211> LENGTH: 1008
<212> TYPE: DNA
<213> ORGANISM: Cyanophora paradoxa NIES-547

<400> SEQUENCE: 15

```
atggccccgg agtgcaccgt cgtgaactct ggcatcacca gcgttggtga tgtccgcacc      60

tctgccaccg ctggcgtgca gaccaactcc gtctacgtga cggcccagct gccccagccg     120

gtcgttgagg cgcagacctt cccggtcccg atcaccgtca acaagacggt gtcgaagacc     180

tatgcggccc aggacatccc gaagaacgag aaggagtccg tgtcgactgt ccagatcccg     240

gtgaaggagt acaccaagat ccactacgac tatgagctcc cggagaacaa cgtcgagacc     300

gtcgatgagg tgaaggacat catcgtgtcc gacttcatct ccgagaccta cgagttcgac     360

ttcccggagg acaccatcaa ggaggagaag gtgtcgatcc cggtgtacga ggaggtcgtg     420

accaccaaga cctacaaggt caacctgccc caggacagcg agacccgcgt cgagaacact     480
```

```
ttcaccgtgc cggcgaccaa gtacaccacc accacctacg actactgcgg tcagatcccg    540

gagtgcaaga ctgactacaa ggagtacacc cagaagctcg acgtgacgaa gaccgaggag    600

accaagtaca agtacgaggt gccgctcaag gacaaggcgc tctgcccgga ggacctcacc    660

gtcgagggca agatcaagac cgctaaggtc gtgaactacg atctgcccgc ggactccgtg    720

aaggaggaga ccagcgagga gaccattaac cagactgtcg tgtacgcgac tgacttcaag    780

cccctgccct gcaactctgg caactgcccg gcgaagggtg cggtgccgtc ggtgtacgac    840

ttcggctcga accccatcct gaacccccag ctcgacgcgg agacgcaggc ggttgacctc    900

caggcggatt acatggacat gatcatcggc gctagctctg aggcggtgga ctctgacatc    960

ctcatcgaca gccaaagcga ggaggcggtc gagatcgagc ttctgtaa                1008
```

<210> SEQ ID NO 16
<211> LENGTH: 1128
<212> TYPE: DNA
<213> ORGANISM: Cyanophora paradoxa NIES-547

<400> SEQUENCE: 16

```
atgtcgcgcc ccgagaacgt tgcgagcctg ccgatcggcg agggcgctgc cccggcgcac     60

ccgattccca gcatcccggc ggctgagtgc aagcccgcgg ctcgcattga gcccgagacc    120

tcgcagaagt atggcactct ctacaccacc caggtgccgt acatccagac taccactgag    180

tacgaggagt acgacatccc ggaggactcg gtgatcgtcg agacccgccc gattaaggtc    240

ccgttctcgg agaccaccac gaagacctgg gaggtcgagc tcccgcccgc gggccaggag    300

gtttcgtacg gcactctcgc cctgccggtt gagaaggtcg tgcacacctc gtacgactac    360

cagctgccgg cgaagcaggc gaccaccgag ccgtccccgg ctgagatcac ggcgaagaag    420

atcacctcga tcgactacga ctatgagctt cctgagaaca aggcggttta caccacgaag    480

gtgtacatga tccccattga ggagaccatc gtccagacca agacctactc ggctaagctc    540

ccgtcggact acgaggcgga ggagaagact gatgttgaga tcgccggccg gaagctgacc    600

acgcacacct acgagtacaa ggtcccgagc tgcgacacca aggtttacag cgacctcgtc    660

gacgtgaacg tgaagcagtc cgtgaccaag tcgtacgcct acaagcttcc ggactgcgag    720

aagcctgttg agactaagtt cgcgaccgcg gacggtgttg agaccattac tctcaccaag    780

gactacctcc tgccctgcga gaacaccacc accaagctca acccgactga ggcgtcggtc    840

aaggcggctg cgtcgtcggc ggcgacctgc aacaactgcg gctctagccc ctcggtcaac    900

gaggtccgct accagtatga cccggccaag gtcactgtga ccaagcagct ggaggagtcg    960

atgcagcagg cggaggatga tgcgattgcg ggcgagctgg cgaacatgtc gtctgatgcg   1020

gagtcgatgc ccctggcgga gtcgagcgat gtcgcgaacg ttgagatcag cgaggagcac   1080

tgcgagctca ttagcgaact cgacaacatt gatgccgagc tgctgtaa                1128
```

<210> SEQ ID NO 17
<211> LENGTH: 40
<212> TYPE: DNA
<213> ORGANISM: Artificial Sequence
<220> FEATURE:
<223> OTHER INFORMATION: Synthesized Primer

<400> SEQUENCE: 17

```
cagtgaattc gagctcggta tatagcgttg cagtccctgg                           40
```

<210> SEQ ID NO 18
<211> LENGTH: 40

<212> TYPE: DNA
<213> ORGANISM: Artificial Sequence
<220> FEATURE:
<223> OTHER INFORMATION: Synthesized Primer

<400> SEQUENCE: 18
gattacgcca agcttgcatg accgcggtca cttcataacc 40

<210> SEQ ID NO 19
<211> LENGTH: 47
<212> TYPE: DNA
<213> ORGANISM: Artificial Sequence
<220> FEATURE:
<223> OTHER INFORMATION: Synthesized Primer

<400> SEQUENCE: 19
cagtgaattc gagctcggta ataaccgttg tcccttttgt ttcatcg 47

<210> SEQ ID NO 20
<211> LENGTH: 45
<212> TYPE: DNA
<213> ORGANISM: Artificial Sequence
<220> FEATURE:
<223> OTHER INFORMATION: Synthesized Primer

<400> SEQUENCE: 20
tgttagtgag ccctgctgtt agctcccagt atctctatca ctgat 45

<210> SEQ ID NO 21
<211> LENGTH: 51
<212> TYPE: DNA
<213> ORGANISM: Artificial Sequence
<220> FEATURE:
<223> OTHER INFORMATION: Synthesized Primer

<400> SEQUENCE: 21
acagcagggc tcactaacag ttttagagct agaaatagca agttaaaata a 51

<210> SEQ ID NO 22
<211> LENGTH: 44
<212> TYPE: DNA
<213> ORGANISM: Artificial Sequence
<220> FEATURE:
<223> OTHER INFORMATION: Synthesized Primer

<400> SEQUENCE: 22
gattacgcca agcttgcatg gggaacaagc tgaatctggg catc 44

<210> SEQ ID NO 23
<211> LENGTH: 45
<212> TYPE: DNA
<213> ORGANISM: Artificial Sequence
<220> FEATURE:
<223> OTHER INFORMATION: Synthesized Primer

<400> SEQUENCE: 23
ttttagtctg tttgctgcat agctcccagt atctctatca ctgat 45

<210> SEQ ID NO 24
<211> LENGTH: 51
<212> TYPE: DNA
<213> ORGANISM: Artificial Sequence
<220> FEATURE:
<223> OTHER INFORMATION: Synthesized Primer

<400> SEQUENCE: 24
tgcagcaaac agactaaaag ttttagagct agaaatagca agttaaaata a 51

<210> SEQ ID NO 25
<211> LENGTH: 38
<212> TYPE: DNA
<213> ORGANISM: Artificial Sequence
<220> FEATURE:
<223> OTHER INFORMATION: Synthesized Primer

<400> SEQUENCE: 25
tagatataat gtgtggtaaa ttagaggaat tcatcgca 38

<210> SEQ ID NO 26
<211> LENGTH: 41
<212> TYPE: DNA
<213> ORGANISM: Artificial Sequence
<220> FEATURE:
<223> OTHER INFORMATION: Synthesized Primer

<400> SEQUENCE: 26
cgctcttccg atctgattta aaatgtgaac gtcgtccgta g 41

<210> SEQ ID NO 27
<211> LENGTH: 45
<212> TYPE: DNA
<213> ORGANISM: Artificial Sequence
<220> FEATURE:
<223> OTHER INFORMATION: Synthesized Primer

<400> SEQUENCE: 27
tgttagtgag ccctgctgtt agctcccagt atctctatca ctgat 45

<210> SEQ ID NO 28
<211> LENGTH: 51
<212> TYPE: DNA
<213> ORGANISM: Artificial Sequence
<220> FEATURE:
<223> OTHER INFORMATION: Synthesized Primer

<400> SEQUENCE: 28
acagcagggc tcactaacag ttttagagct agaaatagca agttaaaata a 51

<210> SEQ ID NO 29
<211> LENGTH: 40
<212> TYPE: DNA
<213> ORGANISM: Artificial Sequence
<220> FEATURE:
<223> OTHER INFORMATION: Synthesized Primer

<400> SEQUENCE: 29
tccctggttc cgctggggct atggccccgg agtgcaccgt 40

<210> SEQ ID NO 30
<211> LENGTH: 40
<212> TYPE: DNA
<213> ORGANISM: Artificial Sequence
<220> FEATURE:
<223> OTHER INFORMATION: Synthesized Primer

<400> SEQUENCE: 30
atttgatgcc tggctctagt ttacagaagc tcgatctcga 40

<210> SEQ ID NO 31
<211> LENGTH: 40
<212> TYPE: DNA
<213> ORGANISM: Artificial Sequence -continued

```
<220> FEATURE:
<223> OTHER INFORMATION: Synthesized Primer

<400> SEQUENCE: 31

tagcaggtac tgcaaacgct atgccgctcc cggtgttcgc                          40


<210> SEQ ID NO 32
<211> LENGTH: 40
<212> TYPE: DNA
<213> ORGANISM: Artificial Sequence
<220> FEATURE:
<223> OTHER INFORMATION: Synthesized Primer

<400> SEQUENCE: 32

ttagaactgg taaacgatac ttactgatcg ataacgagcg                          40


<210> SEQ ID NO 33
<211> LENGTH: 19
<212> TYPE: DNA
<213> ORGANISM: Synechocystis PCC6803

<400> SEQUENCE: 33

acagcagggc tcactaaca                                                 19


<210> SEQ ID NO 34
<211> LENGTH: 19
<212> TYPE: DNA
<213> ORGANISM: Synechocystis PCC6803

<400> SEQUENCE: 34

tgcagcaaac agactaaaa                                                 19
```